United States Patent
Humayun et al.

(10) Patent No.: US 10,478,206 B2
(45) Date of Patent: Nov. 19, 2019

(54) INSTRUMENTS AND METHODS FOR THE IMPLANTATION OF CELL-SEEDED SUBSTRATES

(75) Inventors: Mark Humayun, Glendale, CA (US); Ashish Ahuja, New York, NY (US); Yu-Chong Tai, Pasadena, CA (US); Robert Grubbs, South Pasadena, CA (US); Rodrigo Brant, Los Angeles, CA (US); Trent Wells, Altadena, CA (US); Lincoln Vallance Johnson, Santa Barbara, CA (US); Sherry T. Hikita, Santa Barbara, CA (US); David Hinton, Venice, CA (US)

(73) Assignees: University of Southern California, Los Angeles, CA (US); California Institute of Technology, Pasadena, CA (US); The Regents of the University of California, Oakland, CA (US)

(*) Notice: Subject to any disclaimer, the term of this patent is extended or adjusted under 35 U.S.C. 154(b) by 736 days.

(21) Appl. No.: 14/114,160

(22) PCT Filed: Apr. 27, 2012

(86) PCT No.: PCT/US2012/035654
§ 371 (c)(1),
(2), (4) Date: Oct. 25, 2013

(87) PCT Pub. No.: WO2012/149468
PCT Pub. Date: Nov. 1, 2012

(65) Prior Publication Data
US 2015/0032207 A1    Jan. 29, 2015

Related U.S. Application Data

(60) Provisional application No. 61/481,037, filed on Apr. 29, 2011, provisional application No. 61/591,808, filed on Jan. 27, 2012.

(51) Int. Cl.
*A61B 17/29* (2006.01)
*A61F 9/007* (2006.01)
(Continued)

(52) U.S. Cl.
CPC ............ *A61B 17/2909* (2013.01); *A61F 2/14* (2013.01); *A61F 2/4601* (2013.01); *A61F 9/007* (2013.01);
(Continued)

(58) Field of Classification Search
CPC ............. A61L 2430/16; A61L 2430/00; A61F 9/0017; A61F 2/1664; A61F 9/00736;
(Continued)

(56) References Cited

U.S. PATENT DOCUMENTS 1,168,115 A * 1/1916 Rueckert ................... B25B 9/00
                                                      294/100
1,274,669 A * 8/1918 Bohn ..................... A61B 17/29
                                                       30/175
(Continued)

FOREIGN PATENT DOCUMENTS

AU    2011279250        3/2015
EP    2386272 A1 * 11/2011 ........... A61F 2/1672
(Continued)

OTHER PUBLICATIONS

U.S. Appl. No. 13/181,279, including its prosecution history, the references and the Office Actions therein, filed Jan. 12, 2012, Humayun, et al.
(Continued)

*Primary Examiner* — Scott J Medway
(74) *Attorney, Agent, or Firm* — Kilpatrick Townsend & Stockton LLP

(57) ABSTRACT

Disclosed herein are instruments and methods for delivery of substrates, including cell-seeded substrates, to target
(Continued)

tissues requiring treatment for various diseases that induce cell death, damage or loss of function. The substrates are configured to provide cells, including stem cells, with a structural support that allows interconnection with and transmission of biological signals between the cells and the target tissue.

17 Claims, 62 Drawing Sheets

(51) Int. Cl.
    *A61L 27/16*     (2006.01)
    *A61L 27/34*     (2006.01)
    *A61L 27/38*     (2006.01)
    *A61L 27/50*     (2006.01)
    *A61K 35/50*     (2015.01)
    *C12N 5/079*     (2010.01)
    *A61F 2/14*     (2006.01)
    *A61F 2/46*     (2006.01)
    *A61F 9/00*     (2006.01)
    *A61M 1/12*     (2006.01)
    *A61M 5/14*     (2006.01)
    *A61B 17/30*     (2006.01)

(52) U.S. Cl.
    CPC ........ *A61F 9/0017* (2013.01); *A61F 9/00736* (2013.01); *A61K 35/50* (2013.01); *A61L 27/16* (2013.01); *A61L 27/34* (2013.01); *A61L 27/3813* (2013.01); *A61L 27/50* (2013.01); *A61M 1/12* (2013.01); *A61M 5/14* (2013.01); *C12N 5/0621* (2013.01); *A61B 2017/2937* (2013.01); *A61B 2017/2945* (2013.01); *A61B 2017/305* (2013.01); *A61L 2430/16* (2013.01); *A61M 2202/09* (2013.01); *C12N 2506/02* (2013.01); *C12N 2533/30* (2013.01); *C12N 2533/40* (2013.01); *C12N 2533/50* (2013.01)

(58) Field of Classification Search
    CPC .. A61F 9/007; A61F 2/02; A61F 2/148; A61F 2/1662; A61B 17/29; A61B 17/2903; A61B 10/06; A61B 2017/2937; A61B 17/30; A61B 18/1442; A61B 2017/2905; A61B 17/12013; A61B 17/3417
    See application file for complete search history.

(56) References Cited

U.S. PATENT DOCUMENTS

| | | | | |
|---|---|---|---|---|
| 2,137,710 A * | 11/1938 | Anderson | ......... | A61B 17/2909 606/206 |
| 2,670,519 A * | 3/1954 | Recklitis | ......... | A01N 1/02 27/24.2 |
| 3,404,677 A * | 10/1968 | Springer | ......... | A61B 17/29 30/135 |
| 4,047,532 A | 9/1977 | Phillips et al. | | |
| 4,174,715 A * | 11/1979 | Hasson | ......... | A61B 10/04 606/127 |
| 4,325,375 A * | 4/1982 | Nevyas | ......... | A61F 2/1662 294/99.1 |
| 4,393,872 A * | 7/1983 | Reznik | ......... | A61B 10/06 600/565 |
| 4,427,014 A * | 1/1984 | Bel | ......... | A61B 10/06 600/564 |
| 4,674,500 A * | 6/1987 | DeSatnick | ......... | A61B 17/3211 30/286 |
| 4,681,102 A * | 7/1987 | Bartell | ......... | A61F 2/1678 606/1 |
| 4,700,298 A | 10/1987 | Palcic et al. | | |
| 4,702,244 A * | 10/1987 | Mazzocco | ......... | A61F 2/1602 606/107 |
| 4,715,373 A | 12/1987 | Mazzoco et al. | | |
| 4,739,760 A * | 4/1988 | Chin | ......... | A61B 17/221 604/22 |
| 4,763,650 A * | 8/1988 | Hauser | ......... | A61B 17/30 294/1.2 |
| 4,834,094 A * | 5/1989 | Patton | ......... | A61F 2/1662 606/107 |
| 4,836,201 A * | 6/1989 | Patton | ......... | A61F 2/1678 606/107 |
| 4,836,202 A * | 6/1989 | Krasner | ......... | A61F 2/1616 606/107 |
| 4,840,176 A * | 6/1989 | Ohno | ......... | A61B 17/22031 606/127 |
| 4,862,885 A * | 9/1989 | Cumming | ......... | A61F 2/1664 606/107 |
| 4,880,000 A * | 11/1989 | Holmes | ......... | A61F 2/1678 606/107 |
| 4,881,550 A * | 11/1989 | Kothe | ......... | A61B 10/02 600/564 |
| 4,919,130 A * | 4/1990 | Stoy | ......... | A61F 2/1664 606/107 |
| 4,934,363 A * | 6/1990 | Smith | ......... | A61F 2/1678 606/107 |
| 4,957,505 A * | 9/1990 | McDonald | ......... | A61F 2/1664 606/107 |
| 4,994,079 A * | 2/1991 | Genese | ......... | A61B 17/221 606/206 |
| 5,024,223 A | 6/1991 | Chow | | |
| 5,084,054 A * | 1/1992 | Bencini et al. | ......... | 606/113 |
| 5,098,439 A * | 3/1992 | Hill | ......... | A61F 2/1664 606/107 |
| 5,176,686 A * | 1/1993 | Poley | ......... | A61F 2/1616 606/1 |
| 5,190,552 A * | 3/1993 | Kelman | ......... | A61F 2/167 606/107 |
| 5,196,003 A | 3/1993 | Bilweis | | |
| 5,222,960 A * | 6/1993 | Poley | ......... | A61F 9/00736 128/898 |
| 5,238,002 A * | 8/1993 | Devlin | ......... | A61B 10/06 600/564 |
| 5,242,450 A * | 9/1993 | McDonald | ......... | A61B 17/29 606/107 |
| 5,281,230 A * | 1/1994 | Heidmueller | ......... | A61B 17/29 604/902 |
| 5,304,182 A * | 4/1994 | Rheinish | ......... | A61F 2/167 128/898 |
| 5,342,389 A * | 8/1994 | Haber | ......... | A61B 17/0469 606/148 |
| 5,395,378 A * | 3/1995 | McDonald | ......... | A61B 17/29 606/107 |
| 5,454,822 A * | 10/1995 | Schob | ......... | A61B 17/0469 112/169 |
| 5,471,992 A * | 12/1995 | Banik | ......... | A61B 10/0266 600/564 |
| 5,562,676 A * | 10/1996 | Brady | ......... | A61F 2/1664 128/898 |
| 5,571,113 A * | 11/1996 | McDonald | ......... | A61B 17/29 606/107 |
| 5,578,042 A * | 11/1996 | Cumming | ......... | A61F 2/1662 128/898 |
| 5,584,304 A * | 12/1996 | Brady | ......... | A61F 2/1664 128/898 |
| 5,630,841 A * | 5/1997 | McDonald | ......... | A61F 2/1664 128/898 |
| 5,755,732 A * | 5/1998 | Green | ......... | A61B 17/0218 30/2 |
| 5,843,780 A | 12/1998 | Thomson | | |
| 5,871,453 A * | 2/1999 | Banik | ......... | A61B 10/0266 600/564 |
| 5,873,879 A * | 2/1999 | Figueroa | ......... | A61F 2/167 606/107 |
| 5,957,944 A * | 9/1999 | Khuri | ......... | A61B 17/3211 128/898 |

(56) References Cited

U.S. PATENT DOCUMENTS

| | | | |
|---|---|---|---|
| 5,962,027 A * | 10/1999 | Hughes | A61B 90/00 424/422 |
| 5,984,939 A * | 11/1999 | Yoon | A61B 17/12013 606/139 |
| 6,117,675 A | 9/2000 | van der Kooy et al. | |
| 6,142,957 A * | 11/2000 | Diamond | A61B 10/0266 600/567 |
| 6,156,042 A | 12/2000 | Aramant | |
| 6,156,045 A * | 12/2000 | Ulbrich | A61B 17/00234 604/158 |
| 6,200,806 B1 | 3/2001 | Thomson | |
| 6,231,879 B1 | 5/2001 | Li et al. | |
| 6,254,628 B1 | 7/2001 | Wallace et al. | |
| 6,264,941 B1 | 7/2001 | Baetge et al. | |
| 6,299,895 B1 | 10/2001 | Hammang et al. | |
| 6,303,136 B1 | 10/2001 | Li et al. | |
| 6,322,804 B1 | 11/2001 | Dionne et al. | |
| 6,337,198 B1 | 1/2002 | Levene et al. | |
| 6,361,771 B1 | 3/2002 | Tao et al. | |
| 6,371,960 B2 * | 4/2002 | Heyman | A61F 2/167 606/107 |
| 6,436,427 B1 | 8/2002 | Hammang et al. | |
| 6,582,903 B1 | 6/2003 | Rigler et al. | |
| 6,627,422 B1 | 9/2003 | Li et al. | |
| 6,642,048 B2 | 11/2003 | Xu et al. | |
| 6,649,184 B2 | 11/2003 | Hammang et al. | |
| 6,667,176 B1 | 12/2003 | Funk et al. | |
| 6,669,719 B2 | 12/2003 | Wallace et al. | |
| 6,712,837 B2 | 3/2004 | Akerfeldt et al. | |
| 6,800,480 B1 | 10/2004 | Bodnar et al. | |
| 6,833,269 B2 | 12/2004 | Carpenter | |
| 6,852,527 B2 | 2/2005 | Chan et al. | |
| 6,875,607 B1 | 4/2005 | Reubinoff et al. | |
| 6,939,378 B2 | 9/2005 | Fishman et al. | |
| 6,942,873 B2 | 9/2005 | Russell et al. | |
| 6,945,984 B2 * | 9/2005 | Arumi | A61B 17/29 606/205 |
| 7,005,252 B1 | 2/2006 | Thomson | |
| 7,011,828 B2 | 3/2006 | Reubinoff et al. | |
| 7,029,913 B2 | 4/2006 | Thomson | |
| 7,037,328 B2 * | 5/2006 | Vincent | A61F 2/167 606/107 |
| 7,107,124 B2 | 9/2006 | Green | |
| 7,115,257 B1 | 10/2006 | Tao et al. | |
| 7,135,172 B1 | 11/2006 | Loftus et al. | |
| 7,141,369 B2 | 11/2006 | Cao | |
| 7,147,648 B2 | 12/2006 | Lin | |
| 7,217,569 B2 | 5/2007 | Thomson | |
| 7,250,294 B2 | 7/2007 | Carpenter | |
| 7,297,539 B2 | 11/2007 | Mandalam et al. | |
| 7,384,426 B2 | 6/2008 | Wallace et al. | |
| 7,410,798 B2 | 8/2008 | Mandalam et al. | |
| 7,413,734 B2 | 8/2008 | Mistry et al. | |
| 7,413,902 B2 | 8/2008 | Bodnar et al. | |
| 7,439,064 B2 | 10/2008 | Thomson et al. | |
| 7,455,983 B2 | 11/2008 | Xu et al. | |
| 7,504,257 B2 | 3/2009 | Reubinoff et al. | |
| 7,541,186 B2 | 6/2009 | Reh et al. | |
| 7,582,479 B2 | 9/2009 | Thomson | |
| 7,601,525 B2 | 10/2009 | Batich et al. | |
| 7,604,992 B2 | 10/2009 | Reubinoff | |
| 7,695,967 B1 | 4/2010 | Russell et al. | |
| 7,736,896 B2 | 6/2010 | Klimanskaya et al. | |
| 7,749,726 B2 | 7/2010 | Chuck | |
| 7,781,216 B2 | 8/2010 | Thomson | |
| 7,794,704 B2 | 9/2010 | Klimanskaya et al. | |
| 7,795,025 B2 | 9/2010 | Klimanskaya et al. | |
| 7,820,195 B2 | 10/2010 | Kauper et al. | |
| 7,824,671 B2 | 11/2010 | Binder et al. | |
| 7,838,727 B2 | 11/2010 | Lanza et al. | |
| 7,846,467 B2 | 12/2010 | Coroneo et al. | |
| 7,855,068 B2 | 12/2010 | Cao | |
| 7,875,296 B2 | 1/2011 | Binette et al. | |
| 7,893,315 B2 | 2/2011 | Chung et al. | |
| 7,910,369 B2 | 3/2011 | West et al. | |
| 7,914,147 B2 | 3/2011 | Sharifzadeh et al. | |
| 7,947,498 B2 | 5/2011 | Reubinoff et al. | |
| 7,959,942 B2 | 6/2011 | Cottone et al. | |
| 8,382,769 B2 * | 2/2013 | Inoue | A61F 2/167 606/107 |
| 8,425,473 B2 * | 4/2013 | Ho | A61F 9/007 604/118 |
| 8,551,088 B2 * | 10/2013 | Falkenstein | A61B 90/90 606/51 |
| 8,574,239 B2 * | 11/2013 | Ichinohe | A61F 2/167 606/107 |
| 8,603,103 B2 * | 12/2013 | Kudo | A61F 2/167 606/107 |
| 8,647,382 B2 * | 2/2014 | Kudo | A61F 2/148 623/6.12 |
| 8,808,687 B2 | 8/2014 | Humayun et al. | |
| 8,877,489 B2 | 11/2014 | Tai et al. | |
| 8,894,603 B2 * | 11/2014 | Badawi | A61F 9/0017 604/8 |
| 9,248,013 B2 | 2/2016 | Tai et al. | |
| 2002/0062136 A1 * | 5/2002 | Hillstead | A61B 17/07207 606/205 |
| 2002/0160509 A1 | 10/2002 | Reubinoff et al. | |
| 2003/0054331 A1 | 3/2003 | Fraser et al. | |
| 2003/0083646 A1 | 5/2003 | Sirhan et al. | |
| 2003/0231791 A1 | 12/2003 | Torre-Bueno et al. | |
| 2005/0031599 A1 | 2/2005 | Kooy et al. | |
| 2005/0079616 A1 | 4/2005 | Reubinoff | |
| 2005/0106554 A1 | 5/2005 | Paleck et al. | |
| 2005/0164383 A1 | 7/2005 | Reubinoff et al. | |
| 2005/0214345 A1 | 9/2005 | Leng et al. | |
| 2005/0260747 A1 | 11/2005 | Reubinoff et al. | |
| 2006/0002900 A1 | 1/2006 | Binder et al. | |
| 2006/0047306 A1 * | 3/2006 | Ortiz | A61B 17/0684 606/219 |
| 2006/0078543 A1 | 4/2006 | Reubinoff et al. | |
| 2006/0078545 A1 | 4/2006 | Carpenter | |
| 2006/0104957 A1 | 5/2006 | Yiu et al. | |
| 2006/0149194 A1 | 7/2006 | Conston et al. | |
| 2006/0234376 A1 | 10/2006 | Mistry et al. | |
| 2006/0235430 A1 | 10/2006 | Le et al. | |
| 2006/0282128 A1 | 12/2006 | Tai et al. | |
| 2007/0106208 A1 | 5/2007 | Uber et al. | |
| 2007/0212777 A1 | 9/2007 | Reubinoff | |
| 2007/0260201 A1 * | 11/2007 | Prausnitz | A61F 9/0017 604/272 |
| 2008/0243224 A1 | 10/2008 | Wallace et al. | |
| 2008/0299582 A1 | 12/2008 | Mandalam et al. | |
| 2009/0004736 A1 | 1/2009 | Reubinoff | |
| 2009/0074832 A1 | 3/2009 | Zussman et al. | |
| 2009/0075373 A1 | 3/2009 | Reubinoff et al. | |
| 2009/0104695 A1 | 4/2009 | Shushan et al. | |
| 2009/0117639 A1 | 5/2009 | Carpenter | |
| 2009/0123992 A1 | 5/2009 | Chin | |
| 2009/0130756 A1 | 5/2009 | Klann | |
| 2009/0270982 A1 | 10/2009 | Torres et al. | |
| 2009/0291495 A1 | 11/2009 | Carpenter et al. | |
| 2009/0305405 A1 | 12/2009 | Carpenter et al. | |
| 2009/0306772 A1 | 12/2009 | Tao et al. | |
| 2010/0068141 A1 | 3/2010 | Kaushal et al. | |
| 2010/0093091 A1 | 4/2010 | Reubinoff et al. | |
| 2010/0137510 A1 | 6/2010 | Seliktar et al. | |
| 2010/0144033 A1 | 6/2010 | Mandalam et al. | |
| 2010/0173410 A1 | 7/2010 | Thomson et al. | |
| 2010/0189338 A1 | 7/2010 | Lin et al. | |
| 2010/0203633 A1 | 8/2010 | Mandalam et al. | |
| 2010/0211079 A1 | 8/2010 | Aramant | |
| 2010/0241060 A1 | 9/2010 | Roizman et al. | |
| 2010/0272803 A1 | 10/2010 | Mistry et al. | |
| 2010/0299765 A1 | 11/2010 | Klimanskaya et al. | |
| 2010/0317101 A1 | 12/2010 | Mandalam et al. | |
| 2011/0004304 A1 | 1/2011 | Tao et al. | |
| 2011/0027787 A1 | 2/2011 | Chuck | |
| 2011/0046634 A1 * | 2/2011 | Rathert | A61F 2/1664 606/107 |
| 2011/0060232 A1 | 3/2011 | Lin et al. | |
| 2011/0076320 A1 | 3/2011 | Coroneo et al. | |

(56) References Cited

U.S. PATENT DOCUMENTS

| | | |
|---|---|---|
| 2011/0091927 A1 | 4/2011 | Reubinoff et al. |
| 2011/0117062 A1 | 5/2011 | Klimanskaya et al. |
| 2011/0117063 A1 | 5/2011 | Klimanskaya et al. |
| 2011/0177594 A1 | 7/2011 | Shushan et al. |
| 2011/0189135 A1 | 8/2011 | Aharonowiz et al. |
| 2011/0236464 A1 | 9/2011 | Coffey et al. |
| 2011/0256623 A1 | 10/2011 | Thomson |
| 2012/0009159 A1 | 1/2012 | Humayun |
| 2013/0137958 A1 | 5/2013 | Tai et al. |
| 2013/0143326 A1 | 6/2013 | Tai et al. |
| 2013/0144399 A1 | 6/2013 | Tai et al. |
| 2013/0190868 A1* | 7/2013 | Kahook ............... A61F 2/1648 623/6.41 |
| 2013/0296694 A1* | 11/2013 | Ehlers ................... A61B 5/065 600/424 |
| 2015/0147377 A1 | 5/2015 | Humayun et al. |
| 2015/0147810 A1 | 5/2015 | Tai et al. |
| 2016/0310637 A1 | 10/2016 | Tai et al. |

FOREIGN PATENT DOCUMENTS

| | | | |
|---|---|---|---|
| EP | 2593117 | 5/2013 | |
| EP | 2873391 A1 * | 5/2015 | ............. A61F 2/167 |
| JP | 11-009297 | 1/1999 | |
| JP | 5876045 | 1/2016 | |
| WO | WO 2005/082049 | 9/2005 | |
| WO | WO 2007/132332 | 11/2007 | |
| WO | WO 2008/098187 | 8/2008 | |
| WO | WO 2008/129554 | 10/2008 | |
| WO | WO 2009/127809 | 10/2009 | |
| WO | WO 2012/004592 | 1/2012 | |
| WO | WO 2012/009377 | 1/2012 | |
| WO | WO 2012/149468 | 11/2012 | |
| WO | WO 2012/149480 | 11/2012 | |
| WO | WO 2012/149484 | 11/2012 | |

OTHER PUBLICATIONS

U.S. Appl. No. 13/355,426, including its prosecution history, the references and the Office Actions therein, filed Jun. 6, 2013, Yu-Chong Tai et al.

U.S. Appl. No. 13/740,069, including its prosecution history, the references and the Office Actions therein, filed Jan. 11, 2013, Yu-Chong Tai et al.

U.S. Appl. No. 14/314,994, including its prosecution history, the references and the Office Actions therein, filed Jan. 11, 2013, Humayun, et al.

U.S. Appl. No. 14/498,918, including its prosecution history, the references and the Office Actions therein, filed Sep. 26, 2014, Yu-Chong Tai et al.

U.S. Appl. No. 15/004,796, including its prosecution history, the references and the Office Actions therein, filed Jan. 22, 2016, Tai et al.

Humayun et al, Biocompatible substrate for facilitating interconnections between stem cells and target tissues and methods for implanting same U.S. Appl. No. 61/481,037, filed Apr. 29, 2011, Apr. 29, 2011, Humayun et al.

"12mm Transwell with 0.4 um Pore Polyester Membrane Insert," [Online], Corning. Com, URL:http://catalog2.corning.com/Lifesciences/en-US/Shopping/PFProductDetails.aspx?productid=3460(Lifesciences)» [retrieved on Jun. 12, 2009].

Algvere et al., "Transplantation of RPE in Age-Related Macular Degeneration: Observations in Disciform Lesions and dry RPE Atrophy," Graefe's Arch Clin Exp Ophthalmol, vol. 235, Issue 3, 1997, pp. 149-158.

Armstrong et al., "The hydrodynamic radii of macromolecules and their effect on red blood cell aggregation," Biophys J., vol. 87:4259-4270 (2004).

Binder S. et al., "Transplantation the RPE in AMD," Progress in Retinal and Eye Research, vol. 26, No. 5, Sep. 2007, pp. 516-554.

Bo, Lu et al. "Semipermeable parylene membrane as an artificial bruch's membrane" 2011 16th International Solid-State Sensors, Actuators and Microsystems Conference (Transducers 2011): Beijing, China Jun. 5-9, 2011. pp. 950-953.

Deboer et al., "Multiparameter Analysis of Primary Epithelial Cultures Grown on Cycloprore Membranes," Journal of Histochemistry and Cytochemistry, vol. 42, Issue 2, 1994, pp. 277-282.

Hannachi et al., "Cell Sheet Technology and Cell Patterning for Biofabrication," Biofabrication [Online], vol. 1, No. 2, p. 022002, Jun. 10, 2009, URL:http://iopscience.iop.org/1758-5090/1/2/022002/ [Retrieved on Jul. 17, 2012].

Hsiao et al. Microfluidic system for formation of PC-2 prostate cancer co-culture spheroids, Biomaterials, vol. 30:3020-3027 (2009).

Huang, Yiming, et al. "Stem cell-based therapeutic applications in retinal degenerative diseases" Stem Cell Reviews and Reports, Humana Press Inc., NY. vol. 7, No. 2, Sep. 22, 2009, pp. 434-445.

International Search Report and Written Opinion in PCT/US2011/043747 (WO 2012/009377), dated Jul. 24, 2012.

Jackson et al., Human retinal molecular weight exclusion limit and estimate of species variation, IOVS, vol. 44:2141-2146 (2003).

Kannan R. et al., "Stimulation of Apical and Basolateral VEGF-A and VEGF-C Secretion by Oxidative Stress in Polarized Retinal Pigment Epithelial Cells," Molecular Vision, vol. 12, 2006, pp. 1649-1659.

Lavik, E. B. et al., "Fabrication of Degradable Polymer Scaffolds to Direct the Integration and Differentiation of Retinal Progenitors," Biomaterials, vol. 26, Issue 16, Jun. 2005, pp. 3187-3196.

Lee et al., Determination of human lens capsule permeability and its feasibiulity as a replacement for Bruch's membrane, Biomaterials, vol. 27:1670-1678 (2006).

Liu et al., A 3-D microfluidic combinatorial cell culture array, IEEE Proce of MEMS, Sorrento Italy, pp. 427-430 (2009).

Lu, et al., A study of the autofluorescence of parylene materials for micro-TAS applications, Lab Chip, vol. 10:1826-1834 (2010).

Lu, et al., Ultra-thin parylene-C semipermeable membranes for biomedical applications, IEEE International Micro Electro Mechanical Systems (MEMS '11) Cancun, Mexico, Jan. 23-27, 2011, pp. 505-508.

Lu, JT et al., Thin collagen film scaffolds for retinal epithelial cell culture, Biomaterials, vol. 28:1486-1494 (2007).

Neeley, W. et al., "A Microfabricated Scaffold for Retinal Progenitor Cell Grafting," Biomaterials, vol. 29, Issue 4, Feb. 2008, pp. 418-426.

Redenti, S et al., "Engineering Retinal Progenitor Cell and Scrollable poly(glycerol-sebacate) composites for Expansion and Subretinal Transplantation," Biomaterials, vol. 30, Issue 20, Apr. 9, 2009, pp. 3405-3414.

Redenti, S et al., "Retinal Tissue Engineering using Mouse Retinal Progenitor Cells and a Novel Biodegradable, Thin-Film Poly(e-caprolactone) Nanowire Scaffold," J Ocul Biol Dis Infor., vol. 1, Issue 1, May 22, 2008, pp. 19-29.

Roy, et al., Silicon nanopore membrane technology for an implantable artificial kidney, Proc. Of Tranducers, Denver Colorado, pp. 755-760 (2009).

Sodha, S. "A Microfabricated 3-D stem Cell Delivery Scaffold for Retinal Regenerative Therapy," Thesis, Master of Engineering in Biomedical Engineering, Massachusetts Institute of Technology, Jun. 2009.

Sodha, S. et al., "Microfabrication of a Three-Dimensional Polycaprolactone Thin-Film Scaffold for Retinal Progenitor Cell Encapsulation," J Biomater Sci Polym Ed., vol. 22, Issue 4-6, Jun 21, 2011, pp. 443-456.

Stanzel B. V. et al., "Culture of Human RPE from Aged Donors on a Potential Bruch's Membrane Prosthesis" Invest Ophthalmol Vis Sci, [Online] vol. 47, 2006, URL:http://abstracts.iovs.org/cgi/content/abstract/47/5/1407?maxtoshow=&HITS=10&hits=10&RESULTFORMAT=1&author1=stanzel&andorexacttitle=and&andorexacttitleabs=and&andorexactfulltext=and&searchid=I&FIRSTINDEX=O&sortspec=relevance&resourcetype=HWCIT,HWELT R> [retrieved on Jun. 12, 2009].

Stanzel et al., "Towards Prosthetic Replacement of Bruch's Membrane: Comparison of Polyester and Electrospun Nanofiber Membranes" Invest Ophthalmol Vis Sci, [Online] vol. 48, 2007, URL:http://

(56) References Cited

OTHER PUBLICATIONS abstracts.iovs.org/cgi/content/abstract/48/5/5085?maxtoshow=&HITS=10&hits=10&RESULTFORMAT=1&author1=stanzel&andorexacttitle=and&andorexacttitleabs=and&andorexactfulltext=and&searchid=1&FIRSTINDEX=0&sortspec=relevance&resourcetype=HWCIT,HWELT R> [retrieved on Jun. 12, 2009].

Tezcaner, A et al., "In Vitro Characterization of Micropatterned PLGA-PHBV8 Blend Films as Temporary Scaffolds for Photoreceptor Cells," J Biomed Mater Res vol. 86A, Issue 1, Oct. 23, 2007, pp. 170-181.

Wang, Renxin, et al. "Fabrication and characterization of a parylene-based three-dimensional microelectrode array for use in retinal prosthesis" Journal of Microelectromechanical Systems, IEEE Service Center, US, vol. 19, No. 2, Apr. 1, 2010 pp. 367-374.

Australian Office Action dated Jul. 17, 2015 for AU 2015200823.

Lu, Bo et al., "A 3-D parylene scaffold cage for culturing retinal pigment epithelial cells," Micro Electro Mechanical Systems (MEMS), 2012, Paris, Italy, pp. 741-744.

Lu, Bo et al., "Mesh-supported submicron parylene-C membranes for culturing retinal pigment epithelial cells," Biomed Microdevices, 202, vol. 14, pp. 659-667.

IPRP and Written Opinion of the International Search Authority in PCT/US2011/043747 (WO 2012/009377), dated Jan. 15, 2013.

Australian Office Action dated Jul. 5, 2013 for AU 2011279250.

Extended European Search Report dated Dec. 5, 2013 for EP 11 80 7411.

JP Office Action dated Jun. 8, 2015 for JP 2013-519773.

IPRP and Written Opinion of the International Search Authority in PCT/US2012/035654, dated Nov. 7, 2013.

Chong, N.H. Victor et al. Management of inherited outer retinal dystrophies: present and future. Br J Ophthalmol 1999:83:120-122.

G. J. Morris, et al. "Cryopreservation of murine embryos, human spermatozoa and embryonic stem cells using a liquid nitrogen-free, controlled rate freezer." Reproductive BioMedicine Online, Jun. 23, 2006, vol. 13 (3), pp. 421-426, ISSN 1472-6483.

Nazare Pereira-Rodrigues, et al. "Modulation of hepatocarcinoma cell morphology and activity by parylene-C coating on PDMS." In: PLoS ONE. Mar. 2010, vol. 5(3), p. e9667, Issn 1932-6203.

Tracy Y. Chang, et al. "Cell and protein compatibility of Parylene-C surfaces." In: Langmuir, 2007, vol. 23(23), pp. 11718-11725, ISSN 0743-7463.

International Search Report and Written Opinion for PCT/US2012/035654, dated Oct. 29, 2012.

U.S. Appl. No. 15/184,934, including its prosecution history, the references and the Office Actions therein, filed Jun. 16, 2016, Tai et al.

European Office Action dated Jul. 5, 2016 for EP 11 807 411.

\* cited by examiner

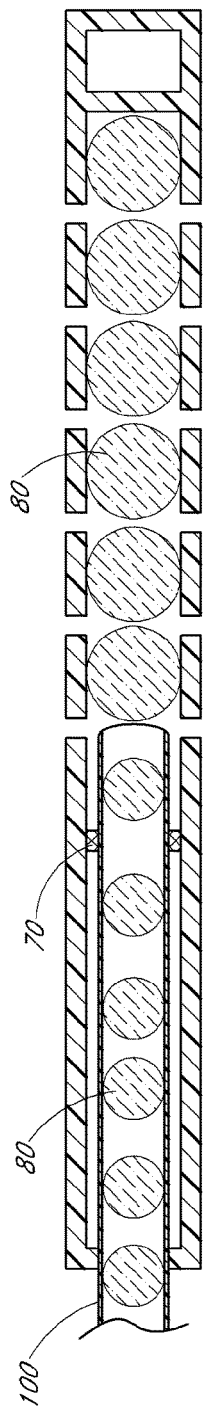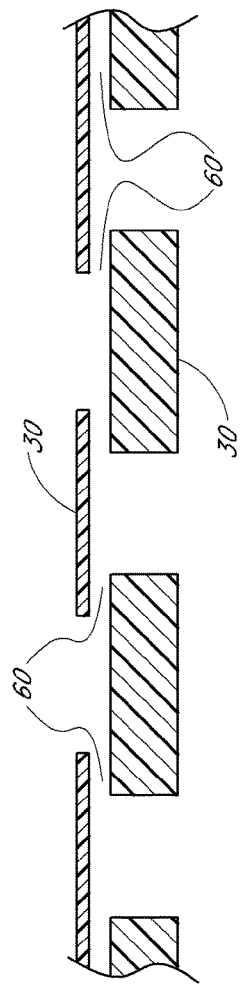

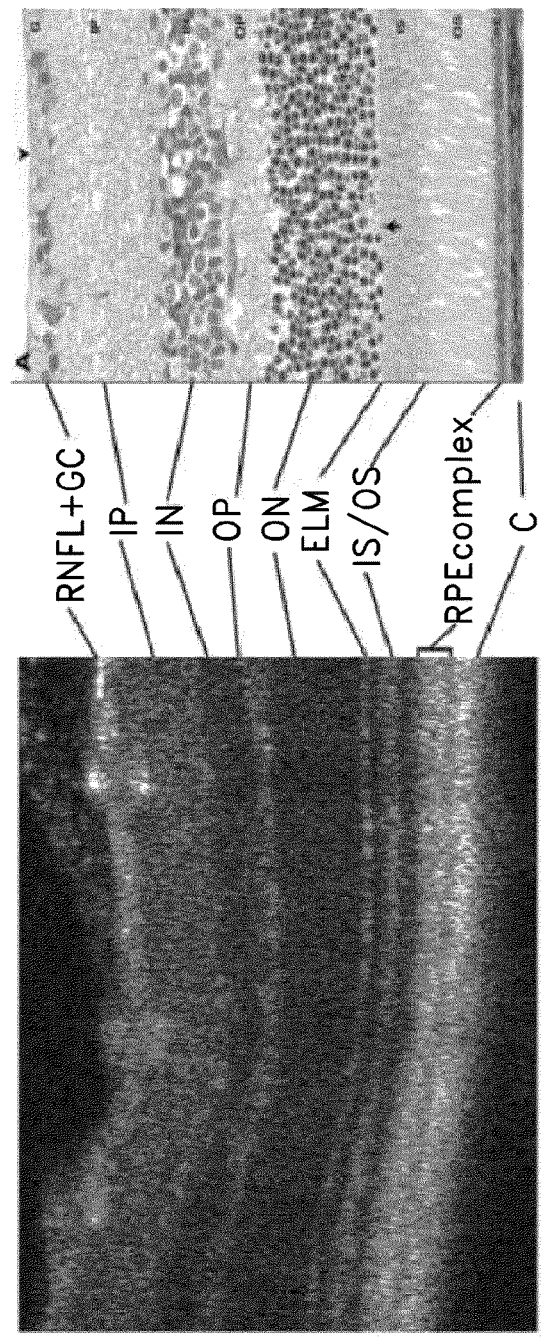

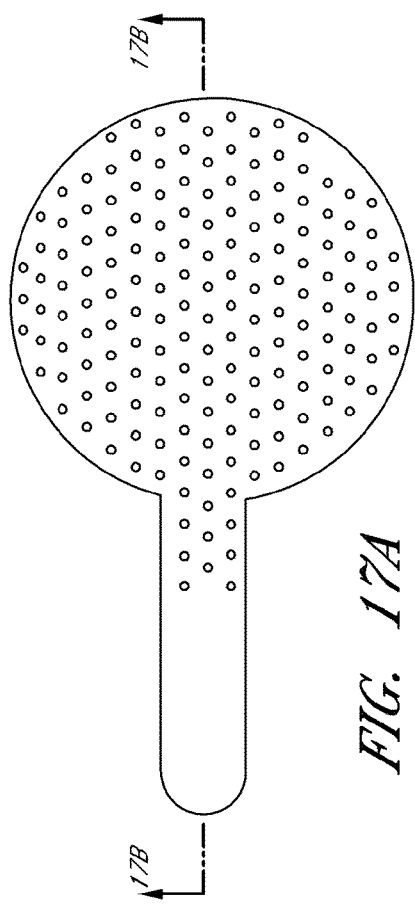
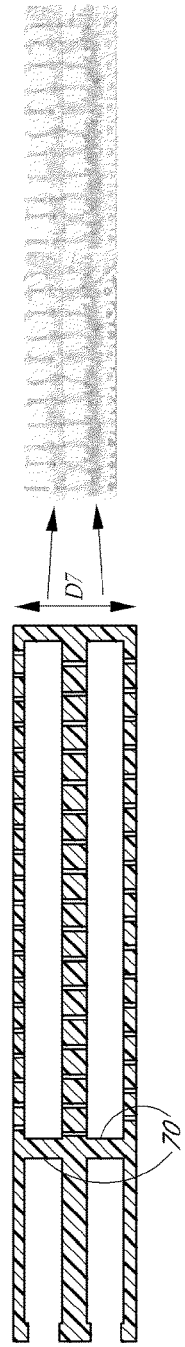
FIG. 17A
FIG. 17B

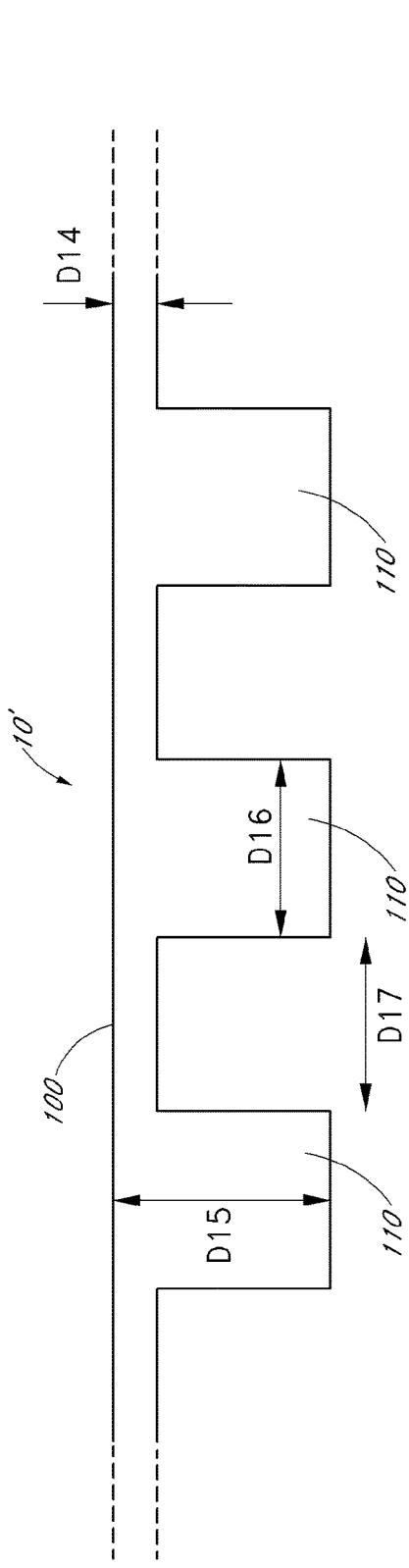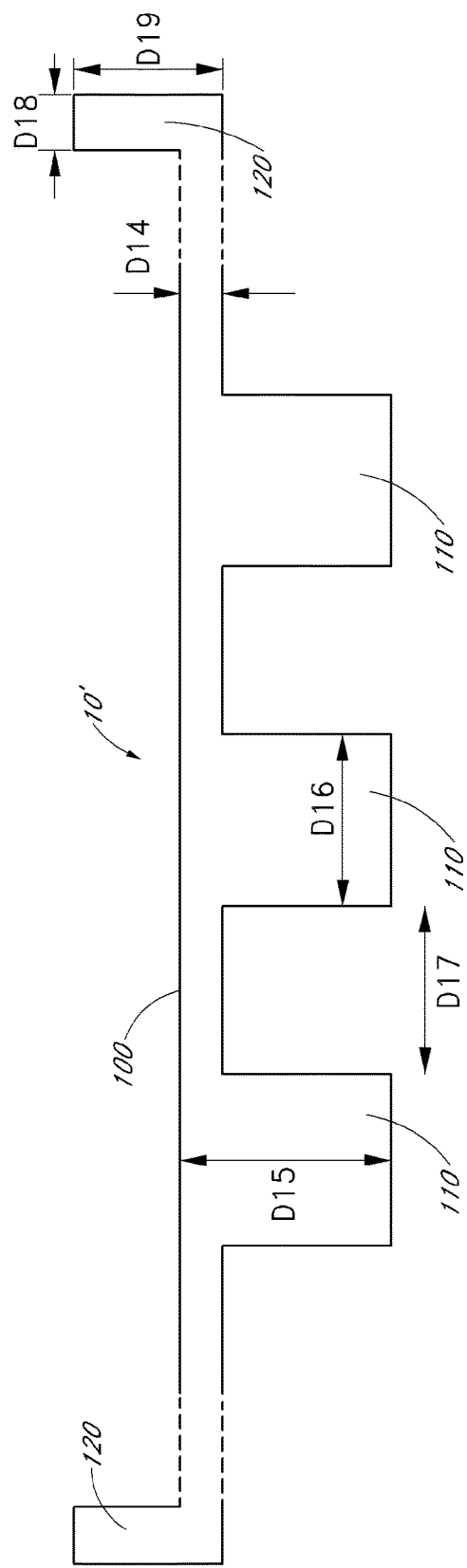

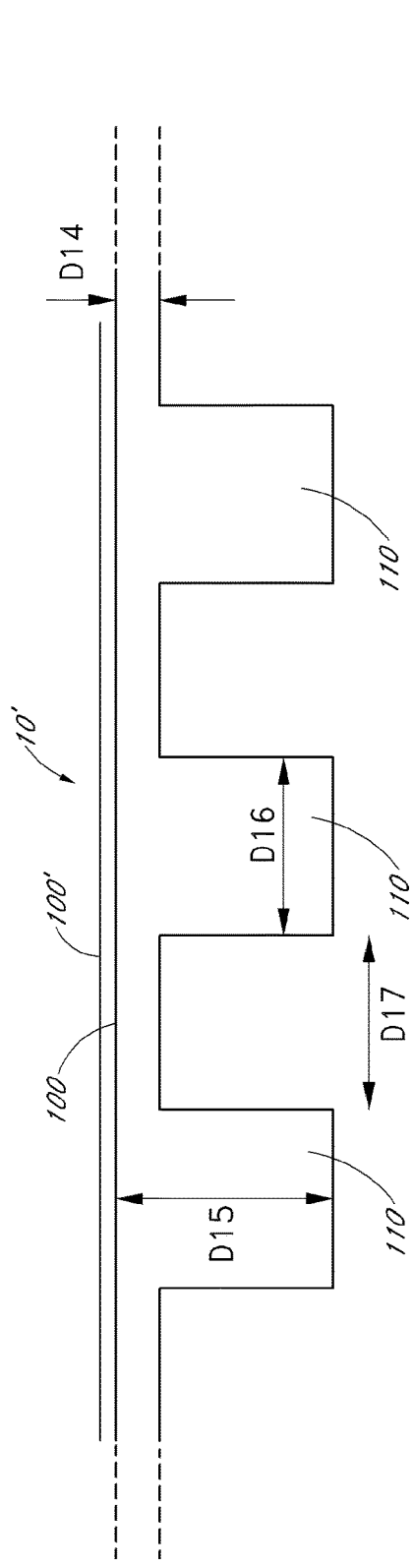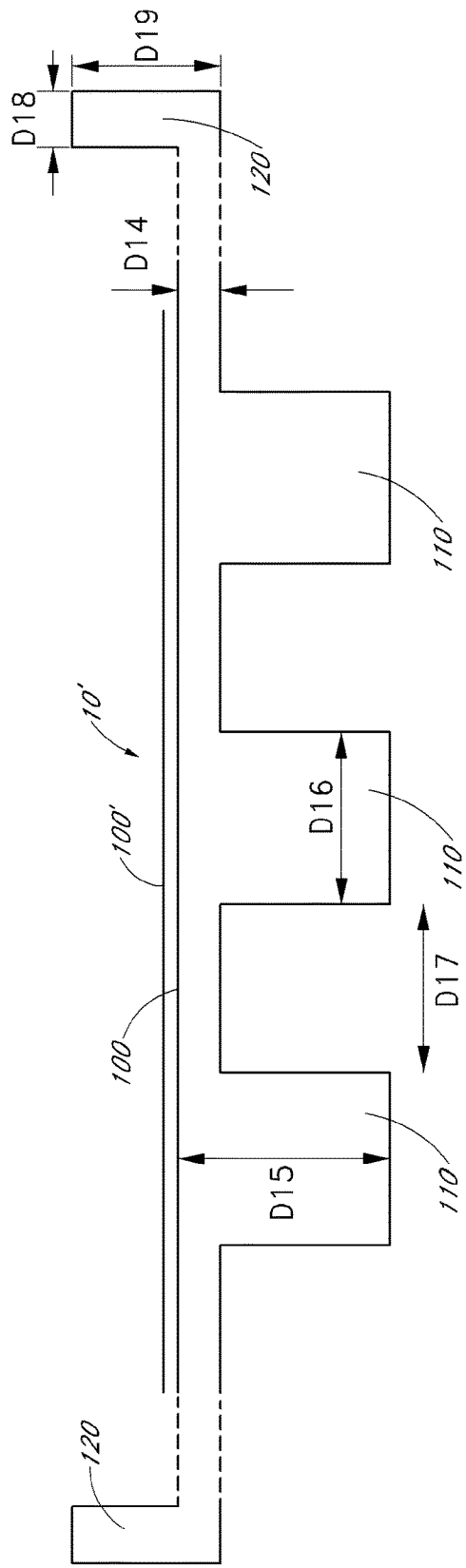

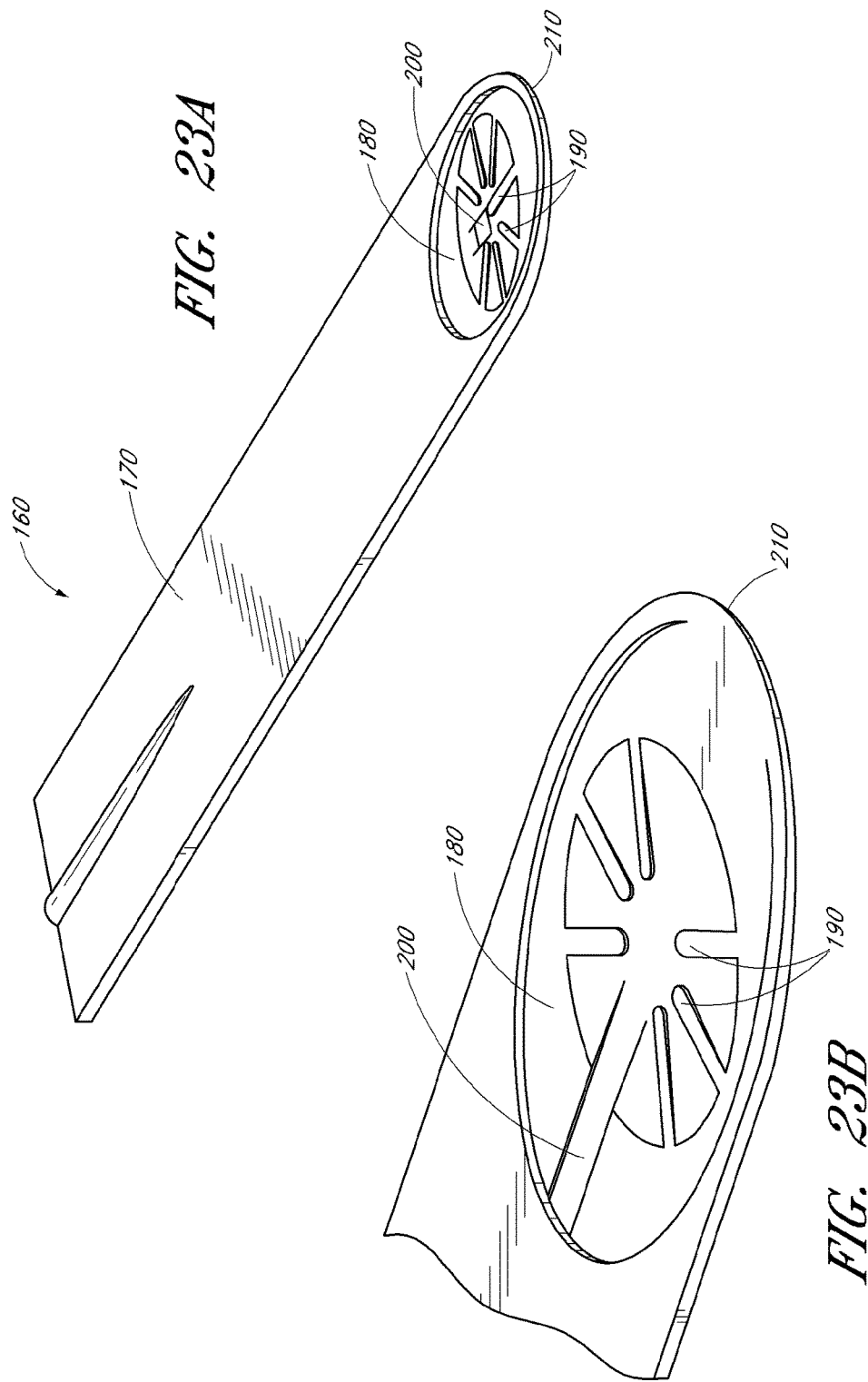

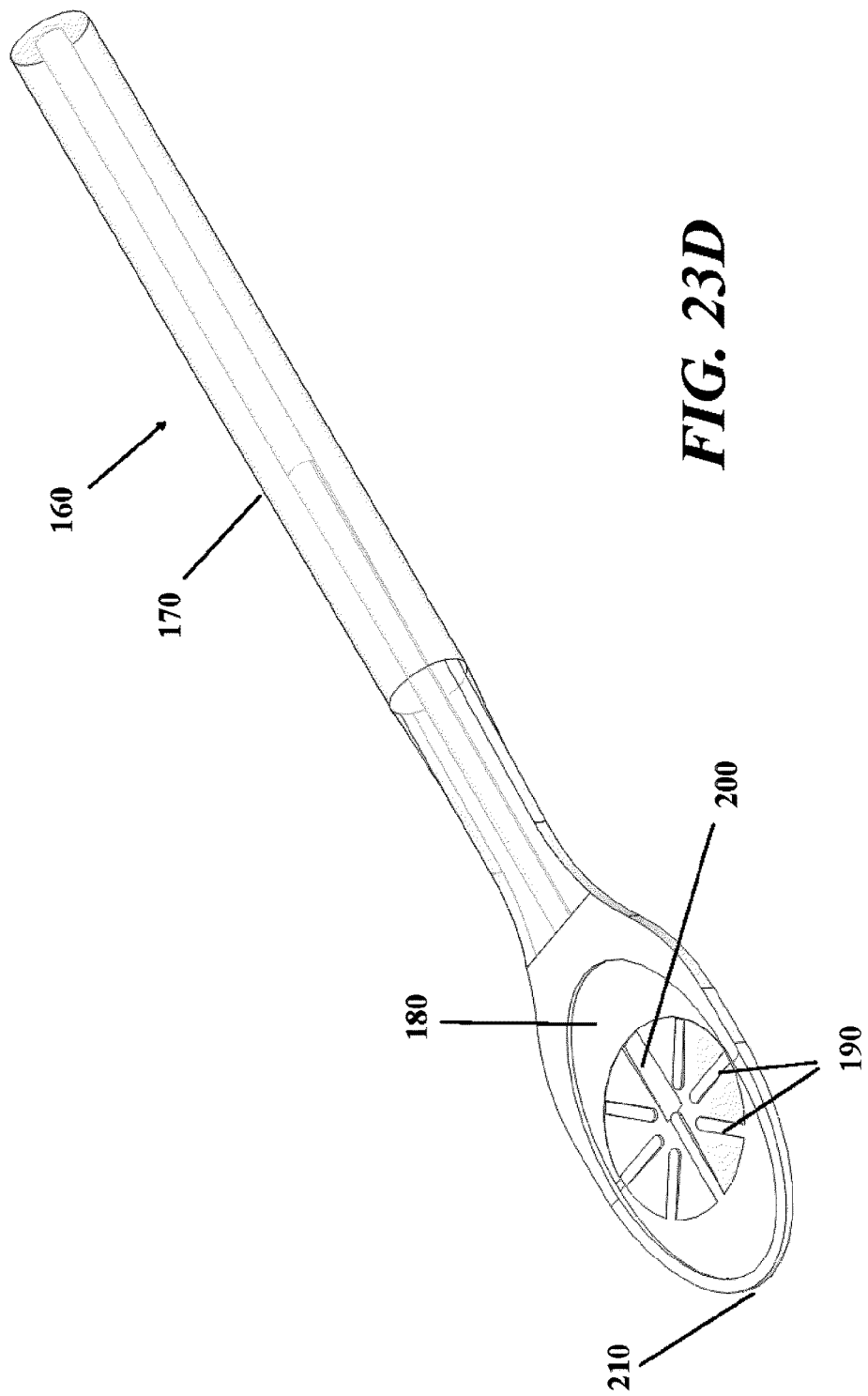

A  B  C

A

B

A

B

Post Implant Day 9

FIG. 40 Post Implant Day 58

Post Implant Day 58

INSTRUMENTS AND METHODS FOR THE IMPLANTATION OF CELL-SEEDED SUBSTRATES

RELATED CASES

This Application is the U.S. National Phase application under 35 U.S.C. § 371 of International Application No. PCT/US2012/035654, filed Apr. 27, 2012, which claims the benefit of U.S. Provisional Application Ser. Nos. 61/481,037, filed on Apr. 29, 2011 and 61/591,808, filed on Jan. 27, 2012, the contents of each of which are expressly incorporated in their entireties by reference herein.

BACKGROUND

Field of the Invention

The present application relates generally to instruments and methods for the implantation of substrates into target tissues, the substrates being suitable for seeding with stem cells for stem cell therapy.

Description of the Related Art

The scope of human disease that involves loss of or damage to cells is vast and includes, but is not limited to, ocular disease, neurodegenerative disease, endocrine diseases, cancers, and cardiovascular disease. Cellular therapy involves the use of cells, and in some cases stem cells to treat diseased or damaged tissues. It is rapidly coming to the forefront of technologies that are poised to treat many diseases, in particular those that affect individuals who are non-responsive to traditional pharmacologic therapies.

In fact, many diseases that are candidates for application of cellular therapy are not fatal, but involve loss of normal physiological function. For example, ocular diseases often involve functional degeneration of various ocular tissues which affects the vision, and thus the quality of life of numerous individuals.

The mammalian eye is a specialized sensory organ capable of converting incoming photons focused by anterior optics (cornea and lens) into a neurochemical signal. This process of phototransduction allows for sight by sending action potentials to higher cortical centers via the optic nerve. The retina of the eye comprises photoreceptors that are sensitive to various levels of light and interneurons that relay signals from the photoreceptors to the retinal ganglion cells. These photoreceptors are the most metabolically active cells in the eye (if not the body), and are supported metabolically and functionally by retinal pigmented epithelial cells (RPE). These RPE are positioned in a monolayer in the eye and are critical to vision.

Numerous pathologies can compromise or entirely eliminate an individual's ability to perceive visual images, including trauma to the eye, infection, degeneration, vascular irregularities, and inflammatory problems. The central portion of the retina is known as the macula, which is responsible for central vision, fine visualization and color differentiation. The function of the macula may be adversely affected by age related macular degeneration (wet or dry), diabetic macular edema, idiopathic choroidal neovascularization, high myopia macular degeneration, or advanced retinitis pigmentosa, among other pathologies.

Age related macular degeneration typically causes a loss of vision in the center of the visual field (the macula) because of damage to the retina. It is a major cause of visual impairment in older adults (>50 years). Macular degeneration occurs in "wet" and "dry" forms. In the dry form, cellular debris (drusen) accumulates between the retina and the choroid, the blood supply of the outer retina, which puts pressure on the retina, possibly leading to retinal detachment and loss of vision. In the more severe wet form, newly formed blood vessels from the choroid infiltrate the space behind the macula, which causes death of photoreceptors and their supporting cells. In conjunction with the loss of functional cells in the eye, the newly formed blood vessels are fragile and often leak blood and interstitial fluid, which can further damage the macula.

While diseases that cause damage to specific cells or tissues are clear candidates for cellular therapy, there remains a need in the art for methods, substrates, and tools to improve the efficacy of cellular therapy.

SUMMARY

In several embodiments, there is provided an instrument for the implantation of a substrate for transplanting (or subsequent seeding with a biological tissue, such as cells) into a target tissue of a subject, comprising a handpiece comprising a proximal end and a distal end, the distal end comprising an orifice, a distal outer housing extending in a distal direction from said handpiece, an internal shaft having a proximal end and a distal end and configured to be longitudinally moveable within the distal outer housing and said handpiece, and wherein the distal-most portion said internal shaft comprises forceps, a shaft movement control mechanism, wherein activation of the movement control mechanism causes longitudinal movement of the internal shaft, wherein movement of the internal shaft in a proximal direction causes the distal-most portion of said internal shaft to retract within the distal-most portion of the distal outer housing, and wherein the retraction thereby causing said forceps to close, and wherein movement of the internal shaft in a distal direction causes the distal-most portion of the internal shaft to extend beyond the distal-most portion of the distal outer housing thereby causing the forceps to open.

In several embodiments, the opening or closure of the forceps results in the respective release or grasping of a substrate. In several embodiments, the substrate is suitable for seeding with cells. In some embodiments, the substrate is suitable for seeding with stem cells. In several embodiments, the stem cells are RPE cells, precursors thereof, or derivatives thereof. In other embodiments, the substrate is suitable for seeding with one or more of corneal endothelial or epithelial cells, trabecular meshwork cells, precursors thereof, or derivatives thereof. In still additional embodiments, the substrate is suitable for seeding with one or more of chondroblasts, cardiac cells, precursors thereof, or derivatives thereof.

In several embodiments, the forceps comprise two tines movable in opposite directions relative to one another. In other embodiments, the forceps comprise movable tine and one fixed tine.

In several embodiments, the movement control mechanism comprises a slide mechanism. In several embodiments, the movement control mechanism comprises a friction wheel mechanism. In several embodiments, the movement control mechanism comprises one or more racks associated with the forceps and a gear mechanism that interacts with the racks. In still additional embodiments, combinations of such control mechanisms are used. In several embodiments, the movement control mechanism comprises a gross movement control mechanism and a fine movement control mechanism.

In several embodiments, the instrument further comprises a reversibly releasable retaining mechanism to maintain the internal shaft in a retracted position. In several embodiments, the reversibly releasable retaining mechanism comprising a retaining spring and switch.

In several embodiments, the instrument further comprises an injection pathway. In several embodiments, the injection pathway is configured to deliver a media from the handpiece to a target site at or near the distal-most portion of the internal shaft. In several embodiments, the media comprises a physiologically compatible substance. In some embodiments, the target tissue is ocular tissue and the media is perflurocarbon. In several embodiments, the target tissue is selected from the group consisting of ocular tissue, cartilage, and cardiac tissue and the media is a bioadhesive. In several embodiments, the bioadhesive functions to assist in implanting the substrate by adhering the substrate (either temporarily or permanently) onto the host tissue.

In several embodiments, the forceps are configured to reversibly interact with a substrate. In some embodiments, the substrate is substrate is seeded with stem cells. In some embodiments, the stem cells are RPE cells.

In additional embodiments, the forceps are configured to reversibly interact with a substrate support platform. In several embodiments, the substrate support platform is suitable for supporting a substrate. In some embodiments, after interacting with a substrate support platform, proximal longitudinal movement of the movement control mechanism causes retraction of the inner shaft resulting in contact between the outer edges of the substrate support platform and the inner portion of the outer housing, thereby inducing the substrate support platform to roll into a cylindrical shape. In some embodiments, distal longitudinal movement of the movement control mechanism causes the outer edges of the substrate support platform to move distally beyond the outer housing, thereby allowing the rolled support platform and the unroll. In several embodiments, the substrate is cell-seeded, and wherein the cell-seeded substrate rolls in conjunction with the substrate support, but to a degree that does not allow the cell-seeded surfaces to roll onto one another.

In several embodiments, there is also provided an instrument for the implantation of a substrate into a target tissue of a subject, comprising a handpiece comprising a proximal end and a distal end, a distally positioned substrate supporting platform comprising an apical and basal side and a shaft configured to couple said handpiece to said substrate supporting platform.

In several embodiments, the substrate supporting platform functions to provide a "resting place" for the substrate during the implantation process. In several embodiments, the substrate supporting platform comprises a plurality of substrate barriers on the apical side of the platform. Taken together, such barriers provide a region in which a substrate (either pre-seeded with cells or ready to be seeded) is positioned and protected during the process of implantation into a target tissue. In several embodiments, the protection is from the shear forces that the substrate is exposed during implantation (e.g., the flow of blood or ocular fluid across the implant). In several embodiments, the substrate is protected by the barriers from the contact with tissues that surround the target implantation site. In some embodiments, the barriers are positioned at or near the lateral edges of the platform, in order to accommodate a substrate of a certain desired size. In other embodiments, the barriers are positioned in such a way as to accommodate an irregularly shaped implant. In several embodiments, the barriers facilitate the reversible placement of the implant (e.g., the barriers provide protection but allow the removal of the substrate when at the target tissue with minimal difficulties). In some embodiments, the barriers are formed during the formation of the platform, while in some embodiments, they are formed separately and attached to the platform. In several embodiments, the barriers range from about 5 microns to about 50 microns in height, while in other embodiments, they may be larger or smaller, depending on the dimensions of the substrate to be positioned on the platform. In several embodiments, said platform comprises parylene. In several embodiments, the barriers also comprise parylene. In other embodiments, the barriers are made of a different material. For example, in one embodiment, the barriers comprise a rapidly biodegradable material, such that, the barriers provide the necessary protection for the substrate during implantation, but as the process of implantation continues, the barriers biodegrade (in whole or in part), thus allowing the surgeon to simply slide the substrate off of the platform and into the target site.

In several embodiments, the instrument is fabricated in whole or in part from a thermoplastic polymer. In additional embodiments, the instrument is fabricated, in whole or in part, from metal. In some embodiments, combinations of materials (e.g., plastic and metal) are used.

There is also provided herein a method of treating a subject having outer retinal degenerative disease, comprising surgically positioning an substrate in a position juxtaposed to the outer nuclear layer of the photoreceptors in the eye of the subject, wherein the substrate comprises a non-porous polymer, wherein the substrate comprises a substantially homogeneous apical surface for the growth of RPE cells, wherein the thickness of the substantially homogeneous apical surface ranges from about 0.2 to about 4 microns, wherein the substrate comprises an inhomogeneous basal surface comprising supporting features juxtaposed with the substantially homogeneous apical surface, wherein the height of the supporting features ranges from about 3 µm to about 150 µm, wherein the substrate is configured to support a population of RPE cells suitable for the treatment of diseased or damaged ocular tissue, and wherein the RPE cells support the photoreceptors, thereby treating the degenerative disease.

In several embodiments the surgical positioning is performed using a instrument comprising a handpiece comprising a proximal end and a distal end, the distal end comprising an orifice, a distal outer housing extending in a distal direction from the handpiece, an internal shaft having a proximal end and a distal end and configured to be longitudinally moveable within the distal outer housing and the handpiece, wherein the distal-most portion the internal shaft comprises forceps, and a shaft movement control mechanism, wherein activation of the movement control mechanism causes longitudinal movement of the internal shaft, wherein movement of the internal shaft in a proximal direction causes the distal-most portion of the internal shaft to retract within the distal-most portion of the distal outer housing, wherein the retraction thereby causing the forceps to close, and wherein movement of the internal shaft in a distal direction causes the distal-most portion of the internal shaft to extend beyond the distal-most portion of the distal outer housing thereby causing the forceps to open.

There is also provided in additional embodiments, a method for the treatment of an outer retinal degenerative disease, comprising positioning a substrate in a target position juxtaposed to the outer nuclear layer of the photoreceptors in the eye of a subject having the outer retinal degenerative disease, wherein the positioning comprises grasping the substrate using any of the instruments of described herein by movement of the movement control mechanism in a proximal direction, maneuvering the distal portion of the instrument through an incision in the sclera of the subject and to the target position, releasing the substrate from the instrument by movement of the movement control mechanism in a distal direction, removing the instrument from the eye of the subject; and closing the incision. In several embodiments, the substrate comprises, a permeable polymer, wherein the substrate comprises a substantially homogeneous apical surface for the growth of RPE cells, wherein the thickness of the substantially homogeneous apical surface ranges from about 0.2 to about 4 microns, wherein the substrate comprises an inhomogeneous basal surface comprising supporting features juxtaposed with the substantially homogeneous apical surface, and wherein the height of the supporting features ranges from about 3 μm to about 150 μm. In several embodiments, the permeable polymer is selected from the group consisting of parylene A, parylene AM, parylene C, ammonia and/or oxygen treated parylene C. In several embodiments, the substrate is coated with one or more of polydopamine, vitronectin, retronectin, matrigel, or combinations thereof. In several embodiments, the substrate comprises parylene C. In several embodiments, the substrate is seeded with RPE cells in vitro. In other embodiments, is seeded with RPE cells in vivo after the positioning. In several embodiments wherein the substrate is seeded in vivo, the substrate is optionally coated with vitronectin.

There is also provided a method for the treatment of an outer retinal degenerative disease, comprising, at a first timepoint, positioning a substrate in a target position juxtaposed to the outer nuclear layer of the photoreceptors in the eye of a subject having the outer retinal degenerative disease, wherein the positioning comprises grasping the substrate with an instrument comprising a handpiece comprising a proximal end and a distal end, the distal end comprising an orifice, a distal outer housing extending in a distal direction from the handpiece, an internal shaft having a proximal end and a distal end and configured to be longitudinally moveable within the distal outer housing and the handpiece, and wherein the distal-most portion the internal shaft comprises forceps, a shaft movement control mechanism, wherein activation of the movement control mechanism causes longitudinal movement of the internal shaft, wherein movement of the internal shaft in a proximal direction causes the distal-most portion of the internal shaft to retract within the distal-most portion of the distal outer housing, wherein the retraction thereby causing the forceps to close, and wherein movement of the internal shaft in a distal direction causes the distal-most portion of the internal shaft to extend beyond the distal-most portion of the the distal outer housing thereby causing the forceps to open, maneuvering the distal portion of the instrument through an incision in the sclera of the subject and to the target position, releasing the substrate from the instrument by movement of the movement control mechanism in a distal direction, removing the instrument from the eye of the subject; and at a second timepoint, seeding the positioned substrate with stem cells.

In several embodiments, the first time point and the second time point occur during the same surgical procedure. However, in other embodiments, the first time point and the second time point occur during separate surgical procedures. In such embodiments, the separate surgical procedures are separated by at least about 24 to about 48 hours.

There is additionally provided a method for the treatment of an outer retinal degenerative disease, comprising at a first timepoint, positioning an RPE cell-seeded substrate in a target position juxtaposed to the outer nuclear layer of the photoreceptors in the eye of a subject having the outer retinal degenerative disease, wherein the positioning comprises grasping the substrate with an instrument comprising, a handpiece comprising a proximal end and a distal end, the distal end comprising an orifice, a distal outer housing extending in a distal direction from the handpiece, an internal shaft having a proximal end and a distal end and configured to be longitudinally moveable within the distal outer housing and the handpiece, wherein the distal-most portion the internal shaft comprises forceps, and a shaft movement control mechanism, wherein activation of the movement control mechanism causes longitudinal movement of the internal shaft, wherein movement of the internal shaft in a proximal direction causes the distal-most portion of the internal shaft to retract within the distal-most portion of the distal outer housing, wherein the retraction thereby causing the forceps to close; and wherein movement of the internal shaft in a distal direction causes the distal-most portion of the internal shaft to extend beyond the distal-most portion of the the distal outer housing thereby causing the forceps to open, maneuvering the distal portion of the instrument through an incision in the sclera of the subject and to the target position, releasing the substrate from the instrument by movement of the movement control mechanism in a distal direction; and removing the instrument from the eye of the subject.

There is also provided a method for the treatment of an outer retinal degenerative disease comprising positioning an RPE cell-seeded substrate in a target position juxtaposed to the outer nuclear layer of the photoreceptors in the eye of a subject having the outer retinal degenerative disease.

There is also provided a method for the treatment of an outer retinal degenerative disease, comprising, at a first timepoint, positioning a substrate in a target position juxtaposed to the outer nuclear layer of the photoreceptors in the eye of a subject having the outer retinal degenerative disease and at a second timepoint, seeding the positioned substrate with stem cells.

Many tissues are structurally or functionally dynamic in that the tissues flex during normal function, are subject to fluid flow or other shear stresses, or have numerous specialized cell types in close juxtaposition, thereby limiting the selection of target sites for cell delivery. As such, cellular therapy can require specific devices and methods to administer cells to a target tissue that enhance the activity and beneficial effects of the administered cells at the target tissue for an extended period of time.

In several embodiments, there is provided a substrate for cellular therapy to treat diseased or damaged ocular tissue comprising a non-porous polymer having a roughened apical surface topology for the growth of cells and an inhomogeneous basal surface comprising supporting features juxtaposed with the roughened apical surface topology, wherein the substrate is configured to support a population of cells suitable for the treatment of diseased or damaged ocular tissue, and wherein, upon implantation into a subject, the substrate supports the population of cells for a period of time sufficient to treat the diseased or damaged ocular tissue. In several embodiments, the substrate is fabricated in a substrate frame comprising a plurality of substrates.

In some embodiments, the thickness of the substantially homogeneous apical surface ranges from about 0.1 to about 4 microns. In several embodiments, the thickness of the substantially homogeneous apical surface for the growth of cells prohibits passage of proteins larger than about 75 kDa through the substrate. In some embodiments, the substantially homogeneous apical surface further comprises a raised lip surrounding the surface. In some such embodiments, the raised lip has a height ranging from about 10 to about 1000 microns and a width ranging from about 10 to about 1000 microns. Other embodiments do not have a lip. In some embodiments, the height of the supporting features ranges from about 3 µm to about 150 µm.

In several embodiments, the non-porous polymer is non-biodegradable while in other embodiments, the non-porous polymer is biodegradable. In some embodiments, the biodegradable polymer comprises polyethylene glycol modified polycaprolactone, PLGA, gelatin-modified silicone, or an anhydride polymer.

In several embodiments, the non-porous polymer is selected from the group consisting of parylene A, parylene AM, parylene C, ammonia and/or oxygen treated parylene C (for the purposes of adding functional groups and roughening the surface), and parylene C treated with either polydopamine, vitronectin, retronectin, or matrigel. While parylene may not traditionally be considered permeable, in several embodiments, the dimensions of substrates constructed of parylene (e.g., the thinness of the substrate) confer permeability on the material. In one embodiment, the non-porous polymer comprises parylene AM treated with polydopamine, and the inhomogeneous basal surface comprises parylene. In one embodiment, the substrate is configured to support a population of retinal pigmented epithelial (RPE) cells. In one embodiment, the retinal pigmented epithelial cells are human embryonic stem cell-derived RPE cells.

In several embodiments, the substrate is seeded on its substantially homogeneous apical surface with cells selected from the group consisting of: RPE cells, RPE and photoreceptors, Müller glial cells, ganglion cells, a mixture of Müller glial cells and ganglion cells, corneal endothelial cells, a mixture of corneal endothelial cells and collagen, corneal epithelial cells, a mixture of corneal epithelial cells and collagen, endothelial cells, pericytes, a mixture of endothelial cells and pericytes.

In several embodiments, the cell-seeded substrate is implanted in the subretinal space of the eye of a subject. In several such embodiments, the RPE cells interdigitate with the outer segments of the photoreceptors of the eye of the subject. In some embodiments, the RPE cells interdigitate with the outer nuclear layer of the photoreceptors.

In some embodiments, the cell-seeded substrate is implanted adjacent to the epiretinal side of the retina of the eye of a subject.

In some embodiments, the cell-seeded substrate is implanted adjacent to corneal tissue of the eye of a subject.

In several embodiments, the cell-seeded substrate is suitable for cellular therapy for treatment of dry AMD, for treatment of corneal disease, for treatment of glaucoma, for treatment of diabetic retinopathy, for treatment of retinal vein occlusions, for treatment of wet AMD, and/or for treatment of retinitis pigmentosa. Other ocular diseases may also be treated with such substrates.

In several embodiments, there is provided a substrate for preparing cells for cellular therapy to treat diseased or damaged ocular tissue comprising a non-porous polymer comprising a substantially homogeneous apical surface for the growth of cells in an interconnected monolayer of cells, wherein prior to delivery to a subject, the interconnected monolayer of cells is detached from the substrate and the monolayer is implanted in said subject, thereby treating said diseased or damaged ocular tissue.

In several embodiments, there is provided a substrate for cellular therapy to treat diseased or damaged ocular tissue comprising a non-porous, permeable, non-biodegradable polymer selected from the group consisting of parylene A, parylene AM, ammonia etched parylene, and parlyene coupled with polydopamine configured to form a roughened apical surface for the growth of cells, wherein said substantially homogeneous apical surface is coated with one or more of cyclic or linear arginine-glycine-aspartic acid or a synthetic growth matrix, and an inhomogeneous basal surface comprising supporting features juxtaposed with said substantially homogeneous apical surface. In several embodiments, said substrate is configured to support a population of cells suitable for the treatment of diseased or damaged ocular tissue and, upon implantation into a subject, said substrate supports said population of cells for a period of time sufficient to treat said diseased or damaged ocular tissue. In some embodiments, wherein the thickness of said substantially homogeneous apical surface ranges from about 0.1 to about 6 microns, and the height of said supporting features ranges from about 3 µm to about 150 µm.

In several embodiments there is provided a system for preparing a substrate for cellular therapy, comprising: a polymeric substrate frame comprising a plurality of individual substrates and a device for temporarily maintaining the substrate frame in a fixed position within a culture vessel.

In several embodiments said individual substrates are capable of being removed individually from the substrate frame. In some embodiments, said device is configured to prevent growth of cells on at least one portion of each of the plurality of individual substrates, and some embodiments said device is configured to allow selective removal of an individual substrate from the substrate frame.

In several embodiments, the system further comprises a tool for implanting an individual substrate into the eye of a subject. In some embodiments, said implantation tool comprises a handle, a recessed portion configured to hold said individual substrate, and one or more supporting features within said recessed portion configured to provide mechanical stability to said individual substrate. In other embodiments, said implantation tool comprises a conical funnel having a substrate loading port and an exit port, a plunger for pushing a cell-seeded substrate through said exit port and into a target tissue, wherein the funnel shape of the tool facilitates the rolling of said cell-seeded substrate without overlap of the edges of the substrate.

In several embodiments there is provided a tool for the implantation of a cell-seeded substrate into the eye of a subject, wherein the tool comprises a proximal handle, a lumen within said proximal handle, an internal shaft, a sliding control, and a distal outer housing. In some embodiments, the lumen is dimensioned to house said internal shaft, which is longitudinally moveable within said lumen. The movement of the shaft is controlled by activation of said sliding control. In several embodiments, movement of said internal shaft in a distal direction causes the end of said shaft to extend beyond the distal-most portion of the outer housing. In several embodiments the tool further comprises a retention spring configured to hold said internal shaft in a proximal position. In several embodiments, the distal-most portion of said internal shaft is configured to reversibly interact with a substrate support platform. In several embodiments the substrate support platform is suitable for supporting a cell-seeded implant.

In several embodiments, after a substrate support platform comprising a cell-seeded substrate is reversibly connected to the distal end of the shaft, proximal longitudinal movement of the slider control causes the outer edges of the substrate support platform to come into contact with the inner portion of the outer housing, thereby inducing the substrate support platform and the cell-seeded implant positioned thereon to roll into a cylindrical shape. The rolling is sufficient to protect the cells on the substrate from shear forces, but not to the degree where the rolled substrate support platform and the substrate overlap onto themselves or one another.

In several embodiments, after the substrate support platform and the substrate are rolled, distal longitudinal movement of the slider control causes the outer edges of the substrate support platform to move distally beyond the outer housing, thereby allowing the rolled substrate support platform and the substrate to unroll, thereby exposing the cell-seeded substrate. After such movement (which occurs once the distal end of the tool is near the ultimate implant site, the substrate is positioned for removal from the tool and positioning at the ultimate implant site.

In some embodiments of the system, said polymeric substrate frame and said individual substrates comprises a non-biodegradable polymer while in other embodiments, said polymeric substrate frame and said individual substrates comprises a biodegradable polymer.

In several embodiments said substrates are removed by cutting a portion of the substrate that connects the substrate to the substrate frame. Advantageously, several embodiments of said device configured to prevent growth of cells comprises an aperture through which said portion of said substrate can be cut.

In several embodiments, there is provided a tool for the implantation of a cell-seeded substrate into the eye of a subject comprising a handle, a recessed portion, a port for transmitting negative pressure to an substrate residing within said recessed portion, and one or more supporting features within said recessed portion, wherein said supporting features provide mechanical stability to a substrate residing within the recessed portion of the device.

In some embodiments, the depth of said recessed portion is between about 15 µm and about 500 µm. In some embodiments, outer diameter of said recessed portion is between about 1 and about 10 mm or between about 2 and about 5 mm. In some embodiments, the inner diameter of said recessed portion is between about 0.5 and about 7 mm or between about 1.5 and about 5.5 mm. In some embodiments, the height of said supporting features is between about 15 µm to about 400 µm and in some embodiments, the width of said supporting features is between about 15 µm to about 400 µm.

In some embodiments, of the tool, said negative pressure is negative gas pressure while in other embodiments, said negative pressure is fluid pressure. In some embodiments, said port in the tool is further suitable for transmitting positive pressure to an implant residing within said recessed portion resulting in displacement of said substrate from said recessed portion. In some embodiments, a pressure regulator is used.

In some embodiments, the wall of the recessed portion has an angle of between about 5 degrees and about 40 degrees, as measured from the floor of the recessed portion while in other embodiments, the wall of the recessed portion has an angle of between about 12 degrees and about 16 degrees, as measured from the floor of the recessed portion.

In some embodiments, the distal-most portion of the device is suitable for cutting ocular tissue while in other embodiments, the device is configured for attachment to a standard device for cutting ocular tissue.

In several embodiments, the tool is fabricated from a thermoplastic polymer while in other embodiments for example, parylene, while in other embodiments, the tool is fabricated from metal.

In several embodiments there is provided a tool for the implantation of a cell-seeded substrate into the eye of a subject comprising a cylindrical proximal end that is funnel shaped, a substrate passageway and a cylindrical distal end dimensioned to be positioned within the eye of a subject. In several embodiments movement of a cell-seeded substrate through said funnel shaped portion of the proximal end induces the cell-seeded substrate to roll into a cylindrical shape. In several embodiments, a rolled substrate does not overlap onto itself.

In some embodiments, the tool further comprises a plunger for pushing a cell-seeded substrate through said distal end and into a target tissue while other embodiments, employ a pressure source for pushing a cell-seeded substrate through said distal end and into a target tissue. Gas pressure is used in some embodiments, while fluid (or other pressure) is used in other embodiments.

In some embodiments, the distal end of the tool has an inner diameter ranging from about 1 mm to about 3 mm. Coordinately, in some embodiments the outer diameter ranges from about 1 mm to about 3 mm. In some embodiments, said distal end has an angle suitable for delivery of said substrate to the back wall of said subject's eye. However, in some embodiments, said distal end is configured to reversible connect with an extension tube having an angle suitable for delivery of said substrate to the back wall of said subject's eye.

In several embodiments, there is provided a method of treating a subject having outer retinal degenerative disease comprising surgically positioning an substrate as disclosed herein in a position juxtaposed to the outer nuclear layer of the photoreceptors in the eye of said subject. In several such embodiments, RPE cells seeded on said substrate support said photoreceptors, thereby treating the degenerative disease. In some embodiments, said surgical positioning is performed using a device comprising a handle, a recessed portion configured to hold said substrate, a port for transmitting positive or negative pressure to an substrate residing within said recessed portion, and one or more supporting features within said recessed portion, wherein said supporting features provide mechanical stability to said substrate.

In several embodiments, there is provided a system for the implantation of at least one cell-seeded substrate into the eye of a subject comprising a cannula comprising a cutting tip for creating an incision in the sclera of the eye of a subject and an internal lumen, a cell-seeded substrate comprising a non-porous polymer having a substantially homogeneous apical surface for the growth of cells, an inhomogeneous basal surface comprising supporting features juxtaposed with said substantially homogeneous apical surface, wherein, upon implantation into a subject, said substrate supports a population of cells suitable for the treatment of diseased or damaged ocular tissue for a period of time sufficient to treat said diseased or damaged ocular tissue, and a delivery tool configured to manipulate said cell-seeded substrate through said cannula and to deliver said implant to a target site in the eye of said subject.

In some embodiments, said delivery tool comprises a retractable forceps configured to pass through the lumen of said cannula. In some embodiments, said delivery tool comprises a polymer platform configured to enable said substrate to be rolled into a cylindrical shape, to support said cylindrical substrate, and to pass through the lumen of said cannula.

In several embodiments, there is provided a three-dimensional implantable substrate cage for cellular therapy to treat outer retinal degenerative disease. In some embodiments, the substrate cage comprises an outer shell having one or more pores therein and configured to form an inner lumen which is configured to receive stem cells. In some embodiments, the pores are configured to retain the one or more types of stem cells within the inner lumen while allowing an interaction between the one or more types of stem cells and cells of the target tissue.

In several embodiments, there is provided a method for treating retinal degeneration comprising culturing a plurality of stem cells, harvesting the stem cells, deploying the cultured stem cells into a three-dimensional polymeric substrate cage, implanting the cage into a target tissue.

In one embodiment, the outer shell of the substrate is polymeric. In one embodiment, the substrate further comprises a reporting feature. In some embodiments the reporting feature comprises microelectromechanical systems (MEMS) technology. In some embodiments, the MEMS reporting feature reports to a user regarding the viability of the cells housed within the substrate.

In one embodiment, the cells are RPE cells and the target tissue is the macula that has been damaged by age-related macular degeneration or other ocular disease. In one embodiment permeability of the substrate is defined solely by thickness of the biocompatible substrate. In one embodiment, the pores are between 0.5 and 1.5 µm. In one embodiment, the outer shell comprises polycaprolactone. In one embodiment, the polycaprolactone shell further comprises one or more of PEG and Arginine-Glycine-Asparagine. In one embodiment, the pores are generated by exposing the polymer substrate to an aqueous media.

In several embodiments, there is provided a method of fabricating a three-dimensional substrate cage for cellular therapy comprising preparing a substrate for the growth of cells, generating pores within the substrate, and sterilizing the substrate. In one embodiment, one or more types of stem cells are cultured on the substrate and a three-dimensional substrate cage is thereafter aligned and sealed, thereby containing the cells.

In several embodiments, there is provided a method of fabricating a three-dimensional substrate cage for cellular therapy comprising preparing two molds corresponding to top and bottom portions of the three dimensional substrate cage and configured to form an inner lumen upon assembly, polymerizing a polymeric solution in each portion of the mold, generating pores within the top and/or bottom portions of the substrate; and sealing the remaining portion or portions of the substrate cage with the substrate, thereby creating a three-dimensional substrate cage for cellular therapy. In one embodiment, the substrate cage is sterilized and sealed, and then cells are delivered into the inner lumen prior to implantation.

In one embodiment, the substrate cage is delivered to the subretinal space of an individual having retinal degenerative disease, and the substrate cage retains the stem cells the substrate cage after implantation but also allows processes from the retained cells to pass through the pores and interact with photoreceptors in the subretinal space. In one embodiment, the substrate cage is delivered to the subretinal space of an individual having retinal degenerative disease, and the substrate cage retains the stem cells after implantation but also allows chemical and cellular interaction between the encapsulated cells and the photoreceptors via the substrate cage pores. In one embodiment, the interaction supports the photoreceptors, thereby treating the retinal degeneration. In one embodiment, the interconnection further comprises one or more cells from the subretinal space of the individual passing through the pores and interacting with the substrate cage or the cells. In one embodiment, the substrate cage is implanted via an ab-interno surgical approach. In one embodiment, the substrate cage is implanted via an ab-externo surgical approach. In one embodiment, the individual afflicted with retinal degeneration is a mammal and in one embodiment, the mammal is a human. In one embodiment, the stem cells are deployed into the substrate cage immediately prior to implantation.

BRIEF DESCRIPTION OF THE DRAWINGS

FIG. 2A depicts a side view of a substrate structure in accordance with several embodiments disclosed herein. FIG. 2B depicts an internal view of a substrate cage structure in accordance with several embodiments disclosed herein.

FIG. 9 depicts the loading of cells according to several embodiments disclosed herein.

FIG. 10 depicts a cross-section of a substrate in accordance with several embodiments disclosed herein.

FIG. 12A shows scanning electron microscopy of polarized hESC-RPE showing apical specialization and microvilli. FIG. 12B depicts phagocytic activity of hESC similar to that of human native fetal RPE.

FIG. 13A depicts rat fundus photograph showing PLGA-RPE one week after implantation in the subretinal space; FIG. 13B depicts an OCT scan revealing the PLGA-RPE sheet (white arrow); FIG. 13C depicts the OCT image through the non-transplant area.

FIG. 14A depicts nuclear staining (DAPI) of preserved photoreceptors (ONL) in the transplanted area compared to the adjacent non-transplanted area (FIG. 14B).

FIG. 15A depicts hESC-RPE on PLGA by scanning electron microscopy (cross section). FIG. 15B shows growth of hESC-RPE surface modified parylene.

FIGS. 16A-16B depict high resolution imaging SDOCT of the retina used in several embodiments disclosed herein.

FIGS. 17A-17B depict top and side views, respectively, of a multi-chambered substrate cage comprising a substrate used to deliver cells in accordance with several embodiments herein. The substrate can be either non-degradable or degradable, facilitating interaction between cells in top and bottom chambers via defined material specifications. In some embodiments degradation rate and thickness of the material may be dependent on the time required for cells in both chambers to be implanted in the target location and make meaningful synaptic connections with, or allow for proper reciprocal nutrient exchange between, proximal cells.

FIG. 20A-20F depicts various substrates disclosed herein and related permeability data. A side view of an asymmetric substrate having a homogeneous apical surface 100 and an inhomogeneous basal surface comprising supporting structures in accordance with several embodiments disclosed herein is shown in FIG. 20A. Some embodiments further comprise a lip surrounding the apical surface 120 (see FIG. 20B). Some embodiments, further comprise a coating on the cell growth surface (FIGS. 20C-20D). Manipulation of the thickness of the substrate allows tuning of molecular size exclusion and diffusion (FIGS. 20E and 20F, respectively).

FIG. 21A depicts a scanning electron microscopic image of the planar apical surface of one embodiment of a substrate described herein. FIG. 21B depicts a scanning electron microscopic image of the bottom supporting surface of one embodiment of a substrate. FIG. 21C depicts a growth of stem cells on the planar apical surface of a substrate.

FIGS. 23A-23C depict embodiments of transplant tools used to manipulate and/or implant substrates seeded with cells.

FIG. 23D depicts an additional view of one embodiment of an insertion tool as described herein.

FIG. 32A is an infrared image of the fundus 1 month after transplantation. FIG. 32B is an autofluorescence image of the implant. FIG. 32C shows late phase angiography of the retinal-choroidal vasculature. FIG. 32D shows the location of the implant by OCT imaging.

FIG. 33A is an infrared image of the fundus 1 month after transplantation. FIG. 33B is an autofluorescence image of the implant. FIG. 33C shows the location of the implant by OCT imaging.

FIGS. 35A-35B show images of the RPE-substrate implanted in rat sub-retinal space. FIGS. 335C-35H show histological images of the RPE-seeded substrate at the indicated magnifications.

FIG. 44A shows a fundus image depicting the substrate (small arrow) implanted in a rat eye. FIG. 44B shows an SD-OCT image of a substrate (arrow) containing hESC-RPE cells implanted in the rat subretinal space.

DETAILED DESCRIPTION

Figure 1A:
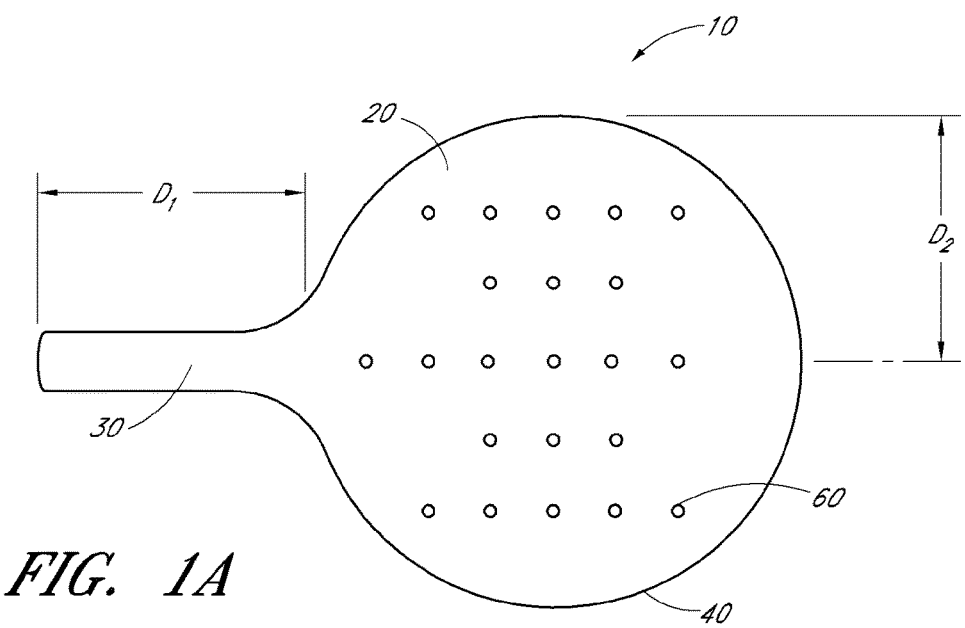
FIGS. 1A-1B depict general substrate structures in accordance with several embodiments disclosed herein.

Cellular therapy, the introduction of new cells into a tissue in order to treat a disease, represents a possible method for repairing or replacing diseased tissue with healthy tissue. Many approaches involve administration of cells (e.g., stem cells) to a target tissue, which often yields low retention rates and decreased incidence of long-term persistence of the transplanted (or implanted) cells. This may be due to a variety of factors, including cell washout and/or low cell survival rates in the delivery media. However, some diseases do not require the delivery or engraftment of the cells per se, but rather can require growth factors, chemical signals, or other interactions with the delivered cells. Several embodiments disclosed herein are directed to treating such diseases, and as such, comprise substrates configured to deliver the beneficial effects of cells (including physical, chemical, or other interaction) while retaining the cells within the substrate.

In particular, several embodiments relate to substrates into which stem cells are deposited in or on the substrate prior to administration of the substrate to a cell-therapy subject, and which function, post-administration, to retain the cells within or on the substrate while simultaneously facilitating a physical interaction between the stem cells within or on the substrate and portions of the target tissue. In several embodiments in particular, stem cells deposited within or on the substrate provide supportive effects for damaged or diseased cells of a target tissue, including, but not limited to, physical cell-cell interaction, release of nutrients or growth factors to the target tissue, attraction of other cell types, and the like. In several embodiments, the beneficial effects include one or more of secretion of growth factors which maintain the structural integrity of the choriocappilaris endothelium and photoreceptors (e.g. PEDF and VEGF), suppression of immunosuppressive factors which aids in the immune privileged status of the eye (which helps to suppress immune cell infiltration into the eye), secretion of neurotrophic factors, metabolic (e.g. exchange of glucose and fatty acids), functional benefits (e.g. delivery of retinol, phagocytosis of shed outer disc segments, and/or the reisomerization and restoration of visual pigments after photobleaching), or support of neural activity. In some embodiments, the support of neural activity occurs via interdigitation of the cells within or on the substrate with target tissue cells. For example, in one embodiment, apical microvilli of retinal pigmented epithelial cells within an implanted substrate interdigitate with host photoreceptors, thereby incurring a beneficial effect on the photoreceptors. In several embodiments, the benefit is via synapse formation (e.g. PR/bipolar cell), or other physical or chemical support of general cell viability). In several embodiments, one or more of these benefits occurs while partially or fully retaining cell somas within or on the substrate. In some embodiments, the cells from the host tissues project or infiltrate the substrate through the biological vias present in some embodiments of the substrate. For example, in some embodiments, new blood vessels or fibrous tissue protrude into the substrate. In some embodiments, these protrusions assist in anchoring the substrate, while in other embodiments, other beneficial effects (e.g., nutrient delivery, blood supply) are realized. Thus, as used herein, the term "interaction" shall be given its ordinary meaning and shall also refer to a one-way (implanted cells to target tissue or target-tissue to implanted cells) interconnect between cells or a two-way interconnect (both implanted cells to target tissue or target-tissue to implanted cells occur).

Further, in some embodiments, methods are provided for fabricating a custom substrate to treat a damaged or diseased tissue of an individual using tailored stem cell therapy. Additional information regarding fabrication of certain substrates provided for herein can be found in U.S. patent application Ser. No. 13/355,426, filed Jan. 20, 2012, the entire contents of which are incorporated by reference herein.

In several embodiments, porous substrates for improved cellular therapy are provided. In several embodiments, the substrates provided are non-porous (e.g., do not have an orifice or via) but are permeable, for example due to the dimensions of the substrate. Several such embodiments control the permeability of the substrate based on changes in thickness of the substrate. In some embodiments, substrates are both permeable and porous, with the permeability and porosity facilitating the interconnections between the implanted cells and the native cells. In several embodiments, the substrate is configured to receive cells and position the received cells in an optimal manner to facilitate regeneration of a damaged or diseased target tissue. In some embodiments, the substrates have specific characteristics (e.g., sizes, shapes, porosity) that retain the cells within the substrate, but simultaneously promote physical, chemical, or other interaction between the cells and target tissue. As used herein, the term "promote" shall be given its ordinary meaning and shall also be read to mean allow, enhance, permit, facilitate, foster, encourage, induce, and synonyms thereof. In some embodiments, the substrate is biodegradable, while in others, a non-biodegradable substrate is provided. In some embodiments the substrate is partly biodegradable and partly non-biodegradable. In several embodiments, fully non-biodegradable substrates are particularly advantageous, as their positioning relative to the implanted cells prevents access of immune cells into the transplant site and reduces risk of infection. Moreover, in several embodiments, a non-biodegradable substrate allows for identification and explant of transplanted cells should removal or replacement of the cells (e.g., additional "doses" of cells) be required. In several embodiments, the substrates herein are fabricated as a microelectromechanical system (MEMS). In several embodiments, the cells delivered to and retained within the substrate are stem cells. In several embodiments the substrate, and the cells retained therein are used to treat the damage associated with a disease, such as ocular degeneration, cardiac disease, vascular disease, and the like.

Substrates

As discussed above, the variety of diseases that lead to damage or loss of function of particular cell types is vast and represents an area of medicine in need of treatment approaches that go beyond typical surgical or pharmacological approaches. To address this need cellular therapy involves the use of cells, and in some cases fetal, umbilical cord, placenta-derived, adult, induced, or human embryonic stem cells and/or their partially or fully differentiated cellular derivatives to treat diseased or damaged tissues via replacement or regeneration. In several embodiments, substrates that improve the efficacy of cellular therapy are provided. As used herein, the terms "substrate" shall be given its ordinary meaning and shall also be used interchangeably with the term "implant" and/or "device", though it shall be appreciated that some embodiments described herein do not require implantation per se (e.g., those functioning as a "patch on a target tissue surface"). The contextual basis will make it clear to one of ordinary skill whether a particular embodiment is to be implanted within a target tissue. In addition, as used herein, the term "deliver" shall be given its ordinary meaning and shall also refer to the physical, chemical, or other type of interaction that the cells housed within the substrate provide to the target tissue without the release of cells from the substrate and/or engraftment of cells into the target tissue.

Types of Substrate

Based on the variety of diseases in which cellular therapy can be employed, a variety of different types of substrates may be advantageous, depending on the disease. In general, while many of the substrates disclosed herein inherently have three dimensions (e.g., a length, a width, and a height), some substrates disclosed herein are designed with particular attention being directed to one or more of these dimensions. For example, as discussed more fully below, several embodiments are referred to as 3-D substrate cages. In such embodiments, the substrate is sufficient to allow formation of at least one interior lumen. For example, in some embodiments, a cage structure with a purposefully designed 3-dimensional shape functions to provide one or more lumens or cavities within the substrate which functions to retain cells within the structure after delivery to a target site (while continuing to allow interactions between the cells and the target tissue). However, it shall be appreciated that the methods of fabrication, implantation, and uses disclosed herein shall be applicable to of any variety of substrates, devices, or implants described herein, unless otherwise expressly specified.

Figure 20E:
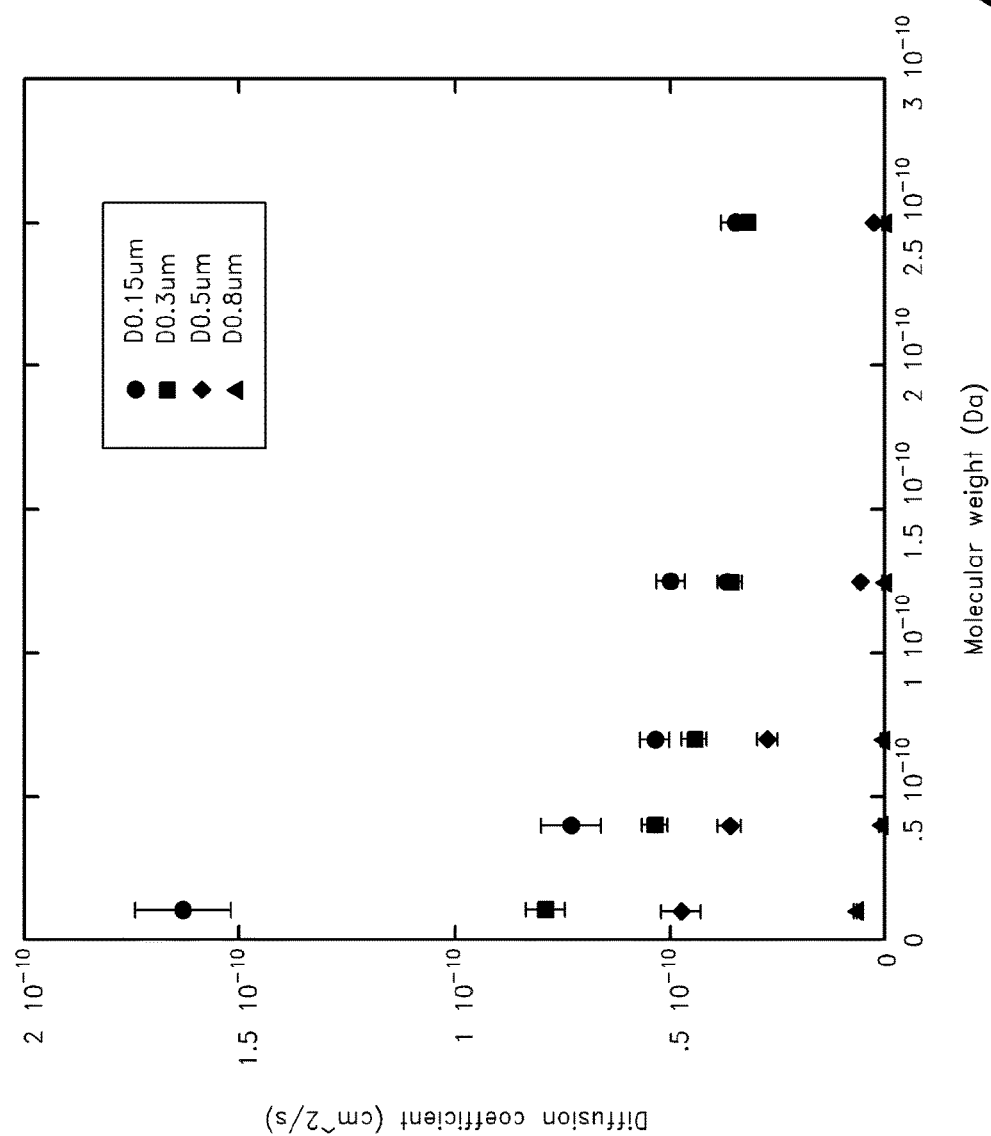
Figure 20F:
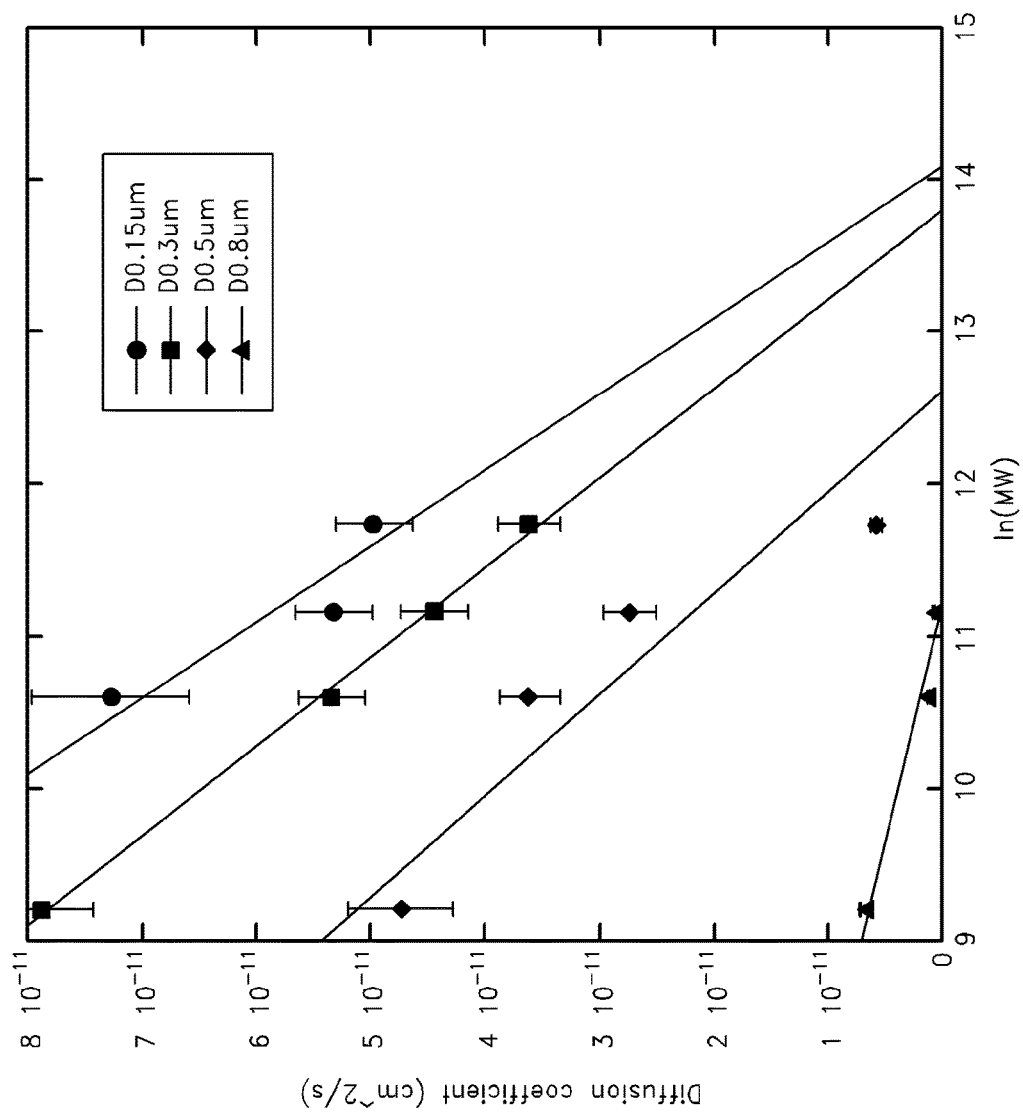

In several embodiments, the substrate is asymmetrical and inhomogeneous with distinct structural features on the apical and basal surfaces of the substrate. As used herein, the term "asymmetrical" and "substantially inhomogeneous" shall be given their ordinary meaning and shall also refer to non-planar or variable surfaces. Likewise, as used herein the term "substantially homogeneous" shall be given its ordinary meaning and shall also refer to those embodiments wherein a substantially homogeneous surface has been chemically treated to roughen, score, or otherwise etch the surface. These terms shall be used interchangeably, unless otherwise expressly indicated. For example, the apical surface of the substrate is, in some embodiments, surrounded by a rim on the perimeter which is intended to protect cell monolayer integrity from shear force imparted during transplantation and to inhibit lateral cell proliferation outside of the boundaries defined by substrate (see 120 in FIG. 20B). In several embodiments, the basal surface has periodic polymeric supports or columns providing mechanical stability to the substrate thereby (1) facilitating handling during cell culturing, and loading onto custom tool and subsequent surgical implantation, and (2) shielding a thinner membrane and overlying cellular sheet from mechanical disruption from force imparted due to positive or negative air pressure.

As used herein, the terms "3-dimensional" and "3-D" shall be given their ordinary meanings and shall also refer to those devices resembling a cage (e.g., having one or more interior lumens or cavities). In light of such variability in the design of substrates disclosed herein, the disclosure below, unless otherwise specified shall be appreciated to be applicable to any such variety of substrate.

Dimensions

Based on the variety of diseases in which cellular therapy can be employed, and limitations of delivery of cells alone, several embodiments provide substrates for improved cellular therapy. In several embodiments, the disease to be treated or the cells to be targeted define, at least in part, the dimensions of the substrate. For example, in several embodiments substrates are dimensioned for implantation in particular target tissues, while in other embodiments, substrates are dimensioned for placement on or near a target tissue.

In several embodiments, substrates disclosed here are utilized in treatment of ocular disease. In such embodiments, certain substrate dimensions are utilized depending on the ocular tissue to be targeted. For example, a substrate to be implanted in the vitreal chamber would likely differ in dimension from a substrate to be implanted in the suprachoroidal space. In general, dimensions of certain ocular cavities, spaces, and tissue can be obtained from general knowledge of ocular anatomy. In certain embodiments, specific measurements are obtained from an individual to determine the specific dimensions required to fabricate a customized substrate.

In several embodiments, anchor features are fabricated into the substrate to allow secure and precise positioning of the substrate at a target site. In some instances, once the substrate is in place and the cells within or on the substrate have established an interconnect with the target cells, micromovements of the substrate could damage and/or sever the interconnect, thereby reducing the therapeutic efficacy of the cells. Therefore, in several embodiments, anchor structures are attached and/or built in to the substrates disclosed herein. For example, in some embodiments, one or more holes are provided that allow the substrate to be sutured to target tissue. In some embodiments, a bioadhesive and/or an adhesive protein is used. In some embodiments, microhairs or a roughened surface of the substrate provide friction-based anchoring of the substrate. In some embodiments, MEMS features such as clamps or latches are used to grasp or otherwise connect the substrate to the target tissue. In some embodiments, the target tissue is dimensioned sufficiently to securely hold a substrate without the need for specialized anchors.

With reference to FIG. 1, certain general dimensions are provided for 3-dimensional (e.g., cage) substrates according to several embodiments described herein. In several embodiments, the substrate 10 comprises a substrate body 20 and a substrate tail 30. In some embodiments, the length of the substrate tail D1 ranges from about 0.5 mm to about 5 mm. In some embodiments, the tail measures from about 0.5 to 1 mm, from about 1.0 to 1.5 mm, from about 1.5 to 2.0 mm from about 2.0 to 2.5 mm, from about 2.5 to 3.0 mm, from about 3.0 to 3.5 mm, from about 3.5 to 4.0 mm, from about 4.0 to 4.5 mm, from about 4.5 to 5.0 mm, and overlapping ranges thereof. In some embodiments, the substrate tail measures between about 0.7 to 1.3 mm, including 0.8, 0.9, 1.0, 1.1, and 1.2 mm. In several embodiments, the substrate tail, the substrate body (below) or the total dimensions of the substrate as a whole are such that forceps may be used to grasp and manipulate the substrate. At the same time, these dimensions are balanced with maintaining sufficient structure to the substrate that it is not easily bent, kinked, or otherwise damaged during handling or implantation.

Figure 19A:
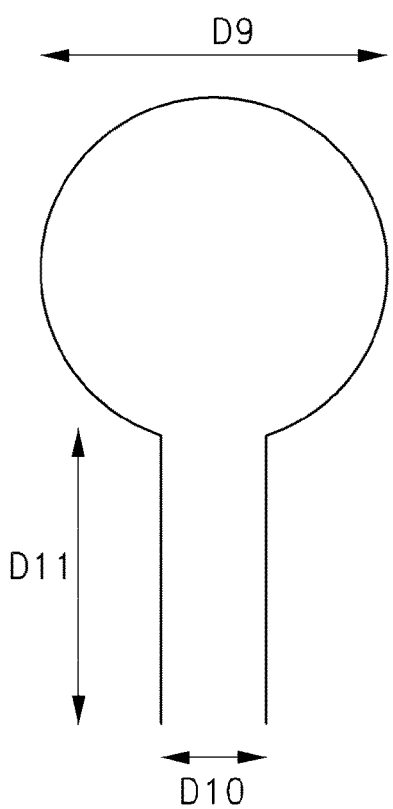
FIGS. 19A-19B depict top views of various substrate shapes in accordance with several embodiments disclosed herein.

In several embodiments, the substrate body is generally circular (see e.g., FIG. 1A and FIG. 19A). However, in some embodiments (see e.g., FIG. 1B and FIG. 19B), other shapes, including but not limited to rectangles, squares, ovals, and cylinders are used. With reference to FIG. 1A, or other embodiments having a generally circular body, the radius of the substrate body measures from about 0.5 to about 5 mm. In some embodiments, the radius measures from about 0.5 to 1 mm, from about 1.0 to 1.5 mm, from about 1.5 to 2.0 mm from about 2.0 to 2.5 mm, from about 2.5 to 3.0 mm, from about 3.0 to 3.5 mm, from about 3.5 to 4.0 mm, from about 4.0 to 4.5 mm, from about 4.5 to 5.0 mm, and overlapping ranges thereof. In some embodiments, the substrate body radius measures between about 0.7 to 1.3 mm, including 0.8, 0.9, 1.0, 1.1, and 1.2 mm.

Figure 1B:
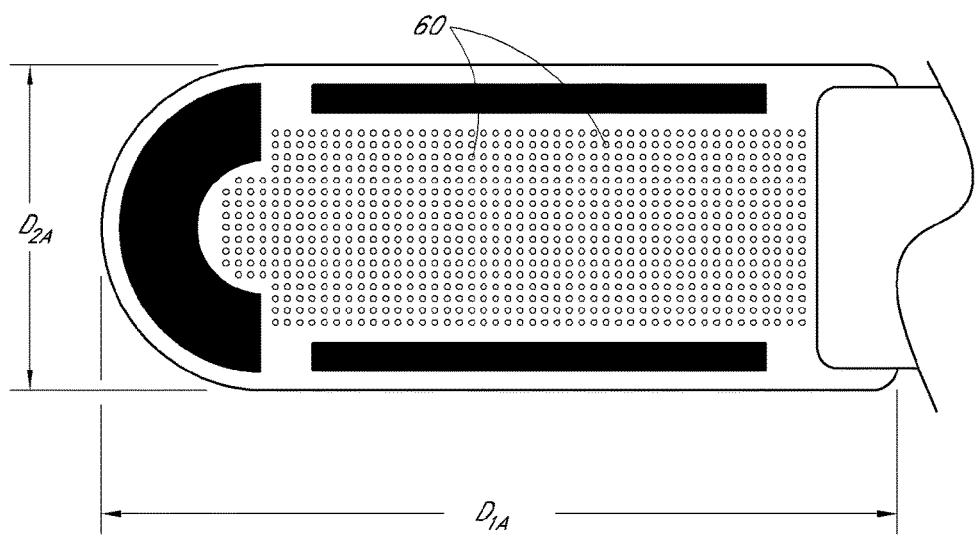

Similar dimensions are used in several embodiments not having a rounded or circular body. With reference to FIG. 1B, D1A represents the length of the substrate, and in some embodiments, ranges from about 0.5 to about 5 mm. In some embodiments, the length measures from about 0.5 to 1 mm, from about 1.0 to 1.5 mm, from about 1.5 to 2.0 mm from about 2.0 to 2.5 mm, from about 2.5 to 3.0 mm, from about 3.0 to 3.5 mm, from about 3.5 to 4.0 mm, from about 4.0 to 4.5 mm, from about 4.5 to 5.0 mm, and overlapping ranges thereof. Dimension D2A represents the width of the substrate and may have similar measurements as D1A above.

Figure 2A:
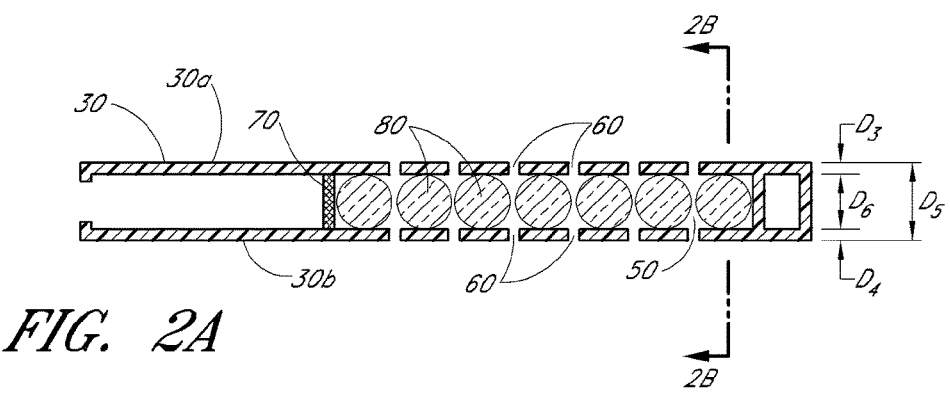
FIGS. 2A-2B depict internal views of several embodiments disclosed herein.

With reference now to FIG. 2A, which is a side view depicting the 3-dimensional structure of several embodiments disclosed herein, dimensions D3 and D4 represent the thickness of the substrate cage wall 30. D3 and D4 have the same dimension in some embodiments, while in other embodiments, the dimensions vary between the two. In some embodiments, D3 and/or D4 measure between about 1.0 and 5.0 microns. In some embodiments, the thickness of the wall ranges from about 0.5 to 1 μm, from about 1.0 to 1.5 μm, from about 1.5 to 2.0 μm, from about 2.0 to 2.5 μm, from about 2.5 to 3.0 μm, from about 3.0 to 3.5 μm, from about 3.5 to 4.0 μm, from about 4.0 to 4.5 μm, from about 4.5 to 5.0 μm, and overlapping ranges thereof. In some embodiments, the thickness of D3 and/or D4 is ranges from about 1.5 to 2.5 μm, including 1.6, 1.7, 1.8, 1.9, 2.0, 2.1, 2.2, 2.3, and 2.4 μm. In one embodiment, D3 is maximally about 7 μm, which allows microvilli to penetrate the vias 60 fully. In one embodiment, D4 is greater than D3 in order to provide structural rigidity to the substrate cage. In some embodiments, one or more surfaces of the substrate cage is fabricated in a flexible "accordion" shape, to allow the substrate cage to expand upon delivery of cells to the lumen of the substrate cage. In some embodiments this expansion is made possible by using a highly elastomeric polymer. In some embodiments, the cell delivery solution comprises a larger overall volume than the volume of cells that are desired to be retained within the substrate cage. As such, the accordion shape of some embodiments, allows the substrate cage to expand to accommodate this excess fluid and then retract as the excess fluid passes through the pores of the substrate cage.

As shown in FIG. 2A, the lumen 50 is an open space within the outer shell of the substrate cage that houses the cells that will provide a therapeutic effect to the target tissue. Depending on the cell type to be delivered, the quantity of cells to be housed within the substrate cage, and other limiting physical parameters of the target tissue, the height of the lumen D6 can range from about 4 μm to about 75 μm. In some embodiments, D6 measures from about 4 to 10 μm, from about 5 to 20 μm, from about 10 to 30 μm, from about 25 to 40 μm, from about 30 to 50 μm, from about 45 to 60 μm, from about 50 to 75 μm, from about 65 to 75 μm, or overlapping ranges thereof. In several embodiments, D6 ranges from about 10 to about 50 μm. In some embodiments, the height D5 of the lumen 50 is the same as the height of the membrane 70 that allows cell delivery to the lumen, but prevents cellular backflow. However, in some embodiments, depending on the overall shape of the substrate may vary, such that a first portion does not have the same dimension as a second portion.

The total height of the substrate cage D5 is a function of D3, D4 and D5, as well as any characteristics of the target tissue that need to be accounted for in the fabrication of the substrate cage. In some embodiments, D5 ranges from about 6 to about 85 μm, including 5 to 20 μm, 20 to 30 μm, 30 to 40 μm, 40 to 50 μm, 50 to 60 μm, 60 to 70 μm, 70 to 85 μm and overlapping ranges thereof. In some embodiments, the dimensions are adjusted to account for the location of the target tissue. For example, if the target tissue is frequently under load (e.g., pressure, contractile, etc.) but presents a small area suitable for implantation, the substrate cage can be fabricated with thicker walls and a suitable overall height (larger D3 and/or D4 relative to D5). As a result, D6 would be smaller. In other embodiments, walls of the substrate cage can be fabricated to maximize D6 relative to D5. Thus, in several embodiments, the dimensions of the substrate cage are tailored to the target tissue generally, or in some embodiments, to the target tissue dimensions of a particular individual.

Figure 18B:
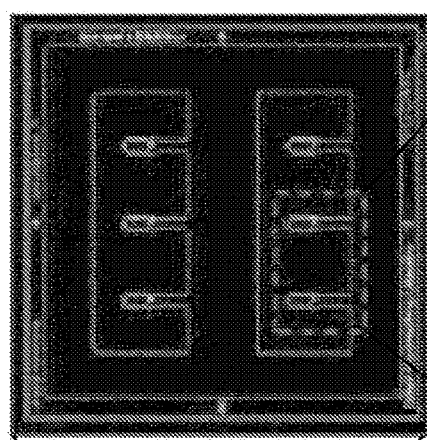
FIGS. 18A-18D depict various embodiments of substrate layouts in substrate frames.
Figure 18C:
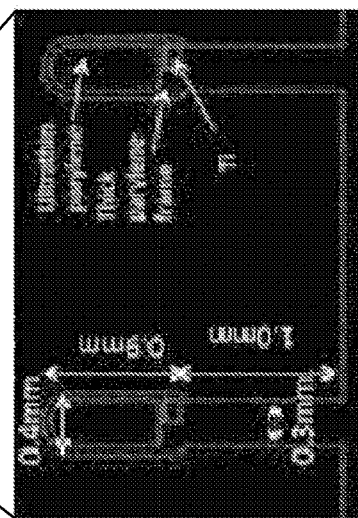
Figure 18A:
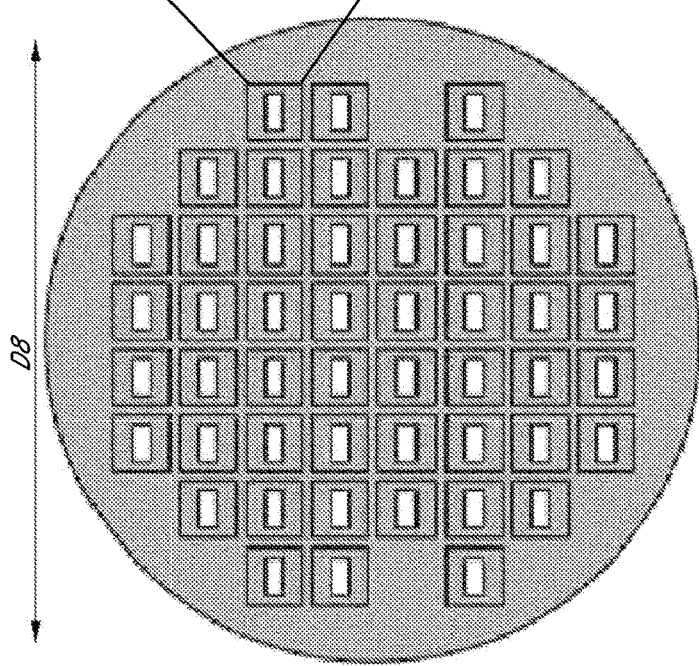
Figure 22B:
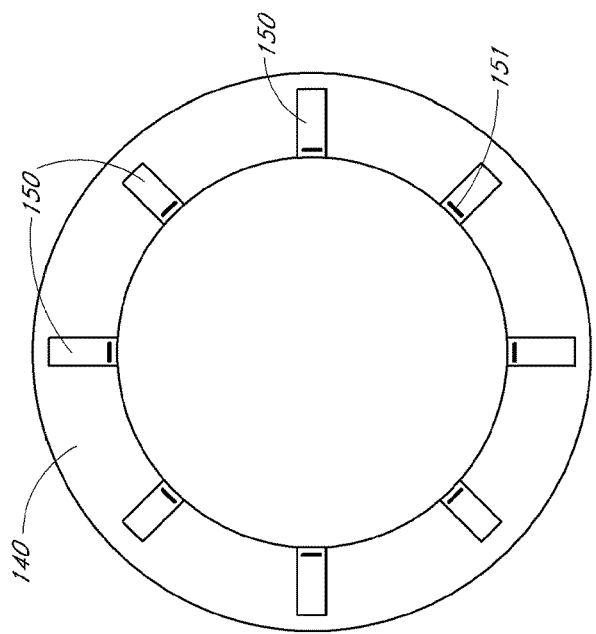
FIG. 22B depicts one embodiment of a device used to hold a substrate frame and cut individual substrates from the frame.
Figure 22A:
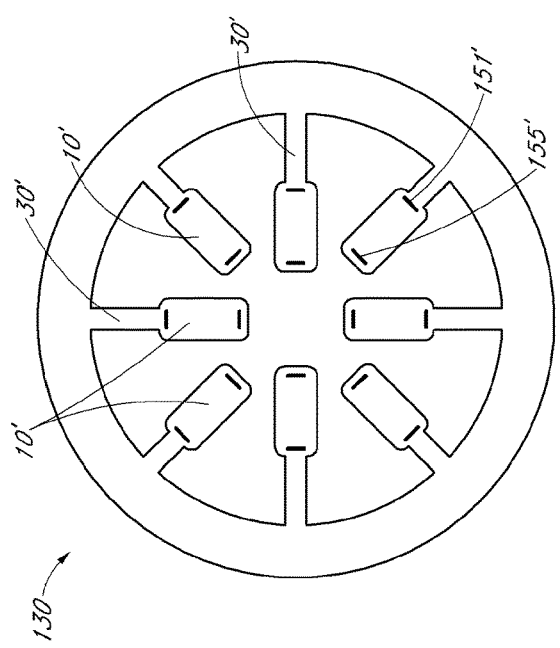
FIG. 22A depicts an additional embodiment of substrate layout in a substrate frame.

With reference to FIGS. 18A and 22A, in several embodiments, a plurality of substrates are positioned within a culture vessel in order to allow for the concurrent seeding of cells across the plurality of substrates. In several embodiments, the diameter D8 is designed to be slightly smaller than commercially available cell culture dishes adequate for cGMP scale up such that the substrate frame fits snuggly in the dish (e.g., fit to reduce/minimize movement of the substrate). Based on the diameter D8 (or width, if not circular) of the substrate frame culture vessel, the number of substrates that are concurrently seeded with cells will vary. In some embodiments, and depending on culture dish diameter, D8 is about 14-15 cm, about 9-10 cm, or about 4-5 cm. In some embodiments, D8 is less than about 4 cm, including 3, 2, 1, and 0.5 cm. In several embodiments, multiwell culture vessels are used. For example, in several embodiments 6-well, 12-well, 24-well, or 48-well plates are used. In some embodiments, 96-well plates are used. In several embodiments, the depth of the wells ranges from about 1 to about 1.7 mm, including about 1.1, 1.2, 1.3, 1.4, 1.5, 1.6 mm. In several embodiments, the diameter of the wells (which can be optimized based on the number of substrates to be cultured in the well) ranges from about 3 to about 20 mm, including about 3 to about 5 mm, about 5 to about 7 mm, about 7 to about 9 mm, about 9 to about 11 mm, about 11 to about 13 mm, about 13 to about 15 mm, about 15 to about 17 mm, about 17 to about 19 mm, about 19 to about 20 mm, and overlapping ranges thereof. In several embodiments, the height of the sidewalls ranges from about 10-20 mm, including about 10 to about 12 mm, about 12 to about 14 mm, about 14 to about 16 mm, about 16 to about 18 mm, about 18 to about 20 mm, and overlapping ranges thereof. Certain embodiments, of such culture vessels are commercially available with established well dimensions.

In some embodiments, a culture vessel that is rectangular or square is used in order to maximize the culture area of the vessel. In some embodiments, and especially with regard to rectangular or square dishes, a custom sized (e.g., not commercially available) culture vessel is designed and fabricated. Specifications of these custom dishes such as width and length are defined by multiple variables, including, but not limited to, (1) the minimum number of substrates or custom tool heads required to provide adequate sampling at final release testing to show lot-to-lot consistency, (2) finalized substrate shape (either circular (FIG. 19A) or rectangular (FIG. 19B)) and associated lateral dimensions (D9-D11 with regard to circular embodiment; D10, D12, D13 with regard to oblong or rectangular embodiment with rounded edges, or a oval shaped hybrid of the two), etc.

Based on the dimensions of the culture vessel, and the target tissue for the substrate, the dimensions of the substrates may vary. As discussed in more detail below and shown generally in FIG. 19A, in several embodiments, there is provided a substantially inhomogeneous substrate having a circular body and a tail. The dimensions of this type of substrate, while overlapping with the 3-dimensional substrate cages described above, are specifically designed with the strength, durability, and manipulability of substrates that do not have a naturally increased stability by being formed in a cage-like structure or do not require a lumen. In some embodiments, a fully planar substrate is used. In some embodiments, both top and bottom surfaces are non-planar.

As such, the diameter D9 of such inhomogeneous substrates ranges from about 1 mm to about 8 mm, including about 1 to about 2 mm, about 2 to about 3 mm, about 3 to about 4 mm, about 4 to about 5 mm, about 5 to about 6 mm, about 6 to about 7 mm, about 7 to about 8 mm, and overlapping ranges thereof. In certain embodiments, diameters of about 3 to about 5 mm are used, including 3.2, 3.4, 3.6, 3.8, 4.0, 4.2, 4.4, 4.6, 4.8, and 5.0 mm.

Tail (or handle) width D10 ranges, in several embodiments, from between about 0.1 mm to about 6 mm, including about 0.2 to about 1.0 mm, about 1.0 to about 2.0 mm, about 2.0 to about 3.0 mm, about 3.0 to about 4.0 mm, about 4.0 to about 5.0 mm, about 5.0 to about 6.0 mm, and overlapping ranges thereof.

Tail (or handle) length D11 ranges, in several embodiments, from between about 1 mm to about 20 mm, including about 1 to about 2 mm, about 2 to about 3 mm, about 3 to about 4 mm, about 4 to about 5 mm, about 5 to about 6 mm, about 6 to about 7 mm, about 7 to about 8 mm, about 8 to about 9 mm, about 9 to about 10 mm, about 10 to about 11 mm, about 11 to about 12 mm, about 12 to about 13 mm, about 13 to about 14 mm, about 14 to about 15 mm, about 15 to about 16 mm, about 16 to about 17 mm, about 17 to about 18 mm, about 18 to about 19 mm, about 19 to about 20 mm, and overlapping ranges thereof.

Figure 19B:
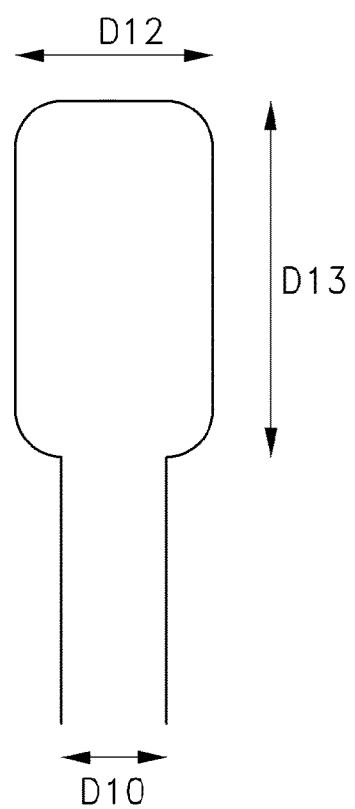

Similar tail width and length are used in oblong (e.g., oval or largely rectangular) substrates, as depicted generally in FIG. 19B. Width D12 of such substrates ranges, in several embodiments between about 0.2 and about 7 mm, including from about 0.2 to about 0.4 mm, about 0.4 to about 0.6 mm, about 0.6 mm to about 0.8 mm, about 0.8 mm to about 1.0 mm, about 1.0 to about 2.0 mm, about 2.0 to about 3.0 mm, about 3.0 to about 4.0 mm, about 4.0 to about 5.0 mm, about 5.0 to about 6.0 mm, and overlapping ranges thereof.

The length D13 of such oblong substrates ranges, in several embodiments, from between about 0.5 mm to about 9 mm, including about 0.5 to about 1.0 mm, about 1.0 to about 2.0 mm, about 2.0 to about 3.0 mm, about 3.0 to about 4.0 mm, about 4.0 to about 5.0 mm, about 5.0 to about 6.0 mm, about 6.0 to about 7.0 mm, about 7.0 to about 8.0 mm, about 8.0 to about 9.0 mm and overlapping ranges thereof. In some embodiments, length D13 ranges from about 4 to about 7 mm, including 4.2, 4.4, 4.6, 4.8, 5.0, 5.2, 5.4, 5.6, 5.8, 6.0, 6.2, 6.4, 6.8, and 7.0 mm.

Figure 24:
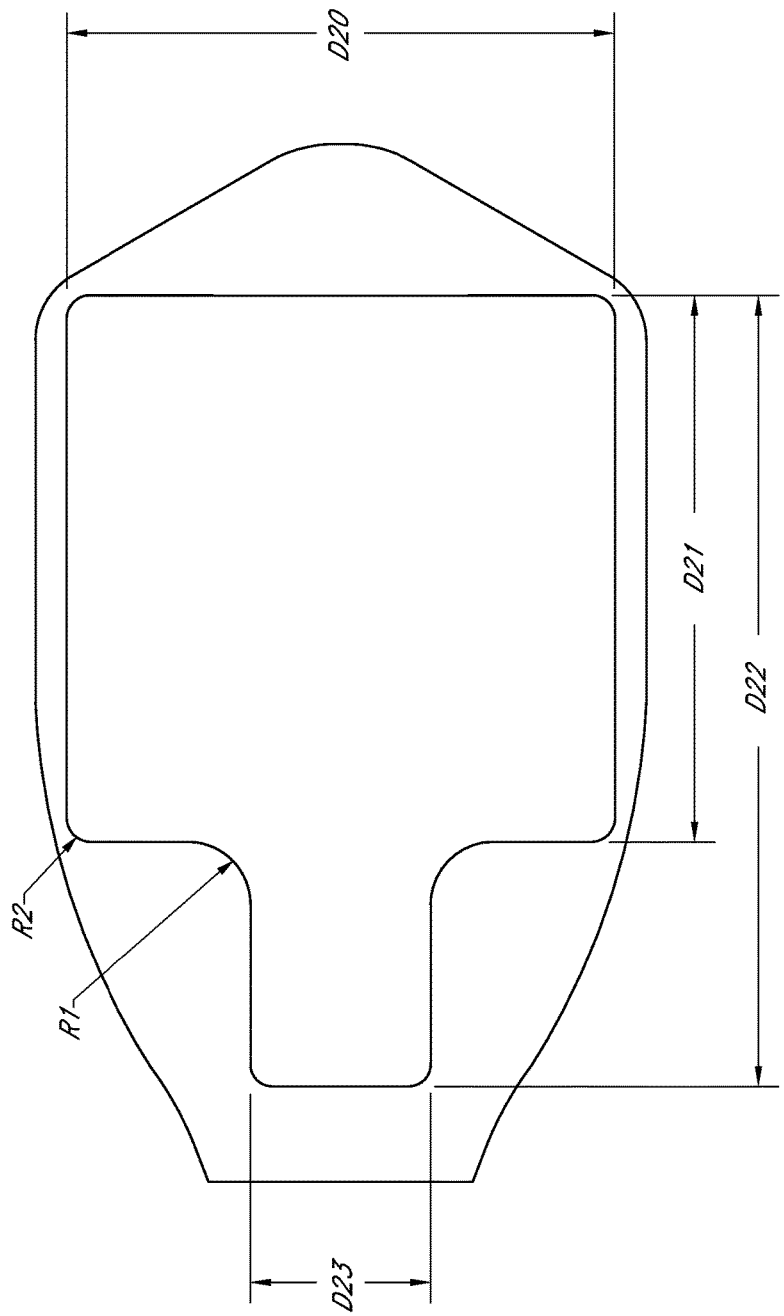
FIG. 24 illustrates an example of a substrate according to several embodiments disclosed herein.

Additional dimensions that are used in several embodiments are shown in FIG. 24. D14 represents the width of several embodiments of the substrate, which can range from about With reference to FIG. 20, certain general cross-sectional dimensions are provided for inhomogeneous substrates with and without a perimeter lip (FIG. 20B). Embodiments employing either of these cross-sectional structures can be used with commercially available cell culture dishes, or other types of dishes such as those described above. In several embodiments, the substrate has a homogeneous apical layer 100 which provides a surface for cellular growth. In several embodiments, the thickness D14 of the apical cell growth surface 100 is less than about 4 μm thick. In some embodiments, the thickness ranges from about 0.01 to about 0.05 μm, from about 0.05 to about 0.1 μm, from about 0.1 to about 0.2 μm, from about 0.2 to about 0.5 μm, from about 0.5 to about 3.5 μm, from about 0.5 to about 3.0 μm, from about 0.7 to about 3.0 μm, from about 1.0 to about 3.0 μm, from about 1.5 to about 2.5 μm, from about 1.8 to about 2.2 μm, and overlapping ranges thereof. In some embodiments, the thickness ranges from between about 0.5 and 1.0 μm, including 0.6, 0.7, 0.8, and 0.9 μm. As shown, the apical cell growth surface 100 is paired with thicker supports 110 on the basal surface. The supports 110 provide in some embodiments, mechanical rigidity, which aids in supporting the full apical cell growth surface during handling and surgical insertion. In those embodiments wherein the cells growing on the surface are RPE cells, after surgical insertion, the apical cell growth surface (and the RPE cells) will be juxtaposed with the photoreceptors in the eye, thereby serving to support the health of the photoreceptors. In several embodiments, the supports also inhibit lateral growth of the cells and possible extension of growth onto the basal side of the substrate. The supports, in several embodiments also inhibit cell growth into the vitreous via mechanical disruption of retinal integrity. (The latter results in a complication known as proliferative vitreo-retinopaty (PVR)). Therefore, such embodiments have a homogeneous apical surface conducive to cell growth paired with a basal surface having an inhomogeneous, but periodic, topology defined by the size and pitch of the supports. In some embodiments, the supports are columnar in shape, while in other embodiments, other shapes are used (e.g., cuboidal). In some embodiments a rim is employed on the apical surface to inhibit lateral growth and protect from shear force during surgical implantation.

As shown in FIGS. 20A and 20B, the basal surface supports 110 range in total height D15 (as measured from the apical cell growth surface layer to the termination of the support) between about 3 μm and about 15 μm, including about 3 to about 5 μm, about 5 to about 7 μm, about 7 to about 9 μm, about 9 to about 11 μm, about 11 to about 13 μm, about 13 to about 15 μm, and overlapping ranges thereof. In some embodiments, the supports range in height from between about 5 μm to about 8 μm, including 5.2, 5.4, 5.6, 5.8, 6.0, 6.2, 6.4, 6.6, 6.8, 7.0, 7.2, 7.4, 7.6, 7.8, and 8.0 μm.

In several embodiments, the apical and basal surfaces comprise different materials. For example, in one embodiment, the apical cell growth surface may be made of first material that is more conducive to cell growth, while the basal surface is made of a second (or modified first material)

that imparts strength and/or durability to the substrate as a whole. In some embodiments, the apical surface comprises a coating or thin layer of deposited material 100' that assists in cell growth and/or adherence. (see e.g., FIGS. 20C and 20D). In several embodiments, this layer is between about 10 and 100 nm in thickness. In some embodiments, the layer is between about 20 to 30 nm, between about 30 to 40 nm, between about 40 to 50 nm, between about 50 to 60 nm, between about 60 to 70 nm, between about 70 to 80 nm, between about 80 to 90 nm, between about 90 to 100 nm, and overlapping ranges thereof.

In several embodiments, the layer 100' comprises parylene AM. In several embodiments the layer comprises ammonia treated parylene C. In several embodiments, the layer comprises parylene C and polydopamine. In several embodiments, parylene AM, parylene C, ammonia and/or oxygen treated parylene C (for the purposes of adding functional groups and roughening the surface), and parylene C treated with either polydopamine, vitronectin, retronetin, or matrigel are used. In several such embodiments, the second layer (100 in FIGS. 20A-20D) comprises a blend of cyclic and linear arginine-glycine-aspartic acid residues. In several embodiments, the second layer comprises a synthetic cell growth matrix (e.g., SYNTHEMAX™ by Corning). In one embodiment, the inhomogeneous basal surface comprises parylene C, with a parylene AM layer as the substantially homogeneous apical surface. In one embodiment, the parylene AM is coated with one or more of matrigel, vitronectin, retronectin, poly-L-dopamine. In several embodiments the poly-L-dopamine coating is generated by reacting PEG-(N-Boc-L-DOPA)$_2$ with cyclic Arginine-Glycine-aspartic in an oxidative aqueous media (such as sodium periodate (NaIO$_4$) to generate a poly-L-dopa coating. Alternatively, PEG-(N-Boc-L-DOPA)$_2$ is reacted with RGD-L-DOPA in an oxidative aqueous media (such as sodium periodate (NaIO$_4$) to generate a poly-L-dopa coating.

While several embodiments disclosed herein involve the in vitro seeding of cells onto a substrate, followed by subsequent implantation of a cell-seeded substrate, alternative embodiments comprise a stepwise procedure. For example, in some embodiments a substrate alone (without cells) is implanted into a target site. Subsequently, cells can be delivered to the substrate where they will attach and grow and provide therapeutic effect. In some embodiments, implantation of the substrate and seeding of the substrate with cells are done during the same surgical procedure. Such an approach is advantageous to, for example, reduce potential damage to the cells on the substrate during the implantation process. Further, the surgeon can confidently place the substrate in an ideal location without concern that the stem cells weren't all damaged during the implantation process. After precise positioning at the target site is confirmed, the surgeon may then seed the substrate with the desired number of stem cells, complete the surgical procedure, and know that the stem cells seeded onto the substrate were not damaged during manipulation of the substrate. In other embodiments, implantation of the substrate is done in a separate surgical procedure from seeding of the substrate with cells. This approach also has advantages. For example, in such approaches, the time between the two procedures can be sufficiently long to ensure secure and safe (e.g., no host rejection) of the substrate. Additionally, such approaches can allow the tailoring of the number of stem cells that need to be implanted. For example, rather than be limited by a "ready to use" cell-seeded substrate, a surgeon can custom cut a substrate to fit a particular patient, and later seed that substrate with an optimal number of cells for that patient. Two schemes depicting two embodiments of implantation are depicted generally in FIGS. 20G and 20H.

Figure 20G:
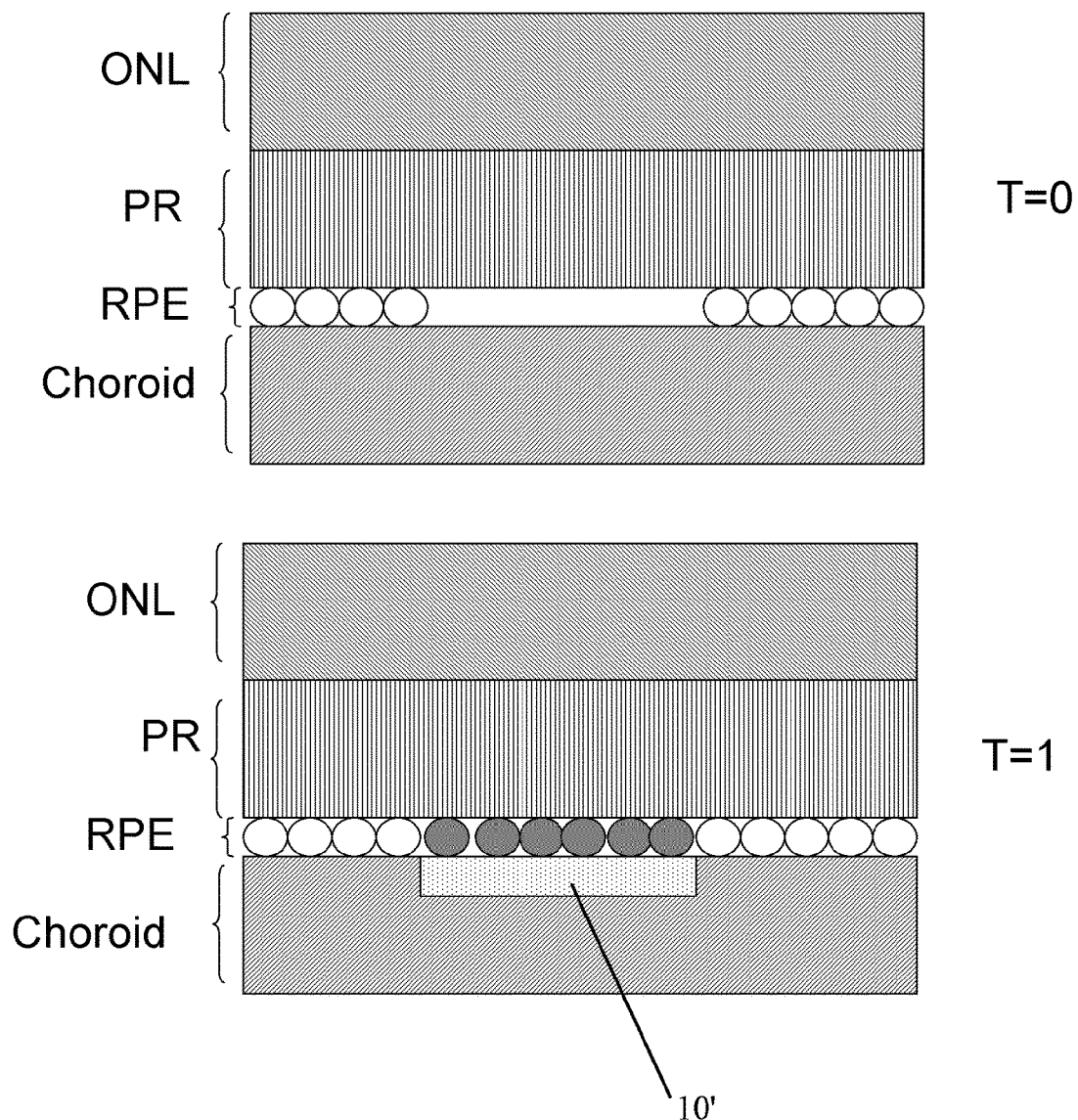
FIGS. 20G and 20H schematically depict various implantation time frames.
Figure 20H:
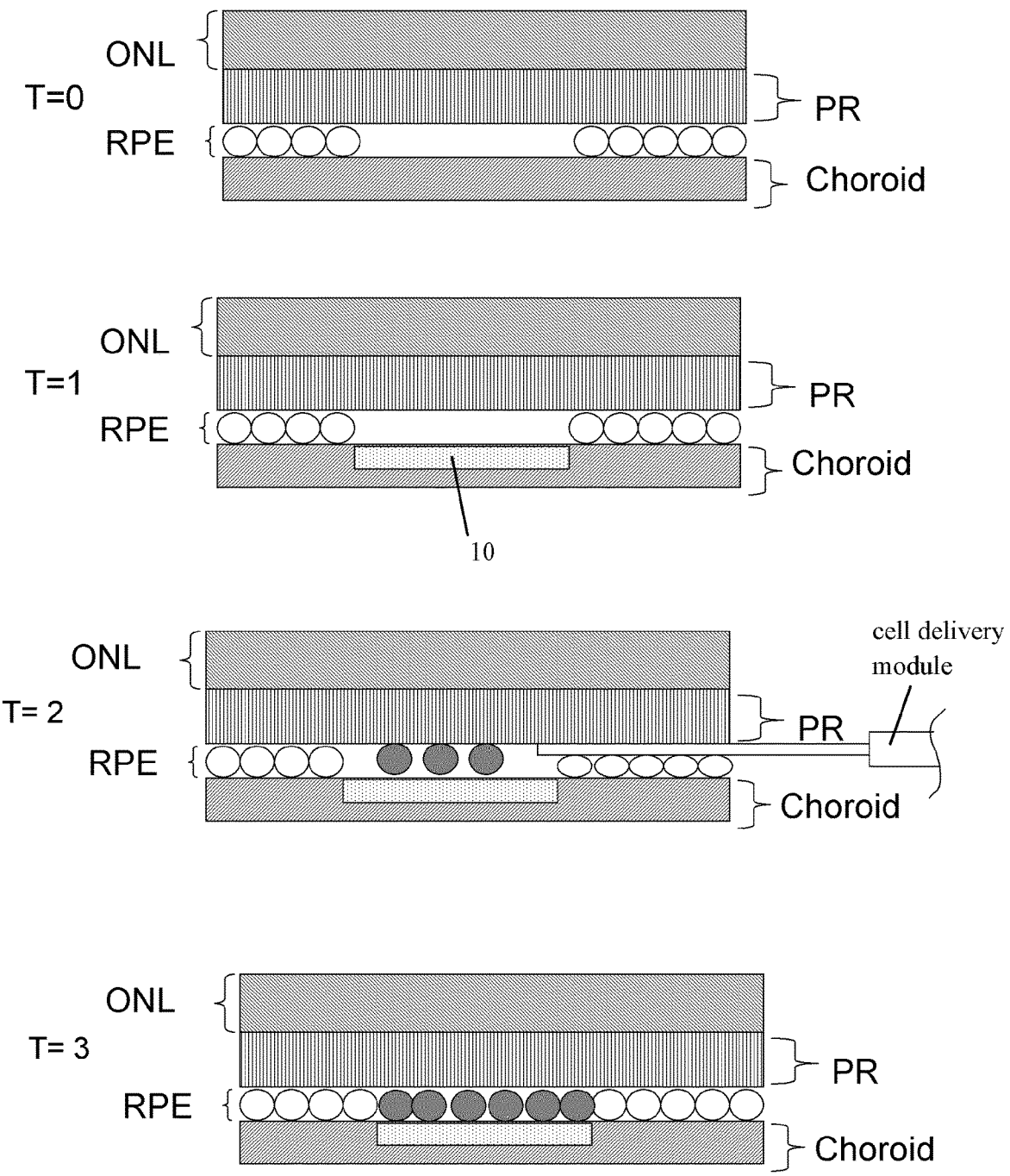

FIG. 20G schematically depicts an ocular implantation approach employing a cell seeded substrate. As shown at time zero, the RPE layer has a damaged area (shown as a lack of cells) which will be treated with cell therapy. At time point 1, which is after surgical implantation, the substrate seeded with RPE cells (shown with gray shading to differentiate in vitro RPE cells from native RPE cells) is shown resting between the choroid and the photoreceptor layer. FIG. 20H, schematically depicts implantation of a substrate followed by later, in vivo, seeding of cells onto the substrate. Again, at time point 0, a cross-section of the eye is shown with damaged or missing RPE cells. At time point 1, the substrate 10 has been implanted into the eye of the subject. Note that the graphical depiction of the substrate resting within the choroid is shown for illustrative purposes (e.g., to allow space to show the cells in subsequent steps). The location of the substrates post-implantation is in accordance with the description herein. At time point 2, the substrate is seeded with cells via a cell delivery module (e.g., a syringe or other dispensing device sized for ocular applications). In certain embodiments, separate implantation and seeding approaches employ substrates with a coating that facilitates seeding the implants at a later time. For example, in several embodiments a vitronectin coated substrate is used. Also, as discussed herein, in other embodiments, other coatings, including but not limited to one or more of matrigel, retronectin, poly-L-dopamine are used. As shown at time=3, post in vivo seeding, the substrate maintains the RPE cells in a physiologically relevant position to treat, for example, AMD. It shall be appreciated, that the step of implanting the substrate and the step of seeding the substrate with cells can occur during the same surgical procedure (e.g., sequentially) or alternatively can be separated by a period of time (e.g. a few hours, several days, up to several weeks, or longer) depending on the health status and needs of the particular patient.

Alternative embodiments, a non-limiting example of which is shown in FIG. 20B, further comprise a substrate lip 120 lining the perimeter of the apical cell growth surface 100 that functions to shield cells growing on the apical surface from fluid shear stress during culturing of the cells, manipulation of the substrate, and/or during or after surgical implantation into a target tissue (e.g., the eye). The lip further functions to define a boundary to control growth of the cells on the surface; thereby preventing the growth of the cells from the apical surface (cell growth surface 100) to the basal side of the substrate. Moreover, the substrate lip 120 limits disruption of monolayer integrity during the separation of an individual substrate from an array of substrates (e.g., those shown in FIG. 18A or 22A). In several embodiments the lip has a width D18 ranging from between about 10 µm to about 1500 µm (1.5 mm). In some embodiments, the width ranges from about 10 to about 100 µm, from about 100 to about 200 µm, from about 200 to about 300 µm, from about 300 to about 400 µm, from about 400 to about 500 µm, from about 500 to about 600 µm, from about 600 to about 700 µm, from about 700 to about 800 µm, from about 800 to about 1000 µm, from about 1000 to about 1100 µm, from about 1100 to about 1200 µm, from about 1200 to about 1300 µm, from about 1300 to about 1400 µm, from about 1400 to about 1500 µm, and overlapping ranges thereof.

In several embodiments the lip has a height D19 ranging from between about from between about 10 µm to about 1500 µm (1.5 mm). In some embodiments, the height ranges from about 10 to about 100 µm, from about 100 to about 200 µm, from about 200 to about 300 µm, from about 300 to about 400 µm, from about 400 to about 500 µm, from about 500 to about 600 µm, from about 600 to about 700 µm, from about 700 to about 800 µm, from about 800 to about 1000 µm, from about 1000 to about 1100 µm, from about 1100 to about 1200 µm, from about 1200 to about 1300 µm, from about 1300 to about 1400 µm, from about 1400 to about 1500 µm, and overlapping ranges thereof. In some embodiments, the height ranges from between about 20 to about 300 µm, including about 20 to about 50 µm, about 50 to about 100 µm, about 100 to about 150 µm, about 150 to about 200 µm, about 200 to about 250 µm, about 250 to about 300 µm, and overlapping ranges thereof.

Figures 21A, 21B, 21C:
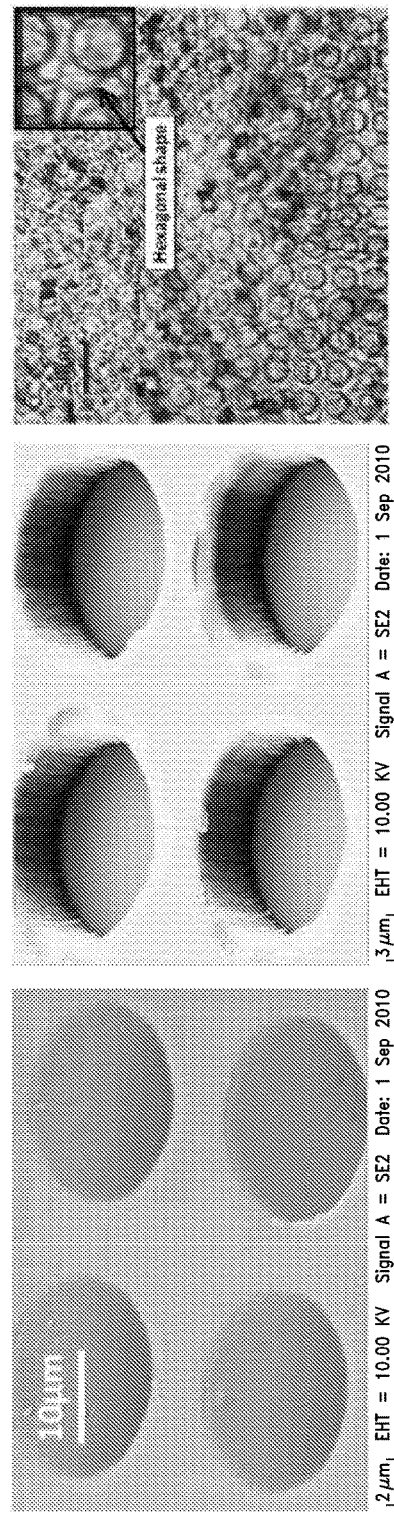
FIGS. 21A-21C depict various substrate embodiments disclosed herein.

As shown in FIGS. 21A-21C, such substrates having an apical cell growth surface and basal structural support surface can be fabricated by the methods disclosed herein and support cellular growth. FIG. 21A depicts a scanning electron microscopy image of the apical cell growth surface of an substrate in accordance with the above description. As shown, the apical cell growth surface is homogenous, while, as shown in FIG. 21B, the basal surface is inhomogenous, comprising multiple support structures. Further, as shown in FIG. 21C, the apical cell growth surface is suitable for the growth of cells, e.g., stem cells (shown are H9 hESC-RPE cells proliferating on a parylene growth surface).

As discussed above, the particular tissue that is damaged or diseased and is to be targeted with a cell-loaded substrate may define the dimensions or structural features of the substrate. For example, a substrate used to target cells to the surface of an individual's liver could be fabricated with much larger dimensions than those described above. Similarly, a substrate fabricated to target the cardiac tissue of a patient could also be designed with larger overall dimensions. However, some substrates, such as those to target neural tissues, may benefit from dimensions more similar to those described above. Given the anatomical knowledge of those skilled in the art, dimensions for various target tissues can be readily obtained, or as discussed herein, specifically measured for a certain individual.

Porosity and Permeability

With reference to FIGS. 1 and 2, in several embodiments, the substrate cages comprise porous materials. In some embodiments, the material is a permeable material. As shown, pores 60 are present in the outer shell of the substrate cage. In some embodiments, pores are present on the top 30a and bottom 30b surfaces of the substrate cage. As used herein, the term pore shall be given its ordinary meaning and also refer to "biological vias", in the sense that they function as passageways to allow the physical, chemical, or other types of interactions and/or interconnections described herein. The terms "pore" and "via" shall be read as interchangeable unless contextually indicated otherwise. In some embodiments, the vias on the top side of the substrate cage allow the passage of apical microvilli from cells contained within the substrate cage, while vias on the bottom side provide support for the cell bodies. In some embodiments, the density of pores on the top and bottom sides is similar, while in other embodiments, the pore density is different.

In several embodiments, pore density ranges between about $1 \times 10^6$ and $2.5 \times 10^9$ pores per $cm^2$. In some embodiments, pores have a distance between them of approximately 0.2 microns and about 2 micron center-to-center pitch. Greater or lesser spacing and pitch is used in other embodiments. In several embodiments, the parameters described above (pore diameters, density, and substrate thickness) affect the hydraulic conductivity and diffusion rate of nutrients and macromolecules across the substrate. In one embodiment, net flux across both substrates is zero. As such, in several embodiments, the bottom surface has a higher pore density compared with the top. To this end a dual layer photolithographic process flow allowing for decreased allowable effective pore diameter defined by sacrificial layer thickness can be employed for fabrication of the basal substrate. In some such embodiments, a first layer of material is fabricated with passages that communicate with either surface of the layer. This results, in cross-section, in a "block-like" pattern. See e.g., FIG. 10. There after a second layer is fabricated, again with similar passages. In order to maintain the desired pore diameter, the second layer is photolithographically laid onto the first layer with a known gap size 60 that corresponds to the desired size of the biological via.

In still other embodiments, vias are present only on one of the sides, e.g., top or bottom. In some embodiments, although not expressly shown in the Figures, the apical and/or basal surface further comprises a separate substrate material that is annealed to the apical or basal surface during the fabrication process. In several embodiments, the vias range in diameter from about 0.5 to about 10 µm. Pore diameter may vary depending on the cell type to be housed within the substrate cage, the site of implantation, or the target tissue. In several embodiments, the pore diameter ranges from about 1 to 3 µm, 3 to 5 µm, 5-7 µm, 7 to 10 µm, or overlapping ranges thereof. In several embodiments, the pore diameter ranges from about 0.5 to about 1.5 µm, including 0.6, 0.7, 0.8, 0.9, 1.0, 1.1, 1.2, 1.3, and 1.4 µm. While in several embodiments, the pore diameter is sufficiently large to allow cellular process to reach out of the substrate cage to the target tissue, the pore diameter is not large enough to allow the cell itself to escape the substrate cage. Thus, via diameter serves to retain the cells within the substrate cage, but allows the therapeutic effect of the cells to reach the target tissue, whether this be a physical (e.g. between a cellular process and the target tissue), chemical, or other type of interaction. However, in some embodiments, substrate cages are designed to let at least a portion of the cells within the substrate cage escape.

In several embodiments, the pore diameter is varied across the surface of the substrate cage during the fabrication process. In several embodiments, pore size may be varied to allow cells at a certain position in the lumen of the substrate cage to escape while other cells are retained within the substrate cage. In some embodiments, the substrate cage is fabricated with multiple chambers, and pore size may vary depending on the chamber the pore is in communication with. For example, a first chamber may house a first cell type to be retained within the substrate cage and provide a therapeutic effect to the target tissue. In such embodiments, the first chamber would be fabricated with a pore size that retained the cells within the substrate cage. See, for example FIG. 2B chamber 50a and pore 60a. However, a second cell type may be housed within a second chamber, the second cell type providing an ancillary effect to the first cell type and/or the target tissue upon escape from the substrate. Thus, in such embodiments, the second chamber would be fabricated with pores of a diameter sufficient to allow the second cell type to escape the substrate cage. See, for example, FIG. 2B, chamber 50b and pore 60b. In other embodiments, different chambers may house drugs or other ancillary agents, and are therefore fabricated with a porosity defined by the required or desired release rate of the drug or agent. In some embodiments, additional chambers are not required for a drug or ancillary agent. The drug or ancillary agents are used to support the viability of the cells, promote the interaction of the cells with the target tissue, inhibit or promote vascularization of the substrate or tissue near the substrate (depending on the target tissue) or other additional effects that potentiate or otherwise enhance the therapeutic effects of the cells on the target tissue.

Figure 4:
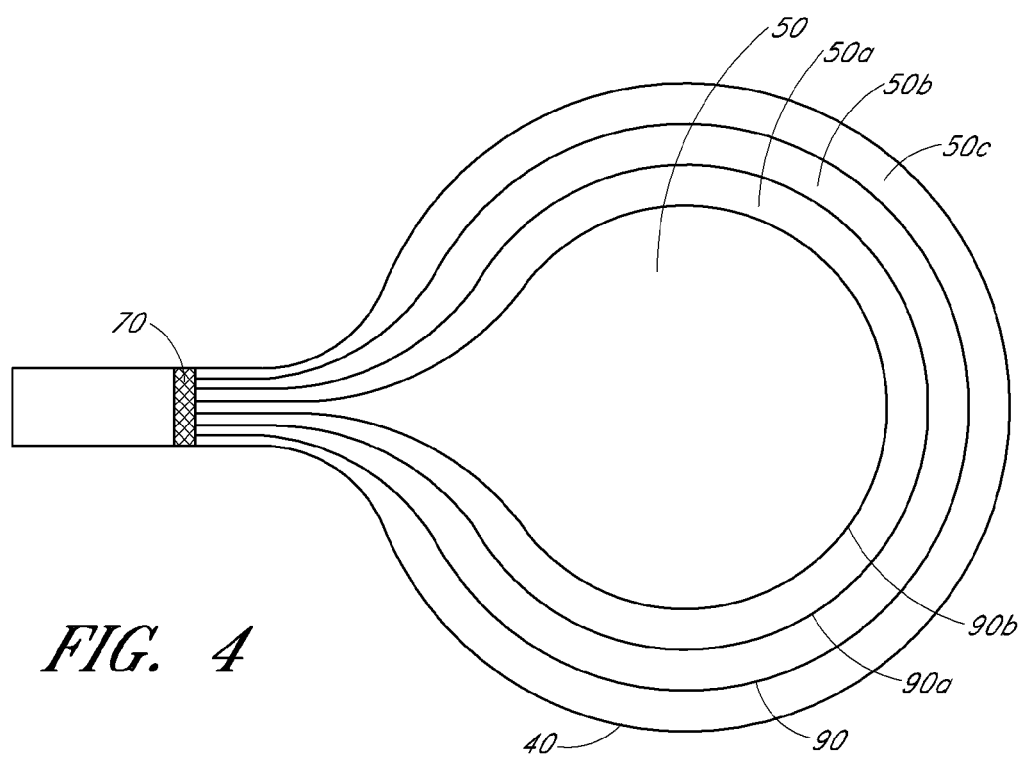
FIG. 4 depicts a representation of an substrate cage with customizable chambers in accordance with several embodiments discloses herein

With reference to FIG. 4, different chambers 50, 50a, 50b, and 50c may also be fabricated in a concentric or semi-concentric manner. The individual chambers are created by dividers 90, 90a, and 90b. In several embodiments, the dividers comprise the same material as the body of the substrate cage. In several embodiments, dividers are constructed of a different material from the body of the substrate cage. In some embodiments, the dividers comprise wires through which an electrical current may be passed to create and seal off a chamber from the remainder of the lumen of the substrate cage. In other embodiments, the materials that generate the chambers may be altered to allow for visualization of the substrate cage in situ. For example, 90, 90a, and 90b, may comprise a ring of chromium or other compound that allows visualization. These structures may also function as connectors for chemical sensors that allow reporting of information regarding the environment around the substrate (below). Further, they could function as a mechanism to secure an apical and basal portion of an substrate to one another, either before or after the seeding of the cells.

In several embodiments, the substrates are non-porous. As used herein, the term non-porous shall be given its ordinary meaning and shall also refer to a substrate which has not been treated or manufactured in a way that results in the generation of an orifice, via, or direct passageway that passes through the thickness of the substrate material. While lacking a specific passageway for passage of nutrients or cell processes, non-porous substrates have a permeability that can be manipulated based on the thickness of the material used. For example, the thickness of the substrate material allows the substrate to act as a molecular sieve, keeping certain proteins of a certain size from passing through the substrate, while allowing passage of proteins of other sizes through the substrate. See FIGS. 20E and 20F that depict data related to the diffusion of molecules (dextran) through substrates ranging from 0.15 to 0.80 µm in thickness. Diffusion coefficients (related to thickness) range from between about $10^{-10}$ and $10^{-13}$ cm$^2$/second. In some embodiments, greater or lesser rates of diffusion can be achieved by manipulating the thickness of the substrate.

As discussed above, several asymmetrical, inhomogeneous substrate embodiments (those with an apical cell growth surface and an inhomogeneous basal surface) are non-porous, but are permeable. A certain degree of permeability of the substrate material is necessary to support the cells grown on the substrate such that they are both metabolically and functionally viable over time (e.g., both in culture and post-implantation). For example, in several embodiments, parylene substrates having a thickness (e.g., D14 in FIGS. 20A-20B) less than about 0.80 µm have a molecular weight exclusion limit of about 70-75 kDa. Such a substrate would exclude proteins or molecules larger than about 70-75 kDa, which would allow for the passage of most proteins present in the bloodstream that would be necessary to support cells on the substrate after implantation. In some embodiments, greater or lesser molecular exclusion can be achieved by manipulating the thickness of the substrate (e.g., exclusion limits ranging from about 25 kDa to about 150 kDa, including about 25 to about 50 kDa, about 50 to about 75 kDa, about 75 to about 100 kDa, about 100 to about 125 kDa, about 125 to about 150 kDa, and overlapping ranges thereof.

While it is appreciated in the art that delivery of nutrients to implanted (and existing cells) is important for the viability of the cells, it is particularly advantageous that certain embodiments of the substrates disclosed herein do not require a pore or an orifice to provide such nutrients. For example, wet AMD involves anomalous neovascularization by vessels that have mechanically weaker walls. This fragile vasculature risks rupture, subsequent hemorrhage, and the rapid loss of vision due to cell death. Such rupture could be compounded by the implantation of substrates having pores, through which such fragile vessels could grow. While dry AMD is non-neovascularizing disease, in some instances, the growth of vessels through the pores of a substrate cage could result in damage to the vessels, or disruption of the cells within a substrate cage. As discussed above, certain embodiments comprise non-porous substrate cages that are permeable to nutrients from the bloodstream. In such embodiments, pores in the substrate cage as well as the growth of vessels into such pores, is not possible, thereby limiting the possibility of blood vessel rupture and/or disruption of the cells growing on the substrate cage.

In some embodiments, certain materials may be used that are both permeable and porous. Selection and/or adjustment of the formulation of selected materials (e.g., co-polymers) are used, in some embodiments, to tailor the permeability and/or the porosity of the materials (and the resulting substrate).

Materials

A variety of materials may be used to fabricate the substrates disclosed herein. In some embodiments, the substrates are biodegradable while in other embodiments, the substrates are non-biodegradable. In still other embodiments, a portion of the substrate is biodegradable while another portion is not. In several embodiments, the biodegradable portions of the substrates can be fabricated to degrade at a known rate. Such biodegradable materials include any suitable material that degrades or erodes over time when placed in the human or animal body. Accordingly, as the term is used herein, biodegradable material includes bioerodible materials.

In several biodegradable embodiments, the materials selected are optimized to accomplish a particular rate of biodegradation. For example, in several embodiments employing polymers, the composition of the polymers is controlled to achieve a certain rate of biodegradation, and hence residency time of the substrate in vivo. By way of example, in one embodiment in which the substrate comprises a PLGA co-polymer, the rate of biodegradation of the PLGA copolymer is controlled by varying the ratio of lactic acid to glycolic acid units in the copolymer. In some embodiments, the rate of biodegradation is controlled to achieve a residency to of approximately 4 weeks post-implantation. In some embodiments, the substrate degrades in about 1-3 weeks, 2-4 weeks, or longer, including from about 4-6 weeks or several months.

In addition to the materials used to fabricate the substrate itself, several embodiments comprise an additional biodegradable layer or coating that functions to delay the interaction between the target tissue and the cells housed within or on the substrate for a known period of time. For example, a coating with a rapid rate of degradation could be used to encapsulate the substrate and thereby protect the cells within or on the substrate during the implantation process and/or prevent the pores of the substrate from becoming obscured or blocked with tissue during the implantation process. Upon completion of implantation, the layer would rapidly degrade and the interaction between the cells within or on the substrate and the target tissue would commence. In contrast, in some embodiments, a more slowly degrading coating may be used. For example, if the implantation procedure was performed as a surgical procedure (or in conjunction with a surgical procedure), post-surgery medications (e.g., anti-inflammatories and/or antibiotics) which may adversely affect the cells within or on the substrate may be present for an extended period of time at or near the target tissue. In such cases, the degradation rate of the coating could be tailored to prevent the exposure of the cells to the target tissue until a time when the harmful agent was no longer present.

Some embodiments comprise a non-biodegradable material combined with a biodegradable material, the latter which provides additional structural and mechanical support aiding in substrate handling during cell seeding and culturing and/or during surgical insertion into a tissue (e.g., the subretinal space). The material may also be used to add mass to the substrate to assist in the same and/or to assist in orientation of the substrate. In several embodiments, the support is in the form of columns connecting the top and bottom portions of a substrate cage or on the basal portion of an inhomogeneous substrate. In other embodiments the support comprises an additional layer on the top or bottom of the cage or the basal surface of an inhomogeneous substrate.

The substrates may be formed of metals, polymers, plastics, or combinations thereof. In some embodiments, the material allows the substrate to have sufficient elasticity, flexibility and potential elongation to not only conform to the target anatomy during and after implantation, but also remain unkinked, untorn, unpunctured, and with a patent lumen during and after implantation. In several embodiments, substrate material would advantageously be processable in a practical manner, such as, for example, by molding, extrusion, thermoforming, and the like, as well as by the MEMS manufacturing methods discussed below.

The purpose of surface modification, in some embodiments, is to promote cell viability and attachment. This is done by functionalizing the surface. Towards this end, illustrative examples of suitable materials for the substrate include parylene polypropylene, polyimide, glass, nitinol, polyvinyl alcohol, polyvinyl pyrolidone, collagen, chemically-treated collagen, polyethersulfone (PES), poly(glycerol-sebacate) PGS, poly(styrene-isobutyl-styrene), polyurethane, ethyl vinyl acetate (EVA), polyetherether ketone (PEEK), Kynar (Polyvinylidene Fluoride; PVDF), Polytetrafluoroethylene (PTFE), Polymethylmethacrylate (PMMA), Pebax, acrylic, polyolefin, polydimethylsiloxane (PDMS) and other silicone elastomers, polypropylene, hydroxyapetite, titanium, gold, silver, platinum, other metals and alloys, ceramics, plastics and mixtures or combinations thereof. Additional suitable materials used to construct certain embodiments of the substrates include, but are not limited to, poly-para-xylylenes (e.g., parylene, including but not limited to parylene A, parylene AM, parylene C, ammonia treated parylene, parylene C treated with polydopamine), poly(lactic acid) (PLA), polyethylene-vinyl acetate, poly (lactic-co-glycolic acid) (PLGA), poly(D,L-lactide), poly (D,L-lactide-co-trimethylene carbonate), collagen, heparinized collagen, denatured collagen, modified collaged (e.g., silicone with gelatin), other cell growth matrices (such as SYNTHEMAX™), poly(caprolactone), poly(glycolic acid), and/or other polymer, copolymers, or block co-polymers, poly(caprolactone) containing cyclic Arginine-Glycine-Asparagine, cyclic or linear Arginine-Glycine-aspartic acid, blends of polycaprolactone and polyethylene glycol (PCL-PEG), thermoplastic polyurethanes, silicone-modified polyether urethanes, poly(carbonate urethane), or polyimide. Thermoplastic polyurethanes are polymers or copolymers which may comprise aliphatic polyurethanes, aromatic polyurethanes, polyurethane hydrogel-forming materials, hydrophilic polyurethanes, or combinations thereof. Non-limiting examples include elasthane (poly(ether urethane)) such as Elasthane™ 80A, Lubrizol, Tecophilic™, Pellethane™, Carbothane™, Tecothane™, Tecoplast™, and Estane™. Silicone-modified polyether urethanes may include Carbosil™ 20 or Pursil™ 20 80A, and the like. Poly(carbonate urethane) may include Bionate™ 80A or similar polymers.

Substrate Fabrication and Manipulation

Depending on the materials selected and the type of substrate to be fabricated (e.g., 3-D substrate cage or asymmetric inhomogeneous substrate), various techniques may be used to fabricate the devices. It shall be appreciated that the procedures listed herein are not exhaustive not meant to be interpreted as an exclusive list. Additional techniques known in the art, but not expressly disclosed herein may also be used to fabricate several embodiments of the invention. It shall also be appreciated that several embodiments of the substrates disclosed herein comprise combinations of materials, and therefore combinations of fabrication techniques may be used.

In several embodiments, the substrate is fabricated by extrusion, drawing, injection molding, sintering, micro machining, laser machining, and/or electrical discharge machining, or any combination thereof. In some embodiments, 3-dimensional substrates are fabricated as a single piece, however in several embodiments, the substrate is fabricated modularly. For example, in one embodiment, the top and bottom portions of a 3-dimensional substrate cage are fabricated independently of one another. Such an approach is advantageous in the production of substrates that differ from one another in one or more aspects (e.g., a first substrate has porous apical and basal surfaces and a second has a non-porous apical surface), but retain the same overall dimension. In such embodiments, the desired modular pieces may be selected and then assembled into a complete 3-dimensional substrate cage. After the desired modular pieces have been selected, they are aligned and sealed to create a 3-dimensional substrate cage with the desired dimension and characteristics. In some embodiments, a 3-dimensional substrate cage fabricated from a single piece is also sealed. For example, in one embodiment, the top and bottom portions are formed as a single flat piece and then one portion is folded over the other and the resultant 3-dimensional substrate cage is sealed. Sealing may be accomplished with heat welding, annealing, biocompatible adhesives or epoxies, and the like. Some embodiments optionally include a shell or frame comprising additional material that does not function as a cell growth surface. In some embodiments, the shell or frame provides a user one or more places to grip and or manipulate the substrate without damaging the cell growth surface and/or the cells growing on said surface.

While 3-dimensional substrate cages that function to foster interaction between the cells and the target tissue while retaining cells in the cage post-implantation are preferred in several embodiments, as discussed above, several embodiments comprise a substrate material (e.g., a biodegradable material) having at least one homogeneous cell growth surface and additional features for structural support. Some such embodiments are advantageous in that their production may be simplified as compared to a 3-dimensional substrate cage. Moreover, in several embodiments, substrates with one homogeneous apical cell growth surface are suitable for positioning in a target site in a manner that still retains the cells on the homogeneous (apical) surface of the substrate and facilitates the therapeutic interaction with the target tissue. In other words, the lack of a 3-dimensional or cage-like structure does not reduce the therapeutic efficacy of substrates as disclosed herein.

In several embodiments, manufacturing of a plurality of substrates (or the modular portions thereof) is accomplished simultaneously. In some embodiments, the cells to be used for therapeutic effect are grown on the material that comprises the substrate (or a portion thereof) prior to the final fabrication of the substrate. In some embodiments, the substrates (or modular portions thereof) are effectively used as an in vitro culture substrate for the cells and at an appropriate time, are processed through the final phases of fabrication (if any are needed, depending on the embodiment) and ready for in vivo implantation with the cells pre-loaded in or on the substrate. For example, in one embodiment, a large sheet of polymer material is used as a substrate to grow a plurality of cells to be delivered in controlled laboratory conditions. When the cells are determined to be in an optimal state for delivery (e.g., a certain phase of cell cycle or a certain population density), a plurality of individual substrates are removed from the polymer sheet, sealed and ready to be implanted.

Several embodiments with homogeneous apical surfaces are particularly amenable to seeding and growth of cells simultaneously on a plurality of substrates, which are joined during the culturing process and are separated into individual substrates prior to insertion or implantation. For example, as shown generally in FIGS. 18A-18C, multiple substrates can be fabricated from one contiguous piece of the chosen material (e.g., a biodegradable polymer; hereafter referred to as the frame). As shown in FIG. 18A, a single circular frame is capable of providing mechanical support for multiple individual implantable substrates. In several embodiments, each substrate is attached to the larger frame via an extension (e.g., a handle; see generally FIGS. 18B and 18C). Dimensions of the substrates and handles are described in greater detail above. In several embodiments the handle of the substrate is free of cellular growth, allowing for manipulation and loading onto the custom surgical tool using custom forceps without disrupting monolayer integrity.

Figure 18D:
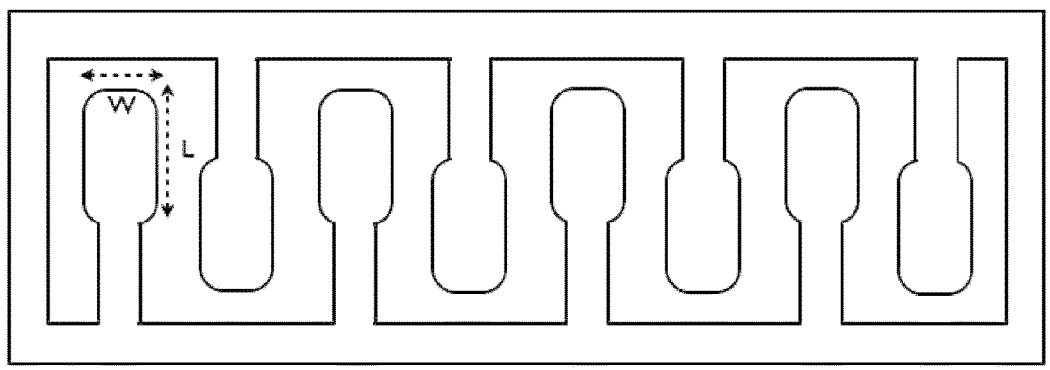

In several embodiments, the frame is dimensioned to maximize the surface area available for growth of cells seeded onto the substrate. For example, the frame may optionally be made in a rectangular shape and be comprised of a plurality of rectangular substrates. In one embodiment the rectangular substrates plus frame taken together maximize polymer to exposed culture dish surface area ratio by employing an interdigitating "comb-like" structure (see e.g. FIG. 18D). It shall be appreciated that this figure is merely representative and a greater or lesser number of implants can be used, depending on the embodiment. In several embodiments a circular frame is preferred, as such frames can be dimensioned to fit within a standard cell culture dish (e.g., a 10 cm dish). In such embodiments, the close juxtaposition of the edges of the frame with the walls of the culture dish reduce flow and turbulence of the culture media over the cell growth surface, which can disrupt the integrity of certain growing cell populations. In some embodiments, larger or smaller diameters of substrate frame are used (e.g., diameters between about 5 cm to about 10 cm, from about 6 cm to about 9 cm, from about 7 cm to about 8 cm, and overlapping ranges thereof (frames may also be sized to fit in any variety of culture vessel as described herein).

As discussed herein, the plurality of individual substrates can be fabricated from a single, larger substrate frame using photolithographic techniques, injection molding, and the like.

Also as discussed herein, the individual substrates may be, without limitation, circular, oblong, or any shape customized to a specific to individual patient pathology (see e.g., FIGS. 5-8). Customization of substrates is described in more detail below, by can be determined by electrophysiological testing (e.g. mfERG), psychophysical testing (e.g. kinetic or static microperimetery), or various ocular imaging modalities (i.e. spectral-domain optical coherence tomography (SD-OCT), fundus photography, fundus autofluoresence (FAF), or confocal scanning laser ophthalmoscopy (cSLO).

In several embodiments, the substrate frame is not designed to necessarily optimize or maximize a contiguous cell-growth surface, but rather is configured to allow selection and removal of a single substrate without disturbing other substrates on which cells are still growing. As shown generally in FIG. 22A, in some embodiments, a plurality of substrates 10' are fabricated on a single circular frame 130 positioned in a manner which allows the handle 30' of the substrate to be accessed by a manipulation tool (e.g., forceps). Once fabricated, a single circular substrate can then be seeded with cells (e.g., H9 hESC-RPE) and cultured until such time that the cells have reached an optimal growth state (e.g., a confluent monolayer over the substrate). Individual oblong substrates are then cut from the larger frame using a sterilized and autoclaved pair of scissors or a custom designed holding/cutting tool. In several embodiments, each substrate comprises an identifier 155' to aid the surgeon in orienting the substrate. In some embodiments, the identifier comprises a visual or chemical indicator (e.g., a fluorescent dye that can be visualized). In some embodiments, a MEMS reporting system is employed, and can report the viability of the cells or other local environmental conditions around the substrate. In several embodiments, a metal boundary or point is embedded into the substrate. Suitable metals include, but are not limited to nitinol, titanium, gold, silver, platinum, other metals and alloys, foils made from the same, and the like. In some embodiments, the substrates are doped with a fluorophore for imaging the substrate. In such embodiments, the loss or migration of cells from the substrate could be identified post-implantation or post-operatively, thus providing a means to assess the quality of the implantation procedure and to determine whether an alternate or additional substrate should be implanted. In some embodiments, the substrates further comprise a bar code or other unique identifier for quality control lot/batch information and inventory purposes.

A non-limiting example of a custom holding/cutting tool 140 is shown in FIG. 22B. The cutting tool in fact functions in multiple additional ways, beyond simply enabling the cutting of an individual substrate from the frame. For example, in several embodiments the tool functions as a weight that holds the substrate frame in position within a culture vessel. In several embodiments, the holder/cutter device is reversibly attached to the underside of a tissue culture dish. In several embodiments, the holder/cutter device is integrated into the underside of a custom tissue culture dish. In such embodiments, the holder/cutter is advantageously pre-sterilized. In some embodiments, this is particularly advantageous, as some cell types require a greater media volume, which increases the flow of media throughout the vessel during normal handling. Such fluid flow could disrupt the integrity of growing cell populations, thereby increasing the overall time to prepare an substrate for implantation and/or adversely affecting the viability of the cells on the substrate. Further, the tool allows for the consistent and repeatable cutting of individual substrates.

Moreover, the tool, as it has a plurality of contact points 150 with the frame, prevents the growth of cells on a portion of the handle of the substrate. This cell-free portion is the portion which is grasped by manipulating tools (e.g., forceps) that are used in some embodiments. In such embodiments, the use of forceps does not disrupt the cells growing on the substrate growth surface, thereby maintaining the integrity and viability of the cells during the transition from the culture vessel to the target site of a subject. Each contact point also comprises a slot or aperture 151 that is dimensioned to allow a cutting device (e.g., a scalpel or custom designed sterilizable blade) to be inserted through the contact point and cut the underlying substrate handle, thereby freeing the individual substrate from the frame. The associated cutting point on the substrate frame is shown as 151' in FIG. 22A.

In some embodiments, substrates that are cut from the frame are manipulated and implanted with a specialized tool, which is described in more detail below.

Arrangements comprising a plurality of substrates within a frame are advantageous in some embodiments, because of the plurality of substrates, a certain number substrates may be used for release testing of the lot (e.g., assays testing genotype, phenotype, and function), which consists of one or multiple circular frames, while another portion of the substrates can be retained for implantation in a subject. Moreover, such a layout enables evaluation of each of the substrates in the frame for identification of the substrate that best suits a particular implantation procedure (e.g., has appropriate cells numbers, cell density, etc.) and subsequent selection of that substrate, without perturbation of the other substrates in the frame.

Fabrication of a plurality of substrates with cells pre-grown on the material provides certain additional advantages in some embodiments. In one embodiment, the possibility of contamination of the cells is minimized because the cells (and the material they are grown on) are already in sterile culture conditions and manipulation prior to implantation is limited.

Moreover, in some embodiments, growth of cells on a plurality of substrates allows the selection of the most healthy and viable cell populations prior to implantation. Additionally, those cells that are not optimal at the time of evaluation need not be discarded, but can be cultured for a longer period of time and/or under different conditions, until such time as they are optimal for implantation. In some embodiments a single point of connection between each substrate and the larger frame aids in simple cutting or dislocation of the substrate prior to surgery, further minimizing possible contamination of or damage to cells compared with similar designs requiring the full stamping-out or cutting of the substrate along it's entire perimeter (which may compromise the health and/or integrity of one or more cells on the substrate periphery). Furthermore, scale-up in manufacturing of a plurality of substrates with cells pre-growing is easily accomplished.

In addition to the methods used in the fabrication of the substrate, in some embodiments, additional processes are employed to further adapt the substrate, or the materials the substrate is fabricated from, to the particular cells to be used or target tissue. For example, in one embodiment, a polymer substrate, such as parylene, is used to fabricate the substrate. In one embodiment, the material surface that will form the cell substrate of the fabricated substrate is hydrophilically modified using oxygen treatment. This hydrophilic treatment generates an ideal surface for certain cell types to grow on.

In some embodiments, oxygen plasma treatment is performed using a reactive ion etch (RIE). The etch is performed for two minutes at a power of 100 W and a maintained O2 chamber pressure of 200 mTorr. In several embodiments, surface modification of parylene-c allows for the surface to remain hydrophilic for an extended period of time compared with other commonly used biocompatible polymers. $O_2$ plasma treatment will allow, in some embodiments, for maximal density of seeded cells, thus increasing the effective dose of the therapeutic to the targeted area.

For example, retinal pigmented epithelial cells (RPE) grow particularly well on a hydrophilic surface, as the RPE cells are polarized and thus orient themselves with respect to the hydrophilic surface. In several embodiments, the substrate enhances the ability of cells seeded thereon to polarize, thus reducing the likelihood of shedding or migration off the substrate during the delivery process.

In several embodiments, one or more surfaces of the substrate are altered to enhance handling and/or visualization of the substrate. For example, the outer surfaces of the substrate may be etched in order to roughen the surface. The rougher surface, in some embodiments, provides a surface which diffracts light to a greater degree than a smooth substrate surface, which reflects light. In some embodiments, this diffraction of light allows a user to visualize the substrate and/or tissues underneath or distal to the substrate more clearly.

MEMS Features

As discussed above, in several embodiments, the substrate are MEMS devices and/or incorporate MEMS technology. In several embodiments, the substrate comprises a central unit for data processing, one or more microsensors that evaluate the cellular environment within the device and or surrounding the target tissue. In several embodiments, the substrate further comprises a reporting unit that indicates certain information about the environment surrounding the substrate or the cells within the substrate. In some embodiments, the substrate reports on the viability or metabolic condition of the cells within the substrate. In some embodiments electrodes can be used to report the electrical impedance value at the device-tissue interface, and quantify proximity and/or mechanical force and pressure. These electrodes are also used, in some embodiments, to measure oxygen concentration and/or to measure blood flow. In some embodiments, the substrate reports on the degree of interaction between the cells within the substrate and those of the target tissue. For example, in certain ocular embodiments, the device reports to a user information regarding the degree of physical interaction taking place between the RPE cells within the device and target photoreceptor cells. In some embodiments, Fast CV is used to monitor the basal concentrations of electroactive species (as discussed above) to assess the health of the cells and tissues. This is advantageous in some embodiments, because photo-oxidative stress is a known cause of AMD and the device would be implanted close enough to the choroid to measure rate of blood flow. Moreover, in several embodiments, the device allows for assessment of underlying cellular morphology and health through the use of advanced imaging tools (e.g., spectral-domain optical coherence tomography (SD-OCT), fluorecein angiography (FA), fundus photography, SD-OCT supplemented with adaptive optics (AO-SD-OCT). In one embodiment, the boundary between RPE cells within the device and the endogenous photoreceptors (the PR-RPE-choriocapillaris boundary) is visible using long-wavelength SD-OCT imaging, thereby enabling adequate assessment of the ability of the cells to restore function.

In several embodiments, the substrate is configured to electrochemically detect electroactive species (e.g., neurotransmitter concentration, such as noradrenalin (norepinephrine), adrenaline, serotonin and dopamine). In some embodiments, fast cyclic voltammetry, proximity to tissue measurement using impedance, or other similar electrochemical detection methods are used to allow the device to report on the presence and/or concentration of electroactive species.

In several embodiments, the features of the substrate described herein facilitate the use of imaging techniques. In particular, ocular imaging techniques are used in some embodiments. In some ocular-directed embodiments, for example, the features of the device allow the assessment of the health of endogenous RPE and PR. Optical coherence tomography (OCT) is used in some embodiments and allows non-invasive imaging (e.g., without injection of dyes or radioactive labels) with a high degree of resolution. Such techniques allow for the imaging of about 10-100 cells in an intact eye. Moreover, advanced imaging techniques allow for the assessment of blood flow dynamics at the capillary level that supports RPE cells (choriocapillaris), and also the assessment of bleaching and rejuvenation of photoreceptor visual pigments; both of these are important metrics of the functionality of the RPE-PR complex.

Advantageously, many of the materials used in traditional MEMS devices are those described herein as being suitable for fabrication of the substrate. For example, the MEMS components of the device may be fabricated from, for example, polymers, silicon, or various metals. In those embodiments in which polymer-based MEMS devices are fabricated, processes such as injection molding, embossing or stereolithography may be used. In those embodiments in which silicone-based MEMS devices are fabricated, procedures such as deposition of material layers, patterning of the layers by photolithography, and then etching to produce the required shapes. In those embodiments in which metal-based MEMS devices are fabricated, procedures such as electroplating, evaporation, and/or sputtering may be used. Other processes such as molding and plating, wet etching or dry etching, electro discharge machining (EDM), and other similar processes known in the art are used in several embodiments.

In several embodiments, MEMS features are used to anchor a device to a target tissue. In some embodiments, MEMS latches or clamps are used to grasp the surface of a target tissue.

Custom Fabrication

In several embodiments, substrates are custom fabricated depending on the disease to be treated and the particular characteristics or symptoms of the individual afflicted with the disease. In several embodiments, a physician will make a determination regarding the distribution of damaged or diseased cells in particular patient. As a result, a customized substrate is generated that places the substrate and the cells associated with the substrate in the regions correlating to the damaged or disease cells.

Figure 5:
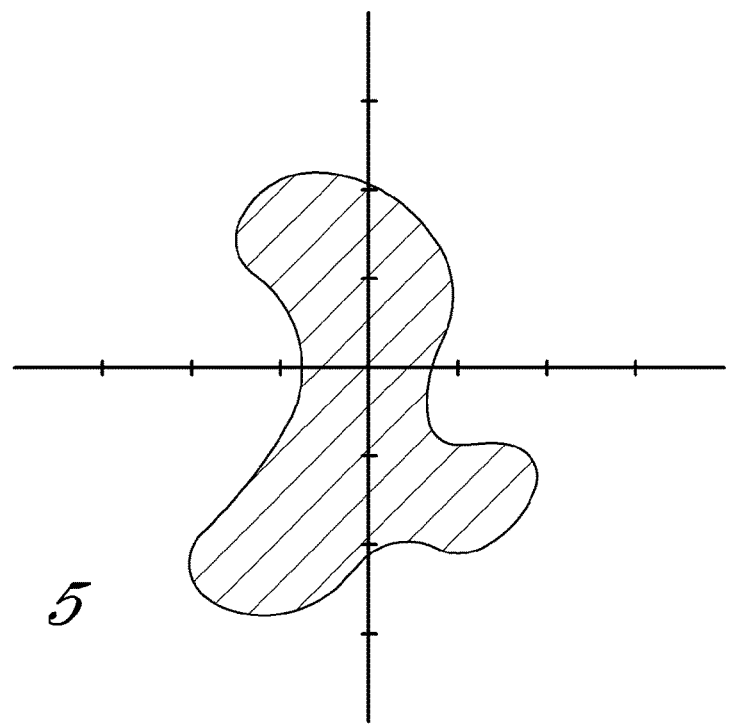
FIG. 5 depicts a representation of a patient's visual field used in fabricating a customized substrate cage according to several embodiments disclosed herein.
Figure 6:
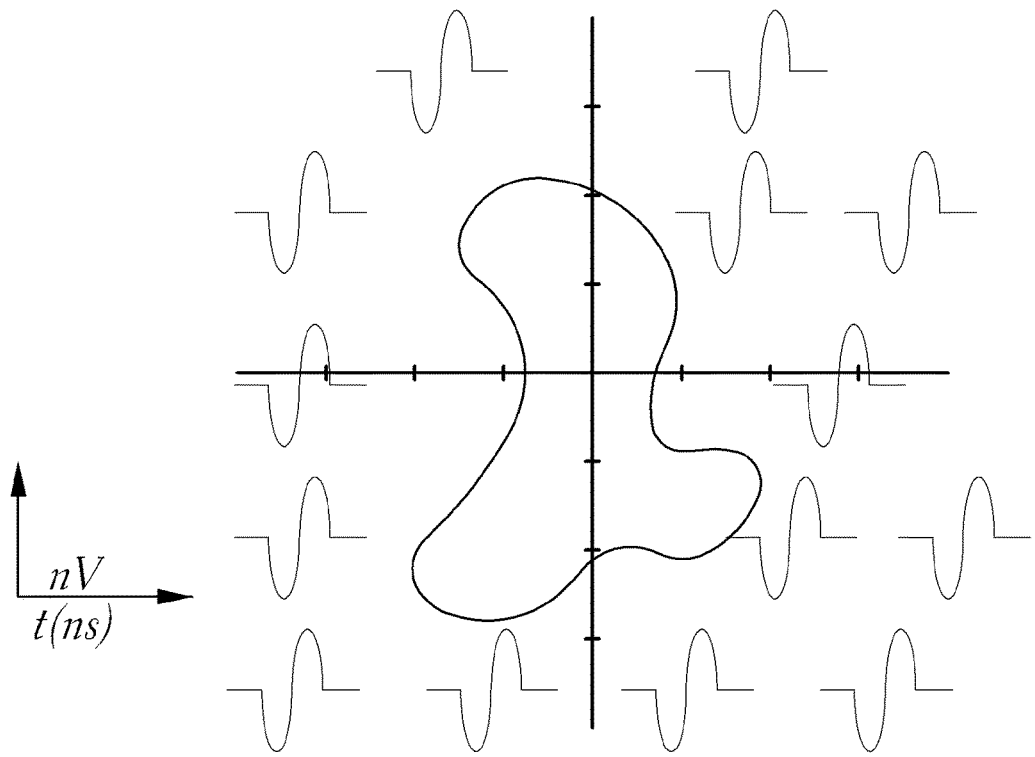
FIG. 6 depicts an example of a scotoma map used to construct a custom ocular substrate.

For example, in ocular applications, the visual field of a patient can be determined by any appropriate known diagnostic techniques, such as Goldmann kinetic perimetry (see, e.g., FIG. 5). Thereafter (or in place of), local visual function can be determined by any appropriate known technique, to generate a multi-focus electroretinogram (see, e.g., FIG. 6). With this data, a custom substrate can be fabricated that places cells in juxtaposition to the area of lost or diminished visual function, that area corresponding to dead or functionally damaged photoreceptors.

Figure 7:
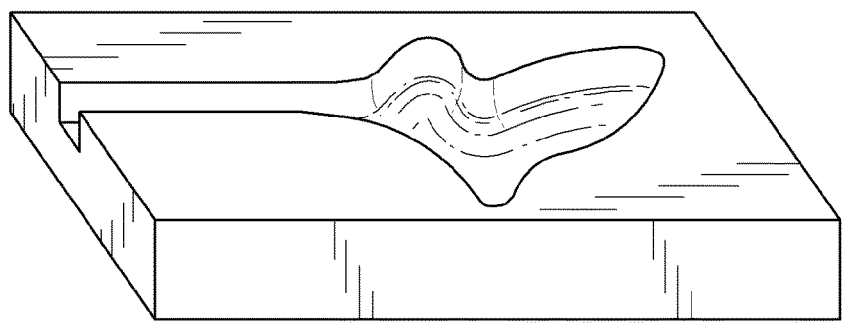
FIG. 7 depicts a mold shell used in several embodiments of fabrication of a custom substrate.
Figure 8:
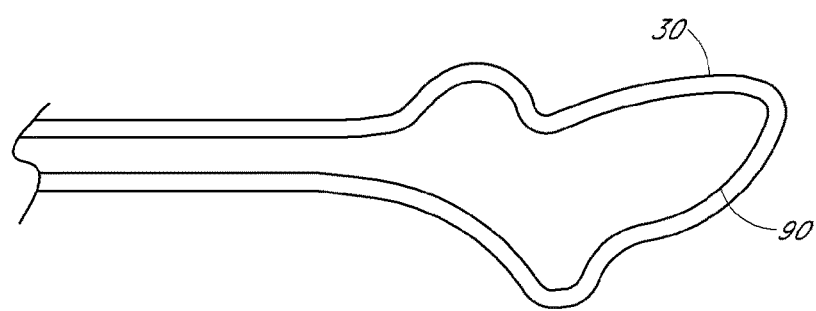
FIG. 8 depicts an example of a custom fabricated substrate constructed according to methods disclosed herein.

In several embodiments, an injection mold is formed based on the determination of an individual's visual field/visual function (see e.g., FIG. 7). In some embodiments, the mold comprises plastic, aluminum, or other easily workable (e.g., machinable) materials. In some embodiments, the mold can be stamped or shapes from elastomeric materials in a photographic process flow. In several embodiments, the materials are spin coated onto larger discs of material prior to stamping, thereby generating more uniform thicknesses in the resultant stamped substrate. In some embodiments, the mold form corresponds to the apical or basal surface of the substrate. The material of choice for the substrate, for example parylene (or other suitable material described herein) is shaped to the mold. In one embodiment, a solution of parylene polymer molecules is deposited into the mold and UV cured. The apical and basal surfaces are thereafter aligned and sealed, as described herein. In several embodiments, a metal trace is deposited on the apical and basal surfaces of the substrate (e.g. around the perimeter) to enhance alignment and sealing of the two portions of the substrate (see element 90 in FIG. 8). In some embodiments, a platinum trace is deposited on the substrate halves by electron beam evaporation followed by electrochemical platinum deposition. In some embodiments, an Indian-tin oxide is deposited with sealing of the halves accomplished by flip-chip bonding. In several embodiments, MEMS latches are used to attached the various substrate components to one another. Other metal traces and bonding techniques known in the art are used in other embodiments. Not only does this metal trace provide enhanced alignment of the halves of the substrate, it also optionally provides additional thickness (depending on the amount of metal deposited) and adds structural support to the substrate (e.g., to prevent folding or crimping during the implantation process).

In several embodiments, the cells housed in such a substrate cage for ocular therapy are RPE cells. It shall be appreciated that RPE cells are also used in other non-cage embodiments. Substrates in accordance with several embodiments described herein are particularly advantageous for use in ocular applications, as the function of damaged photoreceptors can be supported (e.g., function is regained or further loss of function is prevented and/or minimized) by a physical interaction between the RPE cells retained within the substrate and the photoreceptors; RPE engraftment is not required.

In several embodiments, the RPE stem cells are modified to secrete neurotrophic factors that further support survival of photoreceptor cells. In certain such embodiments, genes encoding one or more neurotrophic factors are cloned into the RPE cells prior to transplantation such that there is significant and enhanced protection afforded to the photoreceptor neurons. Examples of such possible factors include PEDF, CNTF, BDNF. Over expression of other genes may allow for enhanced function of RPE. Examples include: over expression of surface integrins (which have been shown to increase RPE adhesion to BM), melanin (ethnic groups with increased melanin production are at lower risk for AMD), or receptors required for phagocytosis of shed discs (e.g. CD36, MerTK). In some embodiments, over expression of receptors required for phagocytosis is advantageous because at the time of therapeutic intervention there is likely to be an accumulation of lipofiscin and metabolic waste products that would require removal.

In several embodiments, the substrates and cells housed therein are employed in the treatment of age-related AMD, and in several preferred embodiments dry AMD. Other approaches for treatment of dry AMD include macular translocation and autologous RPE transplantation. Both are complex surgical procedures requiring general anesthesia and both are associated with high rates of retinal detachment. Moreover, there are no FDA-approved, effective pharmacologic therapies for dry AMD. Multivitamins only slow the progression of early AMD. With regard to other cell therapy approaches, differentiation of hESC or retinal progenitors into photorecptors is complex, as implanted photoreceptors would have to integrate and form synapses with the host tissue. In contrast, the substrates disclosed herein allow the support of existing photoreceptors through the interaction between RPE cells within the substrate without the need for engraftment and/or synapse formation. Moreover, several embodiments of substrates disclosed herein promote the formation of a monolayer of cells within the substrate, which is advantageous as compared to a cell suspension. In some embodiments, a monolayer of cells on a substrate more closely mimics the structure of Bruch's membrane, which cannot, in AMD, provide a substrate for the attachment and further differentiation of injected cell suspensions. Thus, some embodiments of the substrates provide a synthetic replacement for the tissues damaged in AMD, rather than attempting to deliver cells that may not have an optimal tissue to attach to in vivo.

Cell Growth

In several embodiments, the substrate cages (and/or inhomogeneous substrates) are fabricated in a manner that provides an ideal surface and environment for the growth, survival, and function of cells. As discussed above, various characteristics of the substrates may be altered in order to surgical aspects of the substrate. To reiterate, the shape, thickness, pore diameter, and pore density are varied, in certain embodiments to optimally allow the housed cells to thrive and produce interactions with the target tissue, while being retained within (or on) the substrate. Thus, in some embodiments, the substrate confers the therapeutic benefit of the housed cells onto the target cells without the engraftment of the cells housed within the substrate. For example, in one embodiment, an epithelial layer of cells within the substrate (e.g., RPE) that are differentiated from hESC treat neurological degeneration (e.g., photoreceptor degeneration), without the need for synapse formation or neural integration. Moreover, these characteristics can be optimized to prevent migration of the cells out of (or off) the substrate and into the target tissue. Further, these characteristics may be varied in order to provide sufficient structure and resilience for the substrate to be implanted in vivo without damaging the substrate or the cells housed in the substrate.

As discussed above, the cell growth surface may also be altered (either before or after fabrication is complete) to optimize the surface for a particular cell type. In several embodiments, the cell surface is treated with oxygen to generate a hydrophilic cell growth surface on the substrate. In some embodiments, the oxygen treatment further comprises an additional compound, such as a matrigel, to support growth of polarized cells (e.g., RPE). In several embodiments, such matrigel compounds are xeno-free. Also as discussed above, in certain embodiments, the pore diameter may be adjusted depending on the cell type to be housed in the substrate.

In several embodiments, immunosuppressive agents are also delivered in order to avoid rejection of allogeneic cells introduced by the substrate. In some embodiments the substrate may be used to provide targeted and released delivery of these agents or drugs such as corticosteroids (e.g. prednisone), methotrexate, cyclosporine, antimetabolites, T-cell inhibitors, and alkylating agents. The administration of such immunosuppressive agents is used to avoid rejection of grafts or transplants or in treatment of autoimmune disorders. However, high-doses may be required, and oral administration, or even more localized and targeted delivery via injection, can be dangerous due to the increased risk of infection. In several embodiments, introduction of these agents via controlled and targeted release from substrates disclosed herein increases the likelihood of allogeneic graft acceptance, and minimize the risk of infection caused by immune suppression.

Other drugs that have been used clinical trials for treatment to AMD can be released by the substrate in a similar controlled and targeted manner by embedding in a biodegradable portion or in the interconnect case itself. Examples include lipid-lowering statins, retinoids (e.g. Acitretin, Alitretinoin, Bexarotene, Etretinate Fenretinide, Isotretinoin, Tazarotene, Tretinoin), and anti-VEGF drugs.

As discussed above, in several embodiments a second substrate is annealed to the primary substrate. For example, in some embodiments, a biodegradable substrate is employed. In one embodiment, a biodegradable polycaprolactone (PCL) material compounded polyethylene glycol (PEG) is used. The polymerizing PCL-PEG material is spin-coated onto glass coverslips to make thin films of a desired thickness. Upon treatment with aqueous buffer or media, the water soluble PEG is washed away and creates pores in the film. As discussed above, biodegradable embodiments may be customized, and in one embodiment, the ratio of the PCL to PEG affects the degradation rate of the substrate. As the PEG is washed away to form pores, the pores increase the surface area of the polymer exposed to water and therefore increase the degradation rate. Through this approach both the porosity of the films as well as the degradation rate can be manipulated based on the amount of PEG added to the polymer blend. In some embodiments, polymers with cyclic amino acids (Arg-Gly-Asp; cRGD) are annealed to the polymer film, thereby providing a polymer surface that promotes cellular adhesion and growth by mimicking the extracellular matrix protein, fibronectin.

Cell Loading

In several embodiments, cells to be used in or on the delivered substrate are cultured on the substrate prior to final fabrication of the substrate. As discussed above, this provides several advantages with respect to minimizing the risk of contamination or damage to the cells or the substrate. However, in several embodiments, the cells are deployed into or on a completely fabricated and sterilized substrate. Substrates as described herein may be sterilized by gamma irradiation, ethylene oxide, autoclaving, UV sterilization, or other known procedures without degradation or damage. Such cell deployment is carried out under sterile cell culture or sterile surgical suite conditions. Such embodiments have the advantage, among others, that optimally healthy and robust cells can be selected and deposited into the substrate just prior to implantation. For example, in several embodiments, cells are loaded into a 3-D substrate cage by a surgeon while in the operating room. This methodology is advantageous because a surgeon could select from several varieties of substrates, depending on patient characteristics or other parameters, and then load optimally healthy cells into the substrate. In some embodiments, a vacuum pressure device functions to assist the surgeon on holding and filling the substrate cage with cells. In several embodiments, this is advantageous because the vacuum pressure that holds the substrate cage also allows the volume of cell delivery fluid (that is potentially larger than the volume of cells) to be removed from the substrate cage through the biological vias. In some embodiments, the substrate is loaded into a surgical introducer and then loaded with cells. In some embodiments, the substrate is loaded with cells, then placed in the surgical introducer. In several embodiments using asymmetrical inhomogeneous substrates, cells are pre-seeded and stably growing on the apical surface of the substrate, before selection and subsequent implantation of the implant by a surgeon.

Figure 2B:
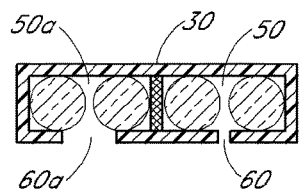
Figure 3:
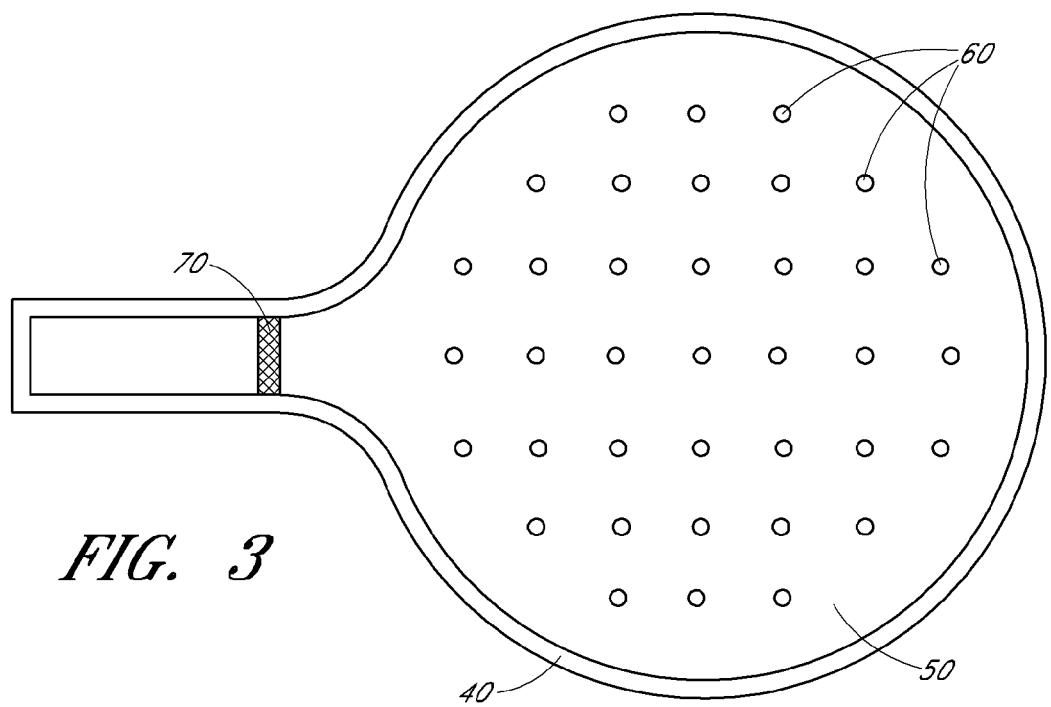
FIG. 3 depicts a top cut-away view of a substrate in accordance with several embodiments disclosed herein.

With reference to FIGS. 2A-2B, and FIG. 9, some embodiments of the substrate comprise a cell retention feature 70. Such a feature functions to provide a one-way passage for cells into the lumen 50 of the substrate cage. In several embodiments, the retention feature is custom shaped to provide an interlock with a pipette (or other device) 100 that delivers the cells into the lumen of the substrate cage. In several embodiments a resealable or "self-healing" membrane is used such that a pipette or needle can puncture through the membrane into the lumen for delivery of cells, but upon withdrawal of the pipette or needle, leaves no open orifice for cells to escape from. In some embodiments a viscoelastic is used. In some embodiments a biocompatible adhesive is used. In still other embodiments a one-way valve is used. Such a valve may comprises two or more flaps which open into the lumen upon advancement of a delivery pipette, which allows for the deposition of cells into the lumen. Upon removal of the pipette, the flaps return to their closed position, thereby retaining the deposited cells within the lumen. In some embodiments, the one way valve is formed such that a liquid tight seal is created to prevent backflow of cells, while in other embodiments, a fluid-tight seal is not formed.

Cell Types

Given the wide variety of diseases that induce cell damage or cell death, a wide variety of cell types can be housed within substrates described herein to achieve therapeutic effects. In some embodiments, cultured cells are used. In several embodiments, banked cells are used. In some embodiments, the cultured cells comprise stem cells. Stem cells are pluripotent cells capable of differentiating into a variety of different cell types. In some embodiments, embryonic stem cells are used, while in other embodiments, adult stem cells are used. In several embodiments, the embryonic stem cells are human embryonic stem cells. Embryonic stem cells, which are typically derived from an early stage embryo, have the potential to develop into any type of cell in the body. In some embodiments, H1, H7, H9, SHEF-1, or other similar FDA-approved stem cell lines are used. Adult stem cells are typically multipotent and can develop into a more limited number of cell types, typically those that are related to the tissue type from which the cells were isolated. In some embodiments, the stem cells are allogeneic to the recipient (e.g., as is the case with embryonic stem cells). In some embodiments, the stem cells are autologous to the recipient. In other embodiments, syngeneic cells are used, while in still other embodiments, xenogeneic cells are used. In some embodiments, freshly isolated cells are cultured and deployed into or onto the substrate for implantation into a recipient individual. In other embodiments, cryopreserved cells are used. In some embodiments, induced pluripotent stem cells are used.

In several embodiments, stem cells are isolated (or thawed) and cultured under standard sterile in vitro culture conditions. In some embodiments, the cells are cultured in standard tissue culture media known and used for the growth of stem cells. In other embodiments, a xeno-free culture media is used. In some embodiments, culture media is supplemented with one or more growth factors in order to support the viability of the cells and/or induce differentiation into a particular cell type. In some embodiments, growth factors such as are included in serum used to supplement the growth media. In some embodiments, specific factors are added, such as, for example, fibroblast growth factor, transforming growth factor (e.g., TGFβ1), insulin-like growth factor, e.g., IGF-1). Cells may be grown, passaged, and continually cultured until such time that the cells have optimal characteristics for deployment into the substrates described herein. At that point, the cells (if suspension cells) may simply be collected, adjusted to a desired cell density, and deployed (e.g., injected) into the substrate. Cells that are grown on a surface may be enzymatically digested (e.g., trypsinized) or mechanically detached from the surface, adjusted to a desired cell density, and deployed (e.g., injected) into the substrate.

Due to the features and advantages of several embodiments of the substrates described herein, in several embodiments, cell numbers that are deployed into or onto the substrate are relatively low. In several embodiments, the number of cells delivered ranges from about $1.0 \times 10^3$ to $1.0 \times 10^8$. In several embodiments cell numbers deployed into or onto the substrate range from about $1.0 \times 10^4$ to about $1.0 \times 10^7$, from about $1.0 \times 10^5$ to about $1.0 \times 10^6$, and overlapping ranges thereof. In one embodiment, about $1.5 \times 10^5$ cells are used. In other embodiments, greater or lesser numbers of cells are used.

As discussed above, cells from a variety of tissues may be used. In several embodiments, ocular cells are used to treat ocular diseases including, but not limited to age related macular degeneration (wet or dry), diabetic macular edema, idiopathic choroidal neovascularization, or high myopia macular degeneration. In some ocular embodiments, RPE cells are used. In several embodiments, cardiac stem cells are used to treat cardiovascular disorders such as myocardial infarction, ischemic cardiac tissue damage, congestive heart failure, aneurysm, atherosclerosis-induced events, cerebrovascular accident (stroke), and coronary artery disease. In several embodiments, liver stem cells are used to treat liver disease such as hepatitis, cirrhosis, cancer, and the like. Diseases in other tissues, such as the kidney, lung, pancreas, intestine, and neural tissues, among others, may be treated with the methods and devices disclosed herein. In some embodiments, harvested bone marrow stem cells may be used to repopulate hematopoietic cells that are reduced due to leukemias, cancers, or therapies that reduce blood cell counts.

Delivery Methods

Substrates in accordance with embodiments described herein may be delivered by various methods depending on the target tissue. Substrates may be delivered during an open surgical process. For example, during ocular surgery a substrate may be delivered to a region of the eye. In several embodiments, substrates are implanted in a specific delivery procedure. In some ocular embodiments, the substrates are delivered to the sub-retinal space. In some embodiments, an ab-interno procedure is used. In other embodiments, an ab-externo procedure is used. In some embodiments, a pars plana surgical approach is used for implantation. In other embodiments a trans-scleral approach is used for implantation. In several embodiments, substrates are attached (e.g., sutured, adhered) to a surface. In several embodiments, substrates are delivered endoscopically, via catheter-based methods, intravascularly, intramuscularly, stereotactically (e.g., for delivery of the substrate/cells to the brain or other neural tissue) or by other means known in the art for a particular target tissue. Depending on the substrates design and the target tissue, customized surgical tools are used to make the delivery of the substrates less traumatic, faster, or otherwise less risky or more beneficial to the subject.

Figure 23C:
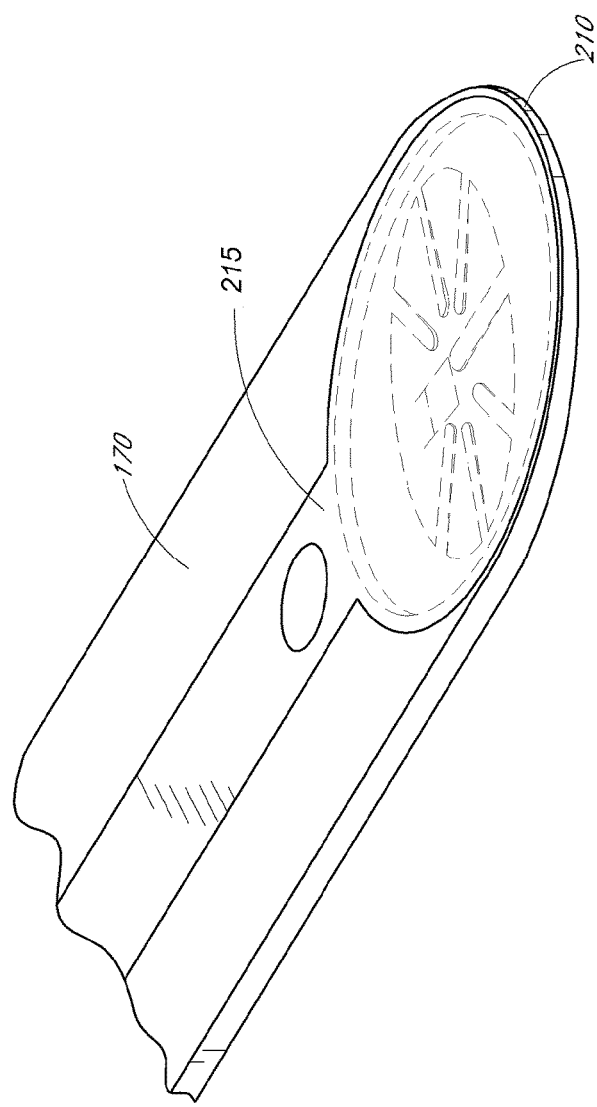

A non-limiting example of such a tool is shown in FIGS. 23A-23C. The tool 160 shown in FIG. 23A comprises a handle 170, which is held by a surgeon during the manipulation and surgical implantation of a substrate into a subject. The tool further comprises a recessed portion 180 optionally having a plurality of support structures 190. Once a particular substrate is identified and selected for implantation it is cut, in several embodiments, from a substrate frame such as those described above. Rather than allow the substrate to float freely in the media within the culture vessel (which could allow the cell-growth surface to contact the culture dish, other cell-growth surfaces etc., leading to damage to the cells) the surgical tool 160 is contacted with the basal (or other non-cellular) surface of the freed substrate.

In several embodiments the recessed portion 180 of the tool is placed under the substrate during or after the cutting process. This recessed portion functions to protect the cells on the substrate against possible shear stress introduced during insertion. As described above, in several embodiments the substrate comprises a lip around the border of the substrate. The substrate lip and recessed portion of the tool have complementary functions in retaining as many cells as possible on (or in) the substrate during (and after) the implantation process. In several embodiments, the insertion side (e.g., corresponding to the apical cell-containing side of the substrate) of the recessed portion is uncovered. In such embodiments, protection of the growing cell monolayer from shear stress is accomplished by the effective protrusion of the upper-most surface of the tool over the apical surface of the substrate. The depth of the recessed portion is defined by the materials chosen for the tool (e.g., depth is small enough to allow effective machining of a given material). The recessed portion is also configured to allow for safe implantation of the substrate. The dimensions are small enough to reduce disturbance to the target tissue (e.g., the subretinal space) yet be large enough to fully shield the height of the substrate. The dimensions are small enough to reduce disturbance to the target tissue (e.g., the subretinal space) yet be large enough to fully shield the height of the substrate which may include the substrate, additional peptides and extracellular matrix proteins allowing for cell viability and adhesion (e.g. a thin layer (~10-100 nm) of a functionalized surface such as parylene A or AM, parylene plasma treated with ammonia to give amine groups, linear or cyclic RGD, SYNTHEMAX (Corning), laminin 511, etc.). In several embodiments, the depth of the recessed portion (as measured from the top surface of the tool handle 170 ranges from about 15 µm to about 500 µm. In several embodiments, the depth ranges from about 20 µm to about 100 µm, from about 50 µm to about 150 µm, from about 100 µm to about 200 µm, from about 150 µm to about 200 µm, from about 200 µm to about 300 µm, from about 250 µm to about 350 µm, from about 300 µm to about 400 µm, from about 350 µm to about 450 µm, from about 400 µm to about 500 µm, and overlapping ranges thereof.

In addition to, or in place of, the recessed portion of the tool, additional protection for the cells seeded on the substrate can be provided by layering a dissolvable hydrogel over the apical surface of the substrate. The hydrogel thereby reduces cell loss or disturbance during manipulation and implantation, and in some embodiments, at least partially inhibits possible cellular migration after insertion. Alternatively, a retractable cover 215 can be used to provide protection during implantation (see e.g., FIG. 23C). In several embodiments, the retractable over slides in a distal to proximal direction upon actuation of a switch by a surgeon (or other personnel). In several embodiments, MEMS technology is employed to retract the cover. Thus, in certain embodiments, the substrate is retained within the recessed portion, and covered, until such time as the surgeon (or other personnel) determines that the tool is in an appropriate position for release of the substrate. In several embodiments, the entire delivery tool, with the substrate positioned and retained within the recessed portion, is housed, partially or completely within a delivery capsule. In several embodiments, the capsule has an open distal end and a proximal end fixed (at least temporarily) to the tool. Further, the capsule optionally has at least one perforation in the distal end of the capsule, such that retraction of the capsule, or advancement of the tool, allows the recessed portion of the device to move clear of the capsule for the final delivery of the substrate. In several embodiments, the distal end of the device is configured to cut, break, or otherwise penetrate the capsule without damaging the cells in or on the substrate. Alternatively, the device may further comprise a balloon positioned that is positioned within the capsule so as to break the capsule along said at least one perforation when inflated, allowing the recessed portion of the device to move clear of the capsule for the final delivery of the substrate.

An additional view of one embodiment of an insertion instrument is shown in FIG. 23D. In several embodiments, such an embodiment (or similar embodiments) is preferred because the smoother, contoured edges of the instrument reduce the potential for damage to target tissue (or surrounding tissue) during insertion of a cell-seeded substrate.

In some embodiments, the distal-most surface of the recessed portion (e.g., the wall of the recessed portion) is perpendicular to the floor of the recessed portion. In some embodiments, the wall is angled in (acutely with respect to floor of the recessed portion) so as to create a wedge as target site tissue (e.g., native RPE-photoreceptor boundary) is incised. In some embodiments, the angle ranges from about 5 degrees to about 40 degrees, from about 10 to about 30 degrees, from about 15 to about 25 degrees, from about 15 to about 20 degrees, from about 12 to about 17 degrees, including 13, 14, 15, 16 degrees, and overlapping ranges thereof.

In several embodiments, the outer diameter of the recessed portion is sufficient to hold an substrate as described herein, yet small enough to reduce trauma to the target tissue (e.g., the eye). In some embodiments, the outer diameter of the recessed portion is between about 1 and about 10 mm, between about 2 mm and about 8 mm, between about 4 mm and 6 mm, between about 1 mm and 6 mm, and overlapping ranges thereof. In some embodiments, the outer diameter ranges from about 2 mm to about 5 mm, including 2.25, 2.5, 2.75, 3.0, 3.25, 3.5, 3.75, 4.0, 4.25, 4.5, and 4.75 mm. In several embodiments, the inner diameter of the recessed portion (which stably supports the substrate) ranges from about 0.5 to about 7 mm, from about 1 mm to about 6 mm, from about 2 mm to about 5 mm, from about 3 mm to about 4 mm, and overlapping ranges thereof. In some embodiments, the inner diameter ranges from about 1.5 to about 5 mm, including about 1.5, 2.0, 2.5, 3.0, 3.5, 4.0, and 4.5 mm.

Materials used to fabricate any of the insertion tools disclosed herein include, but are not limited to, metal, polymers (e.g., thermoplastic polymers such as polypropylene). In several embodiments the tool is fabricated from the same material as the substrate. For example, in one embodiment parylene is used. In several embodiments, at least one surface of the tool is coated or otherwise comprises a non-stick surface. In some embodiments, synthetic fluoropolymers of tetrafluoroethylene, such as polytetrafluoroethylene (PTFE), are used to minimize adherence of tissue to the device during implantation. In some embodiments, such non-stick surfaces are used to coat the surface of the support structures in order to facilitate release of the substrate at a target site.

In several embodiments, negative gas (e.g., nitrogen gas) or fluid (e.g., phosphate buffered saline or lipid-based solution) pressure is directed to the basal surface of the substrate via a port 200 in the recessed portion of the tool. In some embodiments, a bioadhesive and/or an adhesive protein is used to retain the substrate. In either case, the retention of the substrate is reversible. For example, the removal of negative pressure, or in several embodiments, introduction of positive air or fluid pressure through the port 200 will release the substrate from the recessed portion of the tool and into position in a surgical target site. In several embodiments, air or fluid pressure is introduced via a connection between the tool and a standard ophthalmological surgical tool that provides both positive and negative air pressure control. In several embodiments, localized negative (or positive) pressure is achieved by fabricating one or more additional ports along the supporting structures, such that local application (e.g., above or adjacent to the ports) is achievable. In some embodiments, disruption of the integrity of partially planar substrates is reduced by application of localized negative pressure primarily to the thicker supports structures of the substrate. In several embodiments, a mechanical means is used to displace the implant. In some embodiments, MEMS latches are positioned on the support structures and function to grasp the basal surface of the implant during the implantation process, then allow release of the implant. In further embodiments, a reversible bioadhesive (controlled by electrical, chemical, enzymatic or other means) is used to retain the substrate in position within the recessed portion.

The direction of force imparted on the substrate when positioned and retained within the recessed portion is defined by the dimensions of the port, gas or fluid pressure, and the dimensions of the supporting features 190. Preferably, the dimensions of the supporting features should not be so large so as to cause indentation in the cell-seeded substrate, as such indentations could disrupt or damage the cells. The dimensions of the supporting features vary depending on the materials comprising the tool. For example, certain materials may fracture or melt if machined below a certain minimum dimension. In other cases, technical limitations of micro- or laser-machining limit the dimensions of the support features. In several embodiments, the minimum height or width of the support features is about 15 µm. In several embodiments, the height or width of the support features ranges from about 15 µm to about 400 µm, from about 25 µm to about 450 µm, from about 50 µm to about 400 µm, from about 75 µm to about 350 µm, from about 100 µm to about 300 µm, from about 125 µm to about 250 µm, from about 150 µm to about 200 µm, and overlapping ranges thereof.

In several embodiments, the tool is curved during manufacturing so as to (1) minimize the incision into the target tissue, which reduces possible risk of infection, (2) match the substrate curvature with the radius of curvature (ROC) of the targeted location of the target tissue, so as not to protrude and apply undue pressure to sensitive or easily damaged cell types of the target tissue. For example, when targeting the eye, curvature of the tool reduces the sclerotomy size and reduces pressure applied to and associated damage to the choroid or sclera. In such embodiments, the ROC of the target site of the eye can range from about 3 to about 20 mm, from about 5 to about 15 mm, from about 10 to about 13 mm, and overlapping ranges thereof. In several embodiments the ROC of the tool is matched to that of the eye of a subject, ranging from about 12 to about 15 mm, including about 12.25, 12.5, 12.75, 13.0, 13.25, 13.5, 13.75, 14.0, 14.25, 14.5, and 14.75 mm. The tool is optionally curved along one or two axes, with two axis curvature rendering at least a portion of the tool to resemble a portion of a sphere.

In several embodiments, the distal portion of the tool is angled. In some embodiments, the angle is advantageous for the capture of the substrate from a culture dish and/or for facilitating surgical implantation. In some embodiments, a fixed angle tool is used. In some embodiments, the angle is variable, such as through the actuation of a wire-based mechanism, electrical conduction, and the like.

In several embodiments, curvature of the tool (or a cell-seeded substrate) is tuned before or during surgical implantation by deposition of a metal lead composed of a shape memory alloy (e.g. Ni—Ti) along portions of the perimeter of the tool or substrate. Subsequent passage of current can tune the substrate shape in situ via ohmic heating. Numerous shapes that effectively allow customization of the shape of the tool or a substrate are achievable via differential distribution of the alloy.

Figure 23F:
FIGS. 23E-23F depict uses of various embodiments of the manipulation/implantation instruments disclosed herein to implant a substrate seeded with cells into isolated porcine eyes.
Figure 23E:

In several embodiments the surgical tool 160 is mated with a conventional vitrectomy cutter. In some embodiments, the distal-most end 210 of the tool is fabricated, machined, honed, sharpened, or otherwise formed to a thickness that enables the tool to simultaneously hold a seeded substrate and also to incise tissue. Thus, in some embodiments, surgical tools and implantation tools are self-contained within the tool 160, which is advantageous when the target site is a small space or difficult to access. In still additional embodiments, the tool may be mated with other standard surgical instruments (e.g., forceps, suction, electrocautery, etc.). Implantation of a substrate seeded with cells via a tool as described above is demonstrated in an isolated porcine eye in FIGS. 23E.

Figure 23G:
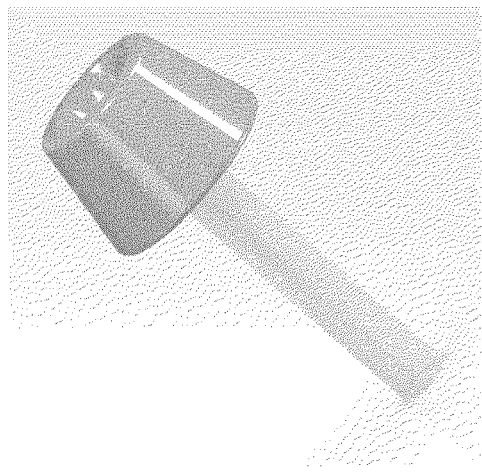
FIGS. 23G-23H depict a tapered cannula (23G) with cross sectional view (23H) showing gradual taper to tubing diameter.
Figure 23H:
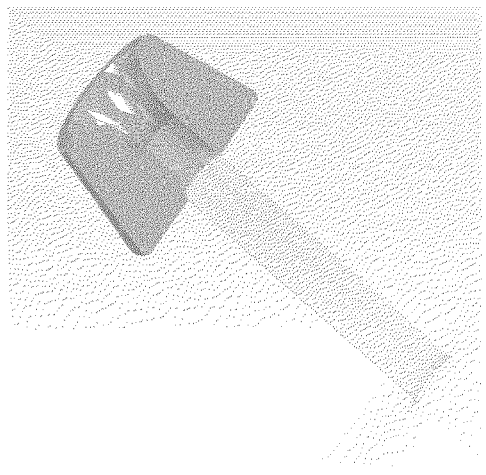

Additional insertion methods are accomplished, in some embodiments, by insertion of the substrate directly through the sclera by way of a cannula. In some embodiments, the cannula comprises of a tube passing through the scleral tissue and a polymer cap attached to the upper end of the tube to provide a gradual reduction in diameter to the tubes inner diameter. (See e.g., FIGS. 23G-23H). The gradual reduction in the cap provides a mechanism for rolling the substrate into a cylindrical structure so that it may be delivered through the tube. In some embodiments, the tube comprises a polymer with low coefficient of friction and high stiffness, such as polyimide. In some embodiments, the tube has a nominal inner diameter of about 0.041" (ranging from about 0.030" to 0.050"). In some embodiments, the cap has a major diameter of about 0.10" (ranging between about 0.070" to 0.20") and tapering to the inner diameter of the tube. In some embodiments, the cap comprises a biocompatible polymer that can be easily bonded to the tubing such as nylon or ABS. In several embodiments, the cannula is inserted into the sclera by means of a rigid steel tube with a sharpened tip. In some embodiments, the cannula is mounted concentrically on to the tube such that the tip pierces the sclera and creates an incision. After the tube and cannula have been inserted the tube is removed with the cannula tube remaining inserted in the sclera.

Figure 23I:
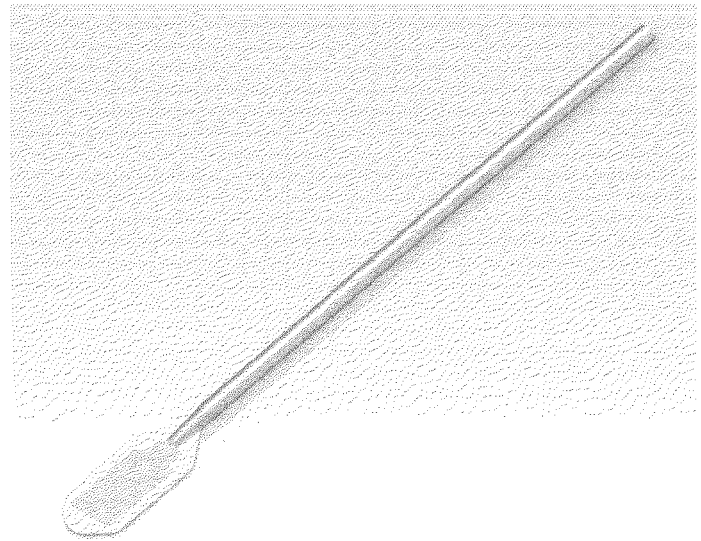
FIGS. 23I-23J depict devices for facilitating manipulation of substrates.

To provide additional support and protection to the substrate, in several embodiments, an additional platform (e.g., a baseplate) is used to curve around and/or encapsulate the substrate sheet. In some embodiments, the platform comprises a thin polymer sheet with a high stiffness coefficient. A handpiece for surgeon manipulation with a cylindrical tube extending from the handpiece is used in some embodiments to provide a means for manipulation of the platform. (See e.g., FIG. 23I). As the platform is passed through the tapered cannula the sheet will deform into a cylindrical shape forcing the substrate into cylindrical form as well. The high stiffness will provide support to prevent buckling during insertion. In some embodiments, the tube has a nominal diameter of about 0.0185" (ranging between about 0.015" and about 0.030"). In one embodiment, the tube is constructed from stainless steel. In several embodiments, the thin sheet has a thickness of about 0.003" (ranging between about 0.0015" and about 0.005"), a nominal width of about 0.14" (ranging between about 0.10" and about 0.20"), and a nominal depth of about 0.25" (ranging between about 0.20" and about 0.30"). In several embodiments, the sheet comprises a low friction polymer with high stiffness such as PTFE, UHMPE, or polyimide.

Figure 23J:
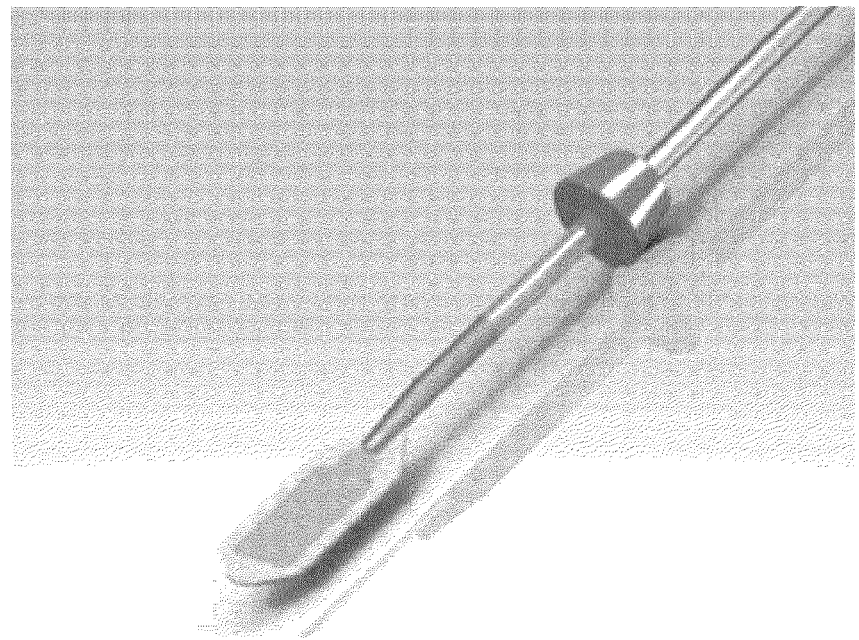
Figure 23K:
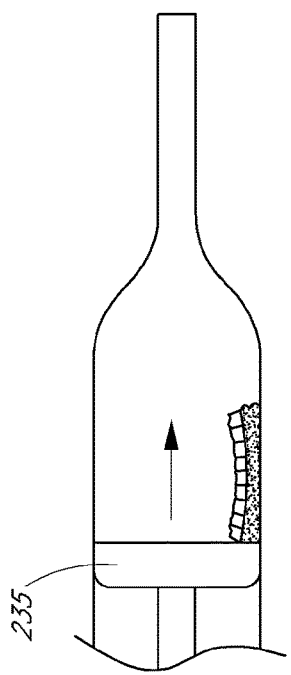
FIGS. 23K-23S depict various embodiments of a conical funnel delivery device and associated structures in accordance with several embodiments disclosed herein.

An additional embodiment of the platform comprises a secondary tube embedded within the longitudinal axis of the platform for additional stiffness and to provide a means for suction to hold the substrate in place. (See e.g., FIG. 23J). In some embodiments, the tube is rectangular in cross section with lateral width being optionally greater than height and with nominal dimensions of about 0.008" by about 0.010". In several embodiments, the tube runs concentrically within the larger outer tube from the handpiece and have a fluidic (or gaseous) connection to a vacuum source. Implantation of a substrate seeded with cells via a tool as described above is demonstrated in an isolated porcine eye in FIG. 23F.

An additional non-limiting example of a tool to manipulate and substrate the substrates as described herein (as well as a method of insertion) is shown generally in FIGS. 23K-23N. In several embodiments, the tool 220 is shaped as a conical funnel, open at both ends, and configured to have an internal passageway 225. In some embodiments, the tool is transparent, thus allowing visualization of a substrate 10' within the tool. In several embodiments, the tool further comprises a plunger 235 to push the substrate or cellular sheet into the passageway, and then out of the tool and into position at a target tissue site. In several embodiments, the target site is the sub-retinal space. Several embodiments of this tool are particularly advantageous in that the tool capitalizes on the ability of the substrate and cells to be curved without damaging integrity of the cells or the substrate. The tool comprises an exit port 230 from which the substrate is pushed out of the passageway of the tool. In some embodiments, the substrate is pushed out of the tool via positive fluid or gas pressure. In several such embodiments, the tool has a pressure modulator 240 that allows for control of the amount of pressure. In some embodiments, a plunger 235 is used to insert and/or push the substrate out of the exit port. In several embodiments, the exit port ranges from about 1 mm to about 40 mm in diameter (inner diameter). In some embodiments, the inner diameter of the exit port ranges from about 1 mm to about 20 mm, about 20 mm to about 40 mm, about 1 mm to about 10 mm, or about 1 mm to about 5 mm. In some embodiments, the inner diameter of the exit port ranges from about 1 mm to about 2 mm, about 2 mm to about 3 mm, about 3 mm to about 4 mm, about 4 mm to about 5 mm, and overlapping ranges thereof. In several embodiments, the inner diameter of the exit port is about 1.1, 1.2, 1.3, 1.4, or 1.5 mm. In several embodiments, the inner diameter of the exit port is configured to be used with a substrate such that the rolled substrate fits within the circumference of the exit port without overlapping edges of the substrate.

In several embodiments, the outer diameter of the distal end (the end inserted into an ocular target site) of the funnel shaped tool is between about 1.0 mm and 2.5 mm. In some embodiments, the outer diameter ranges from about 1.0 mm to about 1.5 mm, from about 1.5 mm to about 2.0 mm, from about 2.0 mm to about 2.5 mm, and overlapping ranges thereof. In several embodiments, surgical tools of about 20 gauge are used, such as a 20 gauge MVR blade having a blade width of about 1.2 mm. Thus, in several embodiments, the tool is configured to fit within an incision made by such a blade.

Figure 23L:
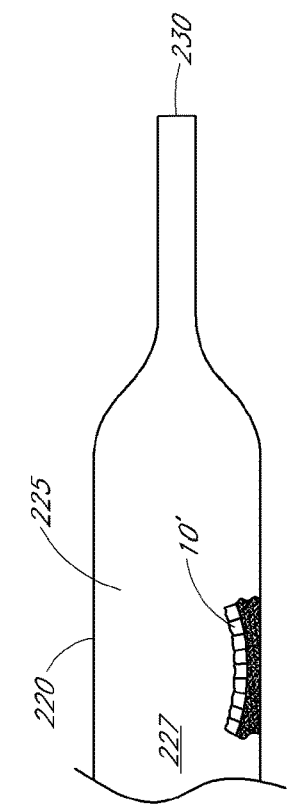

A wider opening 227 on the proximal end of the tool allows loading of the substrate. In several embodiments, the substrate is curled into a cylinder shape gradually when the plunger pushes the edge of the graft towards the narrow part of the funnel. In several such embodiments, the RPE on the surface of the substrate are wrapped inside without touching the passageway of the tool (see e.g., FIGS. 23L and 23O-23R). The exit port of the funnel allows small amount of culture medium to optionally be placed within the passageway to reduce dehydration of the cells during the implantation process. The substrate is, in some embodiments, delivered with plunger pushing from behind (FIG. 23L). In some embodiments, the plunger further comprises a protruding thin membrane 255 (made of, for example, parylene) which supports the base of the substrate (see FIG. 23S). The orientation of the substrate can be controlled by twisting the tool, the plunger, or both, to ensure that the cell surface is facing the desired direction for implantation.

Figure 23M:
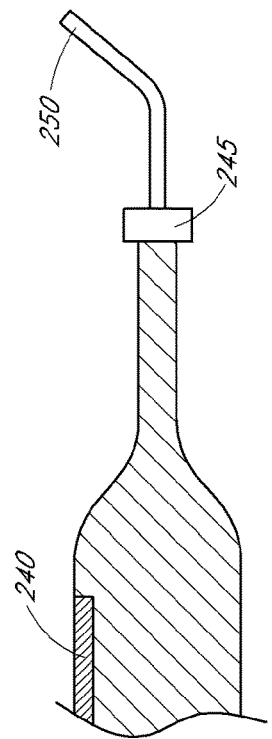
Figure 23N:
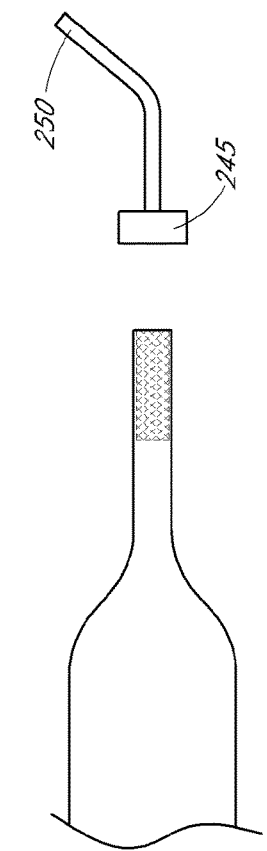
Figure 23P:
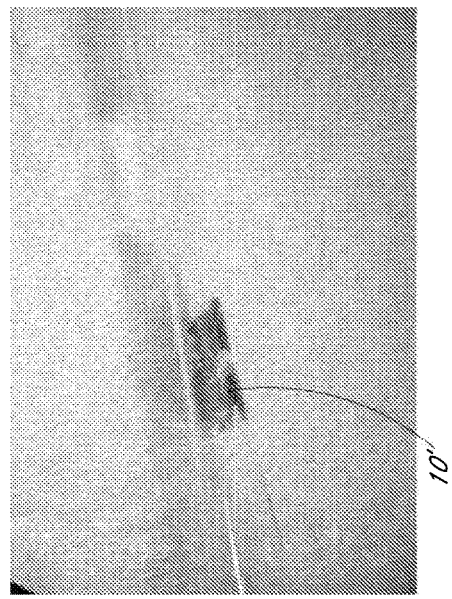
Figure 23O:
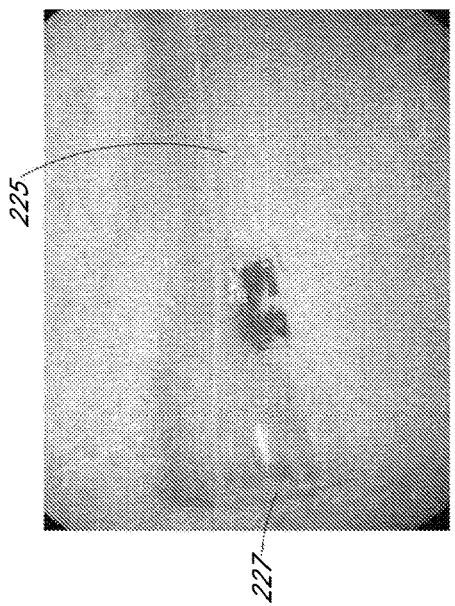
Figure 23R:
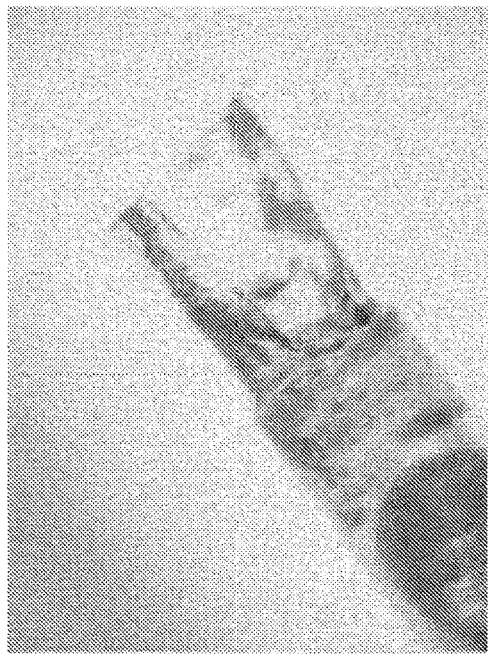
Figure 23Q:
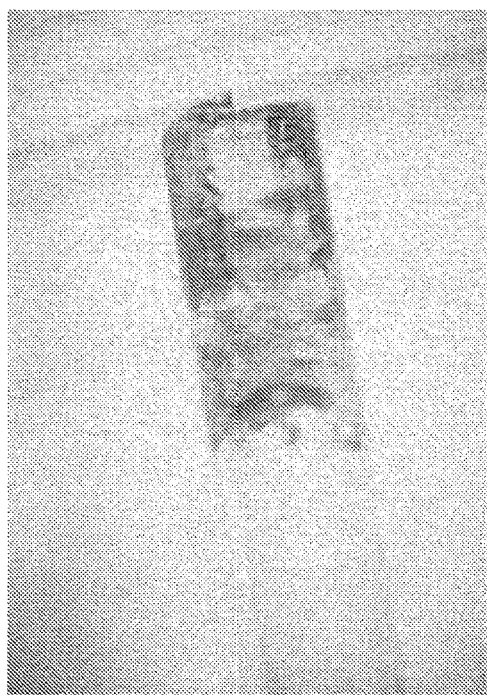
Figure 23S:
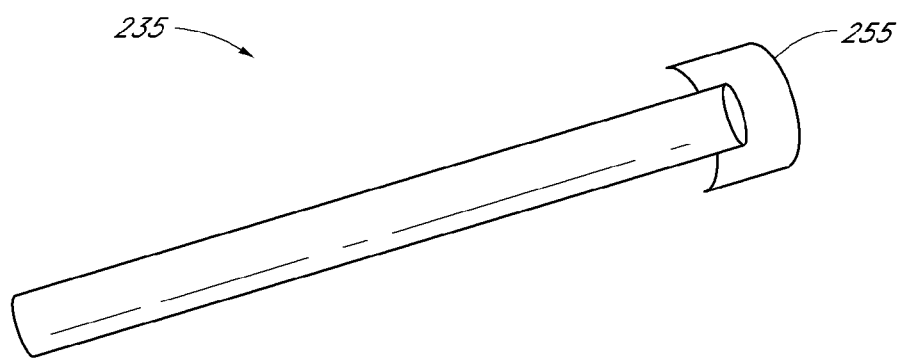
Figure 23T:
FIG. 23T depicts an angled delivery device employed in certain embodiments disclosed herein.

In several embodiments, the surgical approach for ocular implantation is a pars plana approach. In some species, the pars plana lies approximately 3.5-4 mm away from cornea. In several embodiments, the tool delivers the substrate parallel to the posterior eye wall. Thus, in some embodiments, tool is designed with an angled distal tip. As shown in FIGS. 23M and 23N, in one embodiment, a straight tool is configured to be connected via an interconnect 245 to another delivery tube 250 (pre-curved to match the shape and dimensions of the target site). See also FIG. 23T. In such embodiments, a flexible plunger capable of passing through the curvature of the delivery tool is used.

In some embodiments, the tool further comprises an opening on the side of the tool, the opening dimensioned to mate with a custom or commercially available surgical tool handle. In several embodiments the opening ranges from about 0.25 cm to about 5 cm in diameter. In some embodiments, the opening ranges from about 0.5 cm to about 1 cm, from about 1 cm to about 1.5 cm, about 1.5 cm to about 2.0 cm, about 2.0 cm to about 5 cm, and overlapping ranges thereof.

As discussed above, several embodiments employ substrates comprising an inhomogeneous basal surface comprising supporting features juxtaposed with said substantially homogeneous apical surface. As shown in FIG. 24, dimension D20 of the substrate ranges, depending on the embodiment, between about 0.2 and about 7 mm, including from about 0.2 to about 0.4 mm, about 0.4 to about 0.6 mm, about 0.6 mm to about 0.8 mm, about 0.8 mm to about 1.0 mm, about 1.0 to about 2.0 mm, about 2.0 to about 3.0 mm, about 3.0 to about 4.0 mm, about 4.0 to about 5.0 mm, about 5.0 to about 6.0 mm, and overlapping ranges thereof. Dimension D21 ranges from about between about 0.2 and about 7 mm, including from about 0.2 to about 0.4 mm, about 0.4 to about 0.6 mm, about 0.6 mm to about 0.8 mm, about 0.8 mm to about 1.0 mm, about 1.0 to about 2.0 mm, about 2.0 to about 3.0 mm, about 3.0 to about 4.0 mm, about 4.0 to about 5.0 mm, about 5.0 to about 6.0 mm, and overlapping ranges thereof. Dimension D22 ranges from between about 0.5 mm to about 9 mm, including about 0.5 to about 1.0 mm, about 1.0 to about 2.0 mm, about 2.0 to about 3.0 mm, about 3.0 to about 4.0 mm, about 4.0 to about 5.0 mm, about 5.0 to about 6.0 mm, about 6.0 to about 7.0 mm, about 7.0 to about 8.0 mm, about 8.0 to about 9.0 mm and overlapping ranges thereof. In some embodiments, length D22 ranges from about 4 to about 7 mm, including 4.2, 4.4, 4.6, 4.8, 5.0, 5.2, 5.4, 5.6, 5.8, 6.0, 6.2, 6.4, 6.5, 6.5, 6.7, 6.8, and 7.0 mm. Dimension D23 ranges, in several embodiments, from between about 0.1 mm to about 6 mm, including about 0.2 to about 1.0 mm, about 1.0 to about 2.0 mm, about 2.0 to about 3.0 mm, about 3.0 to about 4.0 mm, about 4.0 to about 5.0 mm, about 5.0 to about 6.0 mm, and overlapping ranges thereof. In some embodiments, D23 is between about 1.3 and 1.6 mm, including 1.4 and 1.5 mm. In several embodiments the substrate comprises rounded 'corners'. In several embodiments, this is advantageous because tearing, kinking, or other distortions that may occur with a sharp square cornered substrate are avoided. In some embodiments, the corners of the substrate all have equivalent radii. However, in several embodiments, the radii are distinct (e.g., certain 'corners' are sharper than others). As shown in FIG. 24, R1, in some embodiments, ranges from about 0.1 to about 0.8 mm, including about 0.2 mm, 0.3 mm, 0.4 mm, 0.5 mm, 0.6 mm, 0.7 mm, and radii lying in between these values. R2, in several embodiments ranges from about 0.05 to about 0.5 mm, including about 0.07 mm, about 0.09 mm, about 0.1 mm, about 0.2 mm, about 0.3 mm, about 0.4 mm and radii lying in between these values.

Figure 25:
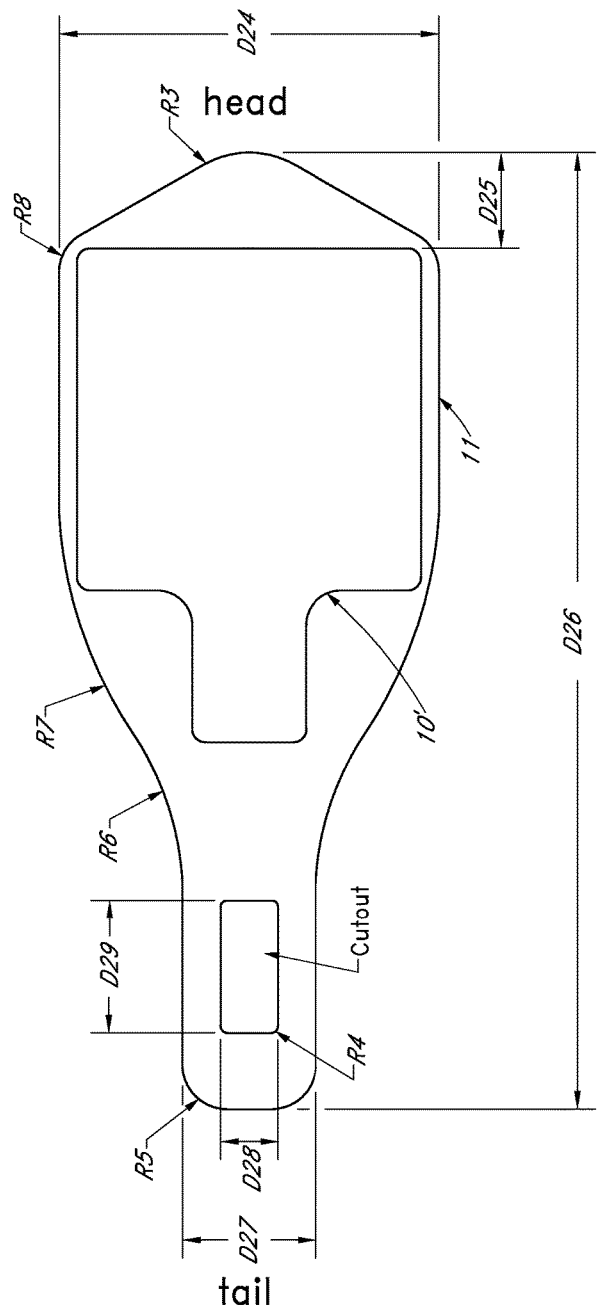
FIG. 25 illustrates an example of a substrate resting on a supporting surface for delivery to a target tissue by a delivery device as disclosed herein.

Also as discussed herein, in several embodiments the substrate is supported on an accessory surface during delivery to the target tissue. A non-limiting example of this supporting surface is shown in FIG. 25. Generally, the supporting surface functions to hold the substrate during the implantation process (it may be considered a "launch pad" for the substrate). In several embodiments, the supporting surface is flexible, allowing the substrate (as well as the support) to be rolled in a manner allowing for the substrate and support surface to be rolled (as described above) without the cells seeded on the substrate surface contacting one another. Generally, the support surface is larger than the substrate, in order to fully support the substrate, and in addition to provide protection for the cells seeded on the substrate. As shown generally in FIG. 25, the width of the support surface, D24 ranges from about, between about 0.2 and about 7 mm, including from about 0.2 to about 0.4 mm, about 0.4 to about 0.6 mm, about 0.6 mm to about 0.8 mm, about 0.8 mm to about 1.0 mm, about 1.0 to about 2.0 mm, about 2.0 to about 3.0 mm, about 3.0 to about 4.0 mm, about 4.0 to about 5.0 mm, about 5.0 to about 6.0 mm, about 6.0 to about 7.0 mm and overlapping ranges thereof. The support surface, in some embodiments is longer than the substrate. This additional length, D25, ranges from about 0.5 to about 2 mm, in several embodiments. In some embodiments, the extra length ranges from about 0.6 to about 0.8 mm, from about 0.8 to about 1.0 mm, from about 1.0 to about 1.2 mm, from about 1.2 to about 1.6 mm, from about 1.6 to about 1.8 mm, from about 1.8 to about 2.0 mm, and overlapping ranges thereof. The overall length of the support surface (D26) ranges from about 7 to about 15 mm, about 7 to about 8 mm, about 8 to about 9 mm, about 9 to about 10 mm, about 10 to about 11 mm, about 11 to about 12 mm, about 12 to about 13 mm, about 13 to about 14 mm, about 14 to about 15 mm, and overlapping ranges thereof. The tail of the support surface (D27) ranges, in several embodiments, from about 1.3 to about 2.0 mm, including about 1.4 mm, about 1.5 mm, about 1.6 mm, about 1.7 mm, about 1.8 mm, about 1.9 mm, and lengths between the ranges recited above.

In several embodiments, the support surface comprises a cutout area. In several embodiments, this area functions to allow the support surface to be connected to an implantation device. In several embodiments the width of the cutout (D28) ranges from about 0.3 mm to about 1.0 mm, including about 0.3 mm to about 0.4 mm, about 0.4 mm to about 0.5 mm, about 0.5 mm to about 0.6 mm, about 0.6 mm to about 0.7 mm, about 0.7 mm to about 0.8 mm, about 0.8 mm to about 0.9 mm, about 0.9 mm to about 1.0 mm, and overlapping ranges thereof. In several embodiments the length of the cutout ranges from about 1.3 to about 2.0 mm, including about 1.4 mm, about 1.5 mm, about 1.6 mm, about 1.7 mm, about 1.8 mm, about 1.9 mm, and lengths between the ranges recited above. In several embodiments the cutout has rounded corners. In several embodiments, the radius of the corners is between about 0.5 to about 1.5 mm, including about 0.5 to about 0.7 mm, about 0.7 to about 0.9 mm, about 0.9 to about 1.1 mm, about 1.1 to about 1.3 mm, about 1.3 to about 1.5 mm, and overlapping ranges thereof.

In several embodiments, substrates and/or the support surfaces optionally underlying the substrates are handled by means of a retractable retinal forceps. In several embodiments, the forceps comprise two tines manufactured from nitinol (or other acceptable shape memory material that allows for high strains to be accomplished during the tine extension and retraction) which are encapsulated within a rigid tube. In some embodiments, as the tines are retracted they interact with the tube and the curved lengths are forced into a linear configuration within the tube. (FIG. 28A) Upon being extended, the superelastic ability of the nitinol (or other suitable shape memory material) allows for restoration of the original curvature. (FIG. 28B) In several embodiments, the tines have a rectangular cross section (or optionally elliptical, circular, half-round or other shape) with a nominal width of about 0.04" (ranging between 0.01" and 0.10") and total linear length (including that within the handpiece) of approximately 2 inches (ranging between 1.5" and 3"). In some embodiments, the total length of the tines ranges from about 1.5" to about 1.7", from about 1.7" to about 1.9", from about 1.9" to about 2.1", from about 2.1" to about 2.3", from about 2.3" to about 2.5", from about 2.5" to about 2.7", from about 2.7" to about 2.9", and overlapping ranges therein. Depending on the subject, other lengths greater or smaller than those disclosed above may be used.

Certain embodiments of the delivery instruments employ forcep tines of a particular length that advantageously allow placement of the substrates under the retina, without the body of the instrument itself going under the retina. As a result, there is a greatly reduced potential for injury to RPE cells as well as to the surrounding choroid. Further, manipulation of the instrument is enhanced, because the actual surface area of the instrument that is in contact with the target tissue is reduced. As a result the likelihood of a precise and successful substrate implantation is increased. In some such embodiments, the length of the forcep tines extending beyond the body of the instrument ranges from about 2.0 mm to about 10.0 mm. In some embodiments the length of the force tines extending beyond the body of the instrument ranges from about 2.0 mm to about 2.5 mm, from about 2.5 mm to about 3.0 mm, from about 3.0 mm to about 3.5 mm, from about 3.5 mm to about 4.0 mm, from about 4.0 mm to about 4.5 mm, from about 4.5 mm to about 5.0 mm, from about 5.0 mm to about 5.5 mm, from about 5.5 mm to about 6.0 mm, from about 6.0 mm to about 6.5 mm, from about 6.5 mm to about 7.0 mm, from about 7.0 mm to about 7.5 mm, from about 7.5 mm to about 8.0 mm, from about 8.5 mm to about 9 mm, from about 9.0 mm to about 10.0 mm (and overlapping ranges thereof).

In some embodiments, the distal end of both tines is curved to accommodate manipulation of materials. The inner tine having a curvature larger than the outer tine with initial nominal radius of about 0.04" (ranging up to about 0.10"), and transitioning to a larger radius of nominal radius of about 0.08" (ranging between 0.05" and about 0.20"). In one embodiment, the outer tine has a smaller radius of curvature with initial nominal radius of about 0.02" (ranging between about 0.01" and about 0.05"), transitioning to a larger radius of nominal radius of about 0.07" (ranging between about 0.03" to 0.2"). In other embodiments, one tine may be straight with the other optionally being curved. In still additional embodiments, both tines may be straight. In some embodiments, the tines are encapsulated within a stainless steel tube in order to provide rigid support to the tines. In some embodiments, the tube has a nominal inner diameter of about 0.027" (ranging from about 0.015" to about 0.05") and length of about 1.20" (ranging between about 1.0" and about 1.75").

In one embodiment, the tube is mounted to a plastic hand piece (optionally disposable) containing a mechanism for extending and retracting the tines. In some embodiments, the hand piece is reusable, and constructed of a more durable (and optionally sterilizable material, e.g., stainless steel). In one embodiment, the extension/retraction mechanism comprises two gears of unequal diameter connected to a wheel operated by the surgeon that, when actuated, extends or retracts the tines at different rates. In several embodiments, the rate is proportional to the curvature of the tines to allow the tips to remain coincident during extension and retraction to prevent tearing of the substrate or material being held. In several embodiments, the tines are directly attached to linear racks and the racks are meshed and driven by the gears connected to the wheel. Alternatively, the wheel mechanism could be replaces by a linear or other rotational actuator, or a slide mechanism. In several embodiments, the preference of surgeon dictates the mechanism used.

Additionally, in several embodiments, the shape of the support surface facilitates curvature of the support surface while supporting a cell-seeded substrate. As shown in FIG. 25, several embodiments of the support surface have rounded edges. R6, for example, ranges from about 3 mm to about 6 mm, including about 3.5 mm to about 4.0 mm, about 4.0 mm to about 4.5 mm, about 4.5 mm to about 5.0 mm, about 5.0 mm to about 5.5 mm, about 5.5 mm to about 6 mm, and overlapping ranges thereof. R7, in several embodiments, ranges from about 4 mm to about 7 mm, including from about 4.0 mm to about 4.5 mm, from about 4.5 mm to about 5.0 mm, from about 5.0 mm to about 5.5 mm, from about 5.5 mm to about 6.0 mm, from about 6.0 mm to about 6.5 mm, from about 6.5 mm to about 7.0 mm, and overlapping ranges thereof. R8, in several embodiments, ranges from about 0.4 to about 1.0 mm, depending on the embodiment. In several embodiments R8 is between about 0.4 and 0.5 mm, between about 0.5 and 0.6 mm, between about 0.6 and 0.7 mm, between about 0.7 and 0.8 mm, between about 0.8 and 0.9 mm, between about 0.9 and 1.0 mm, and overlapping ranges thereof.

Figure 26:
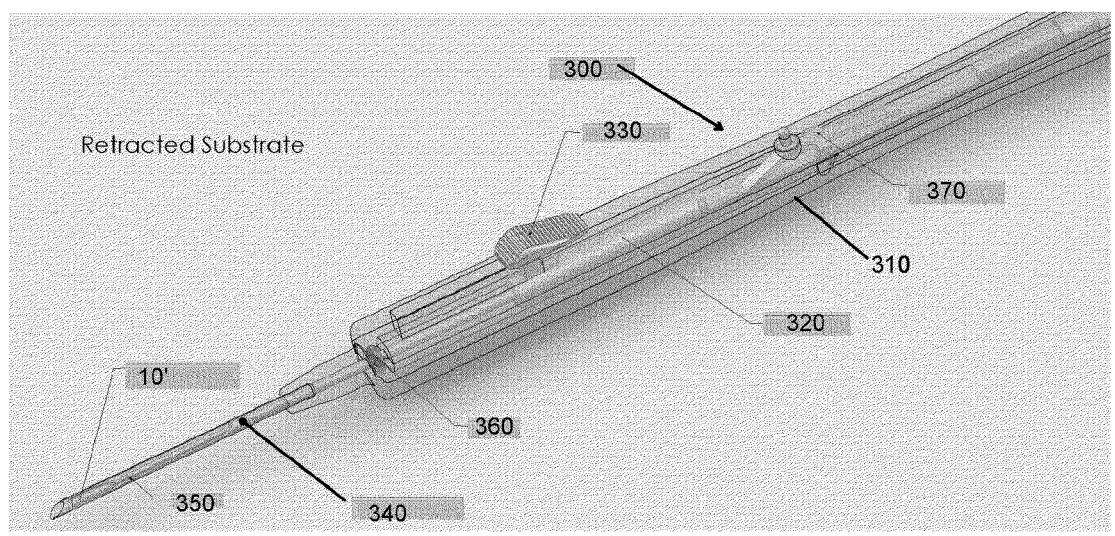
FIG. 26 illustrates an example of a delivery device according to several embodiments disclosed herein. The Figure illustrates the device in a retracted position with a cell-seeded substrate contained within the distal portion of the device.
Figure 27:
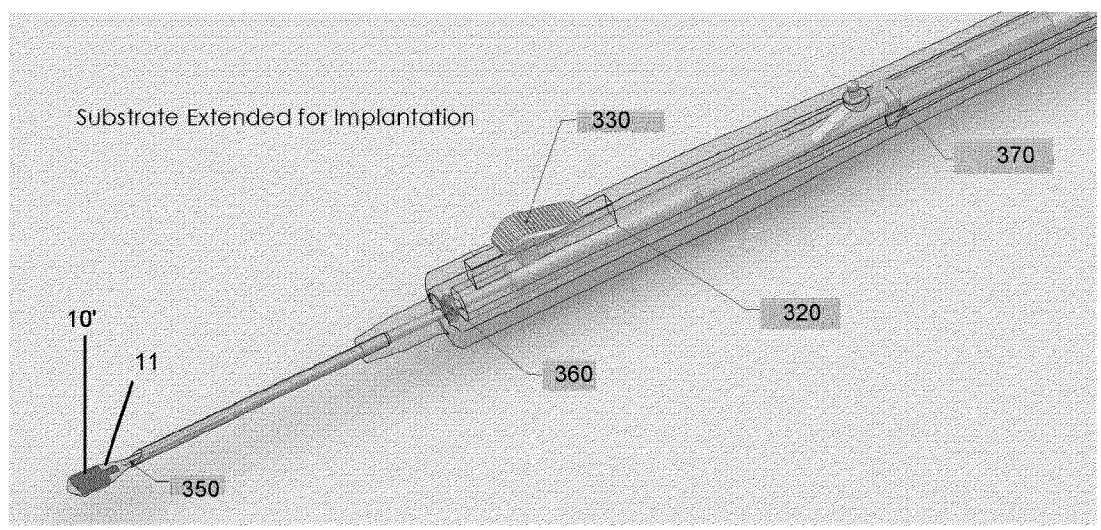
FIG. 27 illustrates an example of a delivery device according to several embodiments disclosed herein. The Figure illustrates the device in an extended position with a cell-seeded substrate on a supporting surface positioned at the distal-most portion of the device (e.g., ready for implantation).

A non-limiting example of a delivery device 300 that is used, in several embodiments, in conjunction with a support surface 11 (e.g., a "launch pad") and a cell-seeded substrate 10' is shown in FIG. 26. In several embodiments, the delivery device comprises a proximal handle 310 (for manipulation of the device by a surgeon), an internal lumen dimensioned for housing an internal shaft 320, the internal shaft being longitudinally moveable within said lumen by manipulation of a control member 330 (e.g., a finger or thumb control). Movement of the control member in a distal direction causes the internal shaft to move in a distal direction and causes at least the distal-most tip of the shaft to extend beyond an outer housing 340. In the extended position (see FIG. 27), the support surface 11 comprising a cell-seeded substrate 10' can be reversibly attached to the distal end of the shaft. In some embodiments, the cell-seeded substrate and support surface are grasped and/or manipulated by forceps 350.

Once a cell-seeded substrate and support surface are attached to the distal end of the shaft, the shaft can be retracted (by sliding the control in a proximal direction). Retraction of the shaft causes the outer housing to induce a rolling of the substrate support surface and the substrate. As discussed above, this rolling is sufficiently tight to allow the substrate to be protected from shear forces during implantation, but not so tight that cells are contacting one another within the roll. In several embodiments, a retaining spring holds 370 the shaft in a retracted position while the device is manipulated by a surgeon to a target site. In several embodiments, a release button is used to subsequently allow the shaft to be moveable. In other embodiments, downward (or another direction) force on the control member allows the shaft to be disengaged from the retaining spring, followed by movement of the shaft in a distal direction. In other embodiments, the retaining spring also functions to limit the distal travel of the shaft, thereby preventing overextension of the forceps/substrate, which could lead to damage to the target tissue or misplacement of the implant.

As shown in the extended position (see FIG. 27) movement of the shaft in a distal direction allows the support surface and cell seeded substrate to exit the outer housing and unfurl. This process, in several embodiments, occurs at or near the target tissue site, just before the final positioning of the substrate. As such, the shear forces and risks of damage to the cells seeded on the substrate are reduced.

Figure 28A:
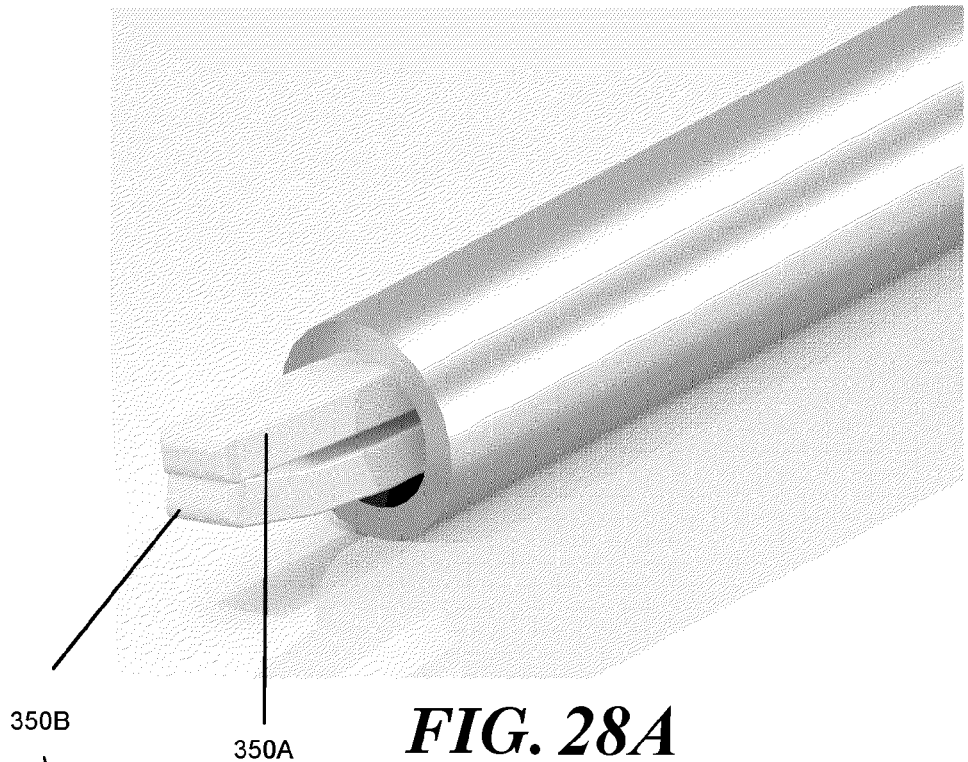
FIGS. 28A-28B depict one embodiment of a device to manipulate substrates as disclosed herein.
Figure 28B:
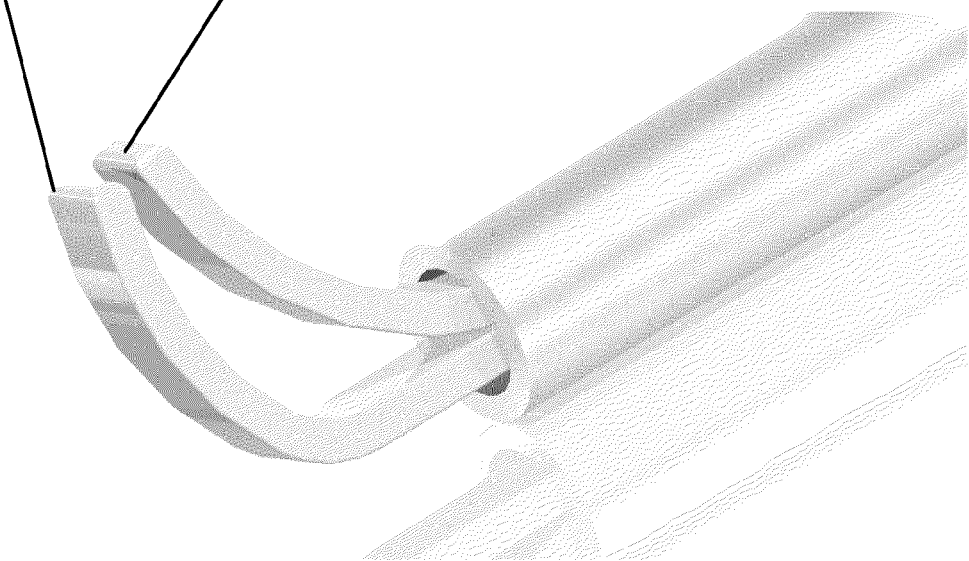
Figure 29A:
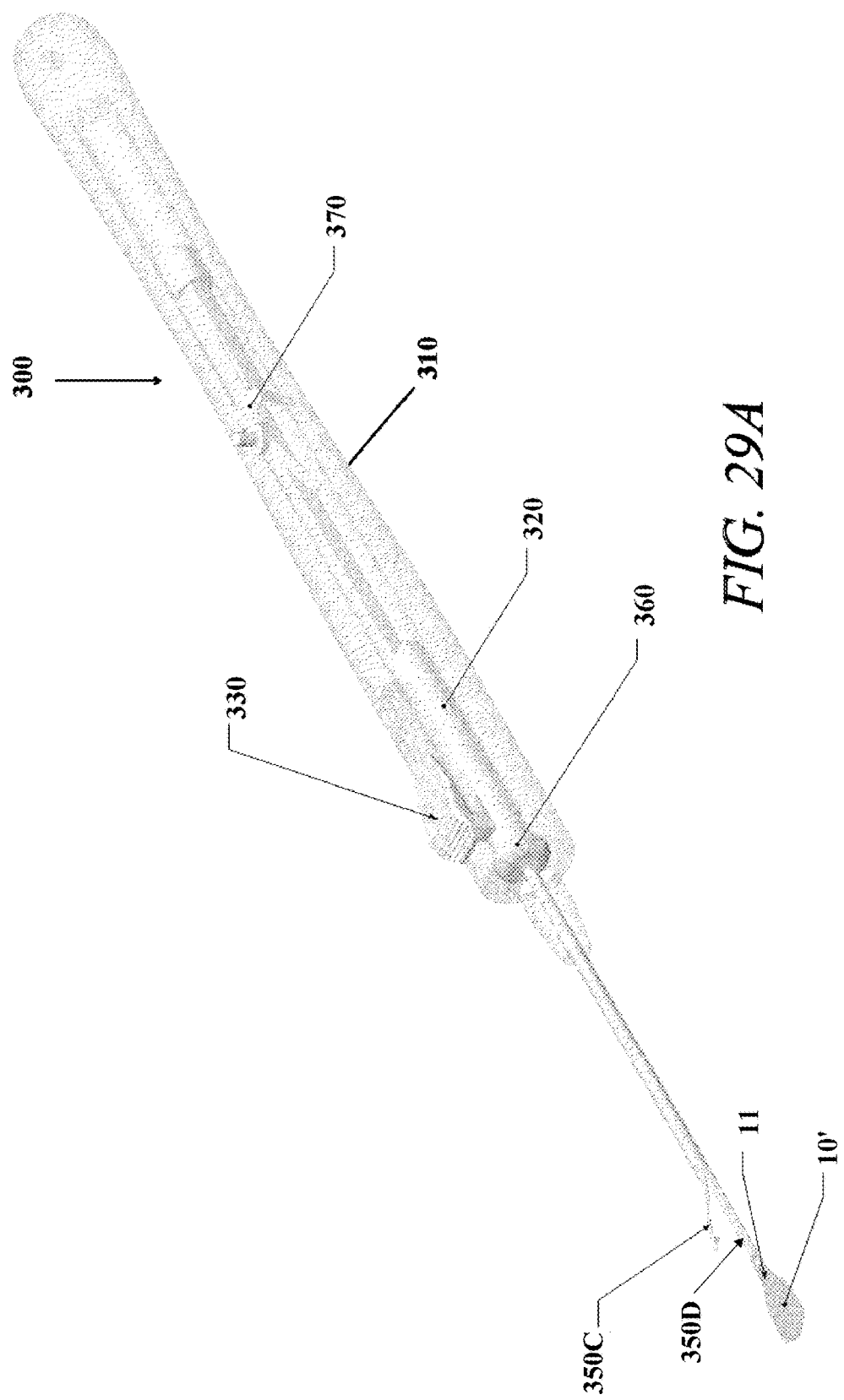
FIG. 29A illustrates an embodiment of a delivery device with an alternate forcep embodiment.
Figure 29B:
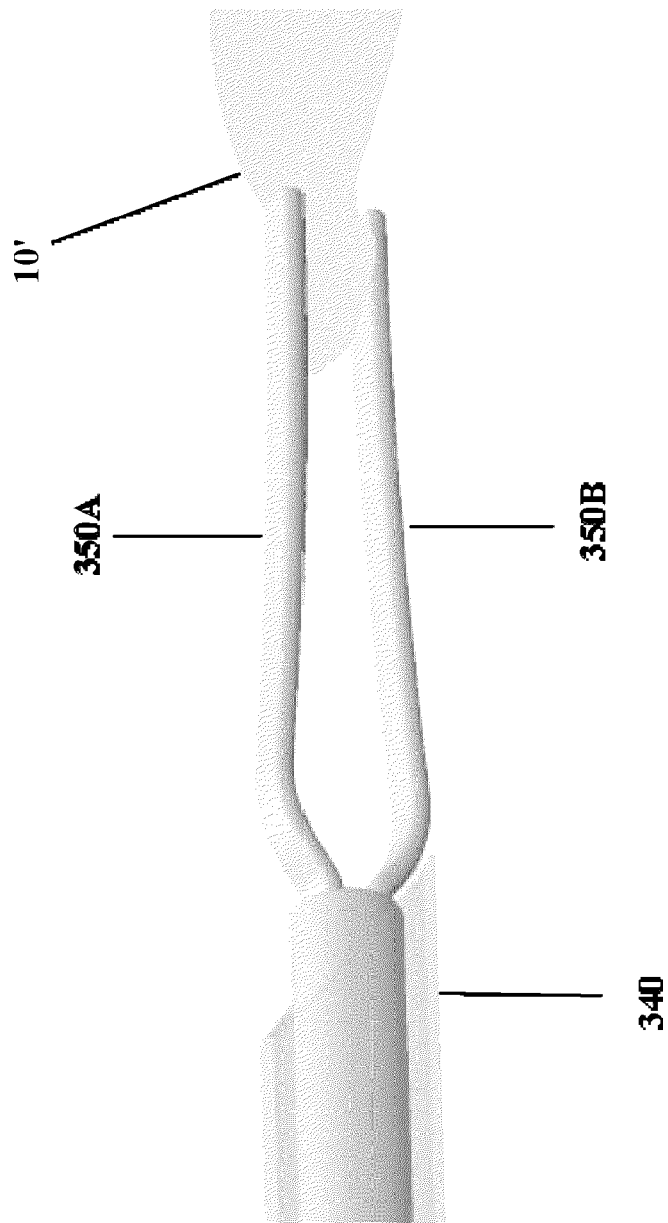
FIG. 29B illustrates an additional alternative forcep configuration.

In several embodiments, forceps such as those shown in FIGS. 28A-28B and described herein are used to grasp the substrate and/or support surface. In some embodiments, as discussed above, forceps themselves retain a curved shape such that, when extended, manipulation and placement of the cell-seeded substrate is made easier. Additionally, in several embodiments, forceps such as those shown in FIG. 29A are used. As shown in FIG. 29A, such forceps may optionally comprise a single "free tine" 350C and a single fixed tine (350D), that, when the forceps are activated, the free tine places downward pressure on the distal portion of the cell-seeded substrate/launch pad to hold it in place against the fixed tine 350B during manipulation/implantation. In particular, in several embodiments, the free tine interacts with a cutout in the tail of the support, for example as shown in FIG. 25. In some embodiments, the "fixed tine" is integrated with, or otherwise comprises, the launchpad. In certain embodiments, this "fixed/free" arrangement reduces the amount of free space in the target tissue required for release of the cell-seeded substrate, is only one of the forcep tines is required to move in order to release the substrate. Moreover, in certain such embodiments, the use of a single free tine increases the control that the surgeon has over the release of the substrate (e.g., the surgeon only has to clear the implant from a single moving part of the insertion device, rather than multiple moving tines). However, in several embodiments, forceps in which both tines are movable (see e.g., FIG. 29B) are also used. In particular, in certain such embodiments, the launch pad is not used (e.g., a substrate alone is implanted), and the manipulation of the substrate is facilitated by the use of forceps with two moving tines (350A, 350B).

Figure 29C:
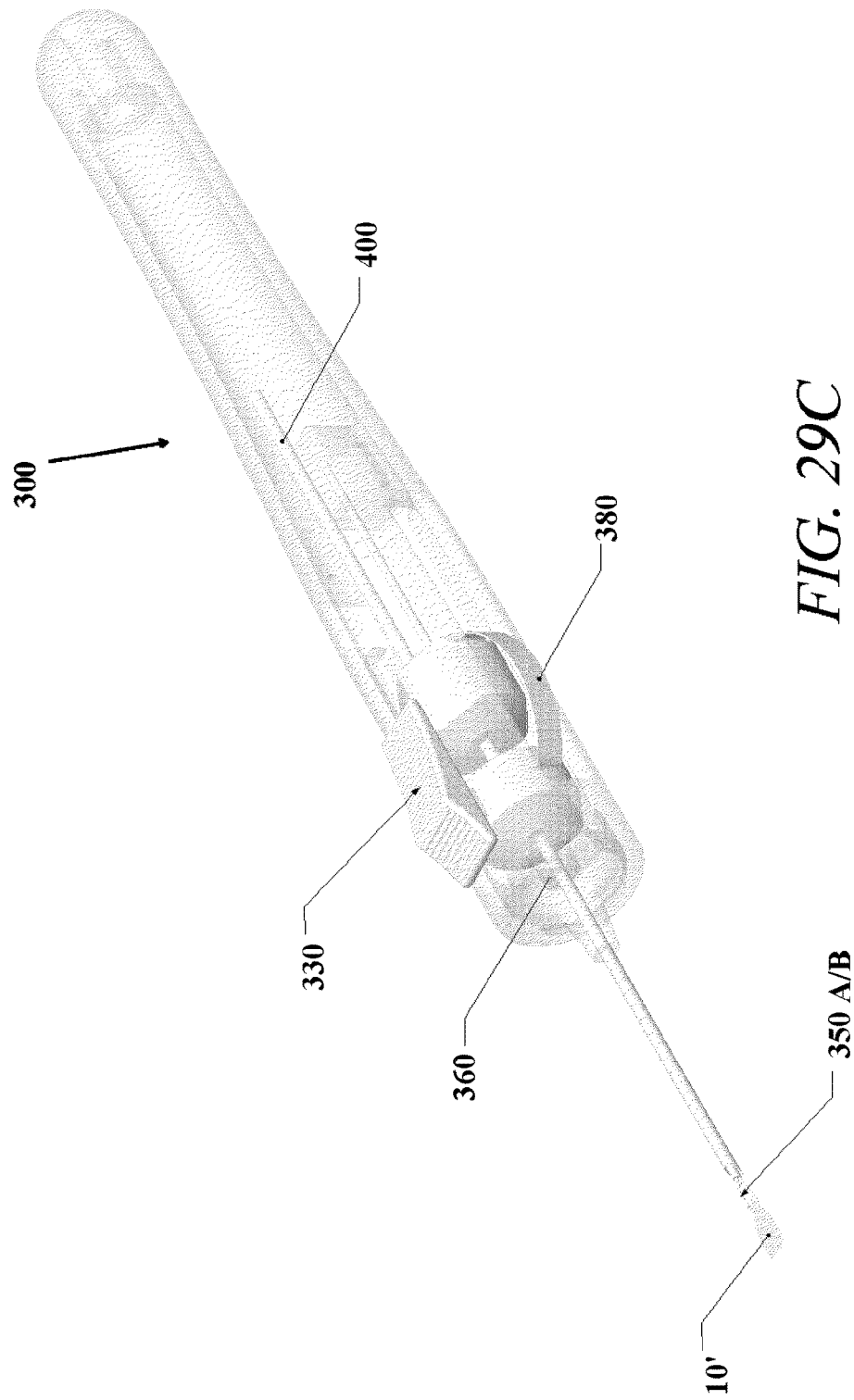
FIG. 29C illustrates an additional embodiment of a delivery device.

As discussed above, activation of the forceps, in several embodiments, is by way of a control mechanism that induces an internal shaft, and thus the forceps, to move in a proximal to distal direction (or distal to proximal direction). In other embodiments an external shaft is induced by a control mechanism (such as those disclosed herein) that surrounds the forceps causing their actuation. In some embodiments, a finger or thumb slide is used (see e.g., 330 of FIG. 29A). In certain embodiments, additional, fine level control is provided to allow precise placement of the substrate in the target space. For example, as shown in FIG. 29C, a fine control element 380 is located at the distal end of the device. In some embodiments, the fine control element comprises a light weight leaf spring that, when a surgeon compresses the spring, causes small movements of the forceps. In this manner, the surgeon can use the control mechanism to adjust the extension of the forceps on a gross scale, and then, at the target site, use the fine control element to ensure precise placement of the substrate at the target site.

The fine control element, in some embodiments, functions in the same way as the control mechanism. In other words, if the control mechanism is a finger slide, the final control may also operate in a sliding motion, though it is optionally activated by a different digit of the surgeon (e.g., the thumb as opposed to a finger). In other embodiments, the fine control element functions in a manner distinct from the control mechanism. For example, in some embodiments the control mechanism is a finger slide, while the fine control elements is a roller device. It shall be appreciated, that any combination of the mechanisms disclosed herein for moving the internal shaft can be used depending, for example, on the preferences of the particular surgeon.

In several embodiments, delivery instruments as disclosed herein optionally comprise a sealing member 360 (for example, on O-ring) that function to seal the interior of the delivery instrument from the external environment. In ocular applications, the sealing member helps to counteract the pressure differential between the intraocular environment and the external atmospheric pressure. In the absence of such a sealing member, there is a risk that the greater intraocular pressure could lead to flow of ocular fluid back up through the delivery instrument (e.g., from a distal to proximal direction), which in some cases could create a suction force on the retinal tissue, thereby leading to retinal damage. In some embodiments, the outer housing 340 is also sealed with a sealing member to further reduce suction pressure on the retinal tissue.

Additionally shown in FIG. 29C is an injection pathway 400, that allows for the delivery of a variety of types of media from the external environment to the target tissue, or to an area surrounding the surgical site the surgical site. For example, in some embodiments, the surgical procedure may require a saline wash around the surgical site in order for the surgeon to have a clear view of the target tissue. Thus, the injection pathway 400, serves as a controlled conduit for the delivery of such media. In some embodiments, pharmaceuticals may optionally be delivered (e.g., anti-inflammatories delivered at the end of the surgical procedure to aid in patient recovery). In some embodiments, the injection pathway advantageously reduces the number of instruments they must be inserted and removed into the target tissue in order to complete the procedure. For example, in certain ocular applications, the injection pathway 400 allows the surgeon to deposit perfluorocarbon into the vitreous cavity in order to tamponade the implanted subretinal implant so that it does not move from its optimum location. In the absence of such an injection pathway, a surgeon would normally have to use a separate instrument to deliver the perfluorocarbon, remove that separate instrument, reinsert an additional instrument, and then complete the procedure.

Figure 29D:
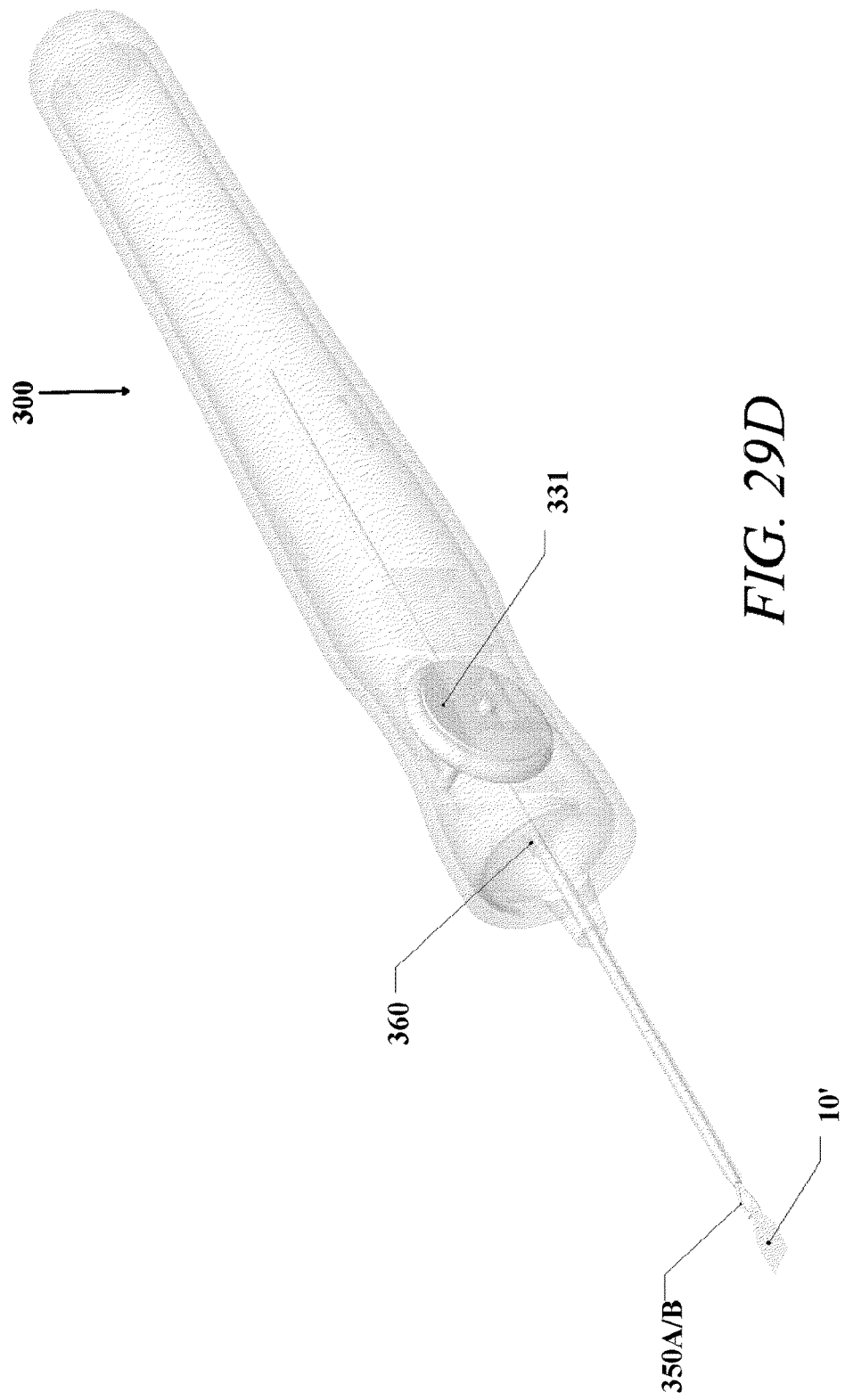
FIG. 29D illustrates an additional embodiment of a delivery device.

FIG. 29D shows an alternative control mechanism 331. In such embodiments, a friction wheel control mechanism can be used. In certain embodiments, a friction wheel control mechanism provides a smooth and fluid extension and retraction movement which, reduces the possibility of inadvertent overextension of the substrate during the implantation procedure. While not shown, certain embodiments using the friction wheel control mechanism further comprise a fine control element. In addition, several embodiments comprise a locking element that can be activated by surgeon in order to lock the control mechanism, the fine control elements, or both such that the extension of the internal shaft, and thus the forceps and the substrate, is fixed.

Figure 29E:
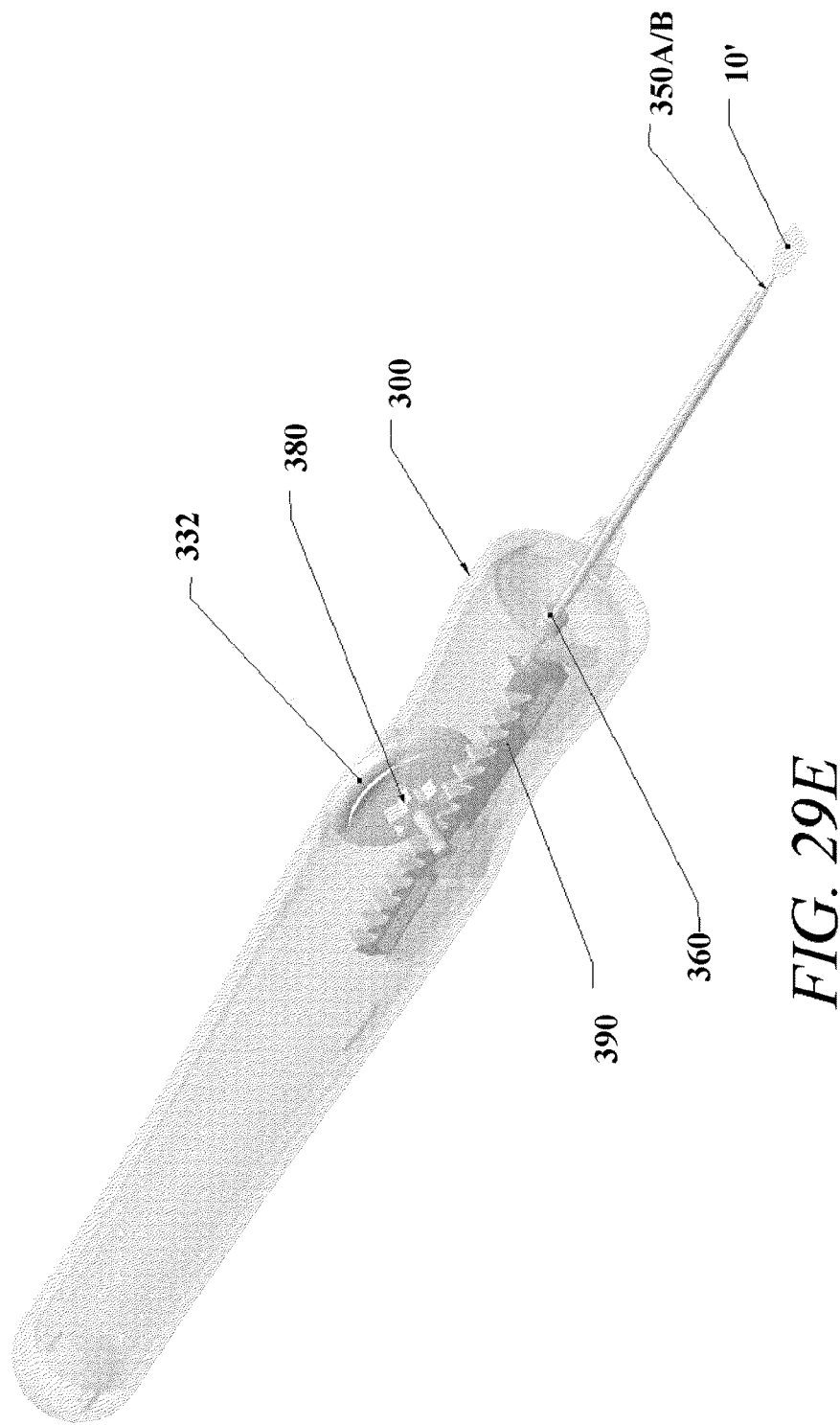
FIG. 29E illustrates an additional embodiment of a delivery device.

FIG. 29E shows an additional embodiment of the control mechanism 332. As shown, a spur gear 380 and rack 390 are housed within the body of the insertion device. In several embodiments, use of a gear and rack provide improved control of the extension and retraction of the forceps, as no slippage can occur, as it might when purely friction-based mechanisms are used. As such, in several embodiments the gear and rack combination provides an improved tactile feel for surgeon, which leads to improved control and more precise placement of the substrate at the target site.

Figure 42:
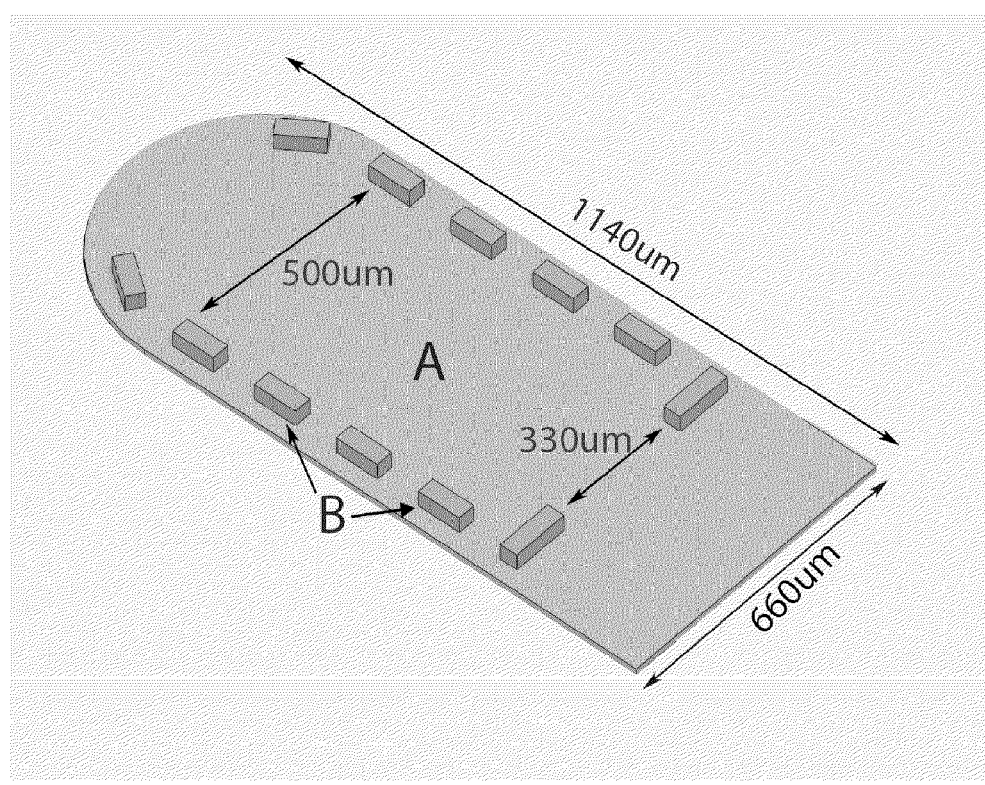
FIG. 42 depicts an additional alternative substrate implantation device.

FIG. 42 shows an additional embodiment of an implantation device in accordance with several embodiments disclosed herein. In some embodiments, the device comprises a platform having upwardly protruding barriers (B in FIG. 42 about 30 μm high) arranged along the edges in the shape of a 'U' (FIG. 42; though other shapes of barrier or placement of barrier are used in other embodiments) which is used to support the cell-seeded substrates during implantation. An embodiment of the platform device with examples of dimensions is shown in FIG. 42. The space inside the barriers acted as the 'substrate loading region' where the substrate for implantation was placed.

In several embodiments, the device is made of parylene, which advantageously can be precisely manufactured to precise dimensions and, in some embodiments, with certain desirable amounts of flexibility imparted to the device. In some embodiments, non-parylene materials are used. In some embodiments, the platform is between about 2 and 20 microns thick, including about 2 microns to about 4 microns, about 4 microns to about 6 microns, about 6 microns to about 8 microns, about 8 microns to about 10 microns, about 10 microns to about 12 microns, about 12 microns to about 14 microns, about 14 microns to about 16 microns, about 16 microns to about 18 microns, about 18 microns to about 20 microns, and overlapping ranges thereof. Thicker platforms may also be used, in other embodiments.

In several embodiments, the dimensions of the platform device are purposefully designed to be larger than the dimensions of the substrate carried by the device. For example, in some embodiments, the width of the platform ranges from about 400 microns to about 1200 microns, including about 400 microns to about 500 microns, about 500 microns to about 600 microns, about 600 microns to about 700 microns, about 700 microns to about 800 microns, about 800 microns to about 900 microns, about 900 microns to about 1000 microns, about 1000 microns to about 1100 microns, about 1100 microns to about 1200 microns, and overlapping ranges thereof.

In several embodiments, the length of the platform ranges from about 600 to about 1500 microns, including about 600 microns to about 700 microns, about 700 microns to about 800 microns, about 800 microns to about 900 microns, about 900 microns to about 1000 microns, about 1000 microns to about 1100 microns, about 1100 microns to about 1200 microns, about 1200 microns to about 1300 microns, about 1300 microns to about 1400 microns, about 1400 microns to about 1500 microns, and overlapping ranges thereof.

In several embodiments, the barriers vary in dimension as well. In some embodiments, the barriers range from about 5 microns to about 50 microns in height, including about 5 microns to about 10 microns, about 10 microns to about 15 microns, about 15 microns to about 20 microns, about 20 microns to about 25 microns, about 25 microns to about 30 microns, about 30 microns to about 35 microns, about 35 microns to about 40 microns, about 40 microns to about 45 microns, about 45 microns to about 50 microns, and overlapping ranges thereof.

The length and width of the barriers varies depending on the embodiment. In some embodiments, the barriers are spaced apart such that fluid (e.g., ocular fluid) can move between the barriers. In other embodiments, the barriers are essentially contiguous with one another. In some embodiments, the distance between the inner portions of the barriers (e.g., those that define the substrate placement area (A in FIG. 42) ranges from between about 250 to about 700 microns, including about 250 microns to about 300 microns, about 300 to about 350 microns, about 350 to about 400 microns, about 400 to about 450 microns, about 450 to about 500 microns, about 500 to about 550 microns, about 550 to about 600 microns, about 600 to about 650 microns, about 650 to about 700 microns, about 700 to about 750 microns, and overlapping ranges thereof. Additionally, placement of the barriers along the surface of the platform device can be varied (e.g., placement relative to the edges of the platform), depending on the embodiment. In some embodiments, (e.g., as shown in FIG. 42) the barriers are placed inboard from the edge of the platform. In other embodiments, the barriers are located closer to (or flush with) the edge of the platform.

EXAMPLES

Examples provided below are intended to be non-limiting embodiments of the invention.

Example 1

Determination of Pore Diameter that Retains RPE Cells

In the eye, a healthy Bruch's membrane functions as a molecular sieve that regulates the exchange of nutrients and metabolic wastes between the retina and the choroid. Based on the sub-retinal location of certain ocular-directed substrates disclosed herein, the porosity of the substrate would ideally simulate these functions of a healthy Bruch's membrane.

To investigate the pore diameter range that would allow for function, cell migration assays were performed. Circular parylene discs were manufactured with varying pore diameters (1, 2, 3, and 5 um) and placed on top of Transwell polyester (PET) cell culture inserts with 8 um pores. Inserts were placed into 24-well culture plates. RPE cells were seeded on the parylene discs with serum free medium inside the PET cell culture inserts and medium containing 20 µg/m recombinant human PDGF (as a chemoattractant) outside the inserts. After overnight culture, the PET insert membranes and the 24-well culture plates that held the inserts were both stained with hematoxylin. Results indicated that RPE cell bodies could migrate through 2, 3 and 5 µm diameter pores, but not through 1 µm pores. Thus it was concluded that pore sizes ranging from about 0.5 to about 1.5 µm are optimal for certain RPE-containing substrates.

Example 2

Biodegradable Polymer Substrates

As discussed above, parylene substrates are used in several embodiments. Biodegradable polycaprolactone (PCL) material compounded with polyethylene glycol (PEG) is used to test the formation of pores in substrates. During polymerization, the PCL-PEG material is spin-coated onto glass coverslips to make thin films of a desired thickness, as discussed above. Cyclic amino acids (Arg-Gly-Asp; cRGD) covalently bound to a PEG-PCL copolymer is annealed onto the surface of the films. Upon treatment with aqueous buffer or media, the water soluble PEG is washed away and creates pores in the film. The ratio of the PCL-PEG affects the degradation rate of the substrate. These pores increase the surface area of the polymer exposed to water and therefore increase the degradation rate. Through this approach both the porosity of the films as well as the degradation rate may be manipulated based on the amount of PEG added to the polymer blend.

Example 3

In Vitro Analyses of hESC-RPE

Figure 11B:
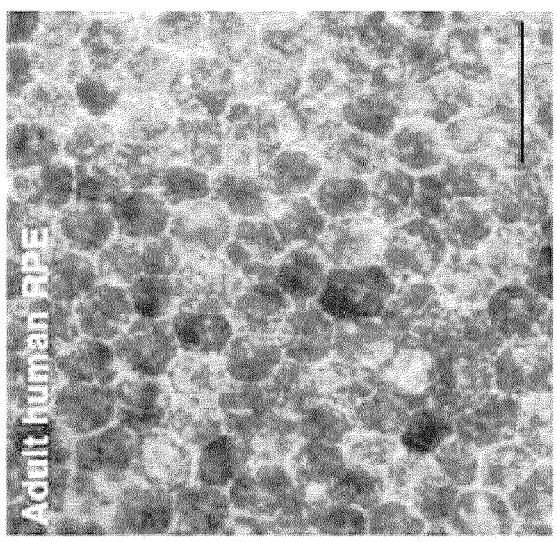
FIGS. 11A-11B depict the similarity between cultured hESC-derived RPE (FIG. 11A) cells and adult RPE cells (FIG. 11B).
Figure 11A:
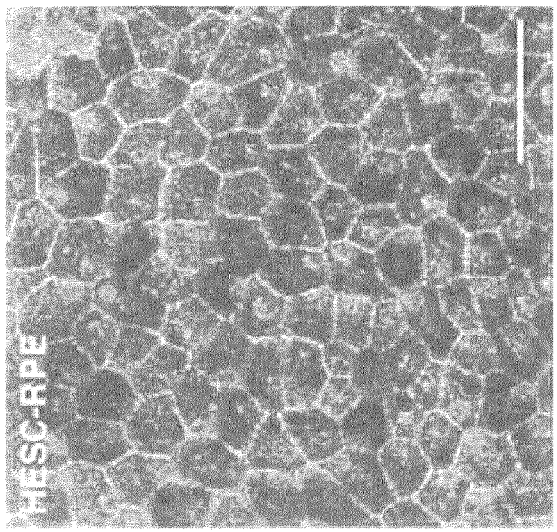

The present example demonstrates that hESC colonies grown to superconfluency, in the absence of FGF2, on mouse or human feeder layers or on matrigel, routinely produce discrete pigmented foci, which grow in size. These pigmented foci can be excised and expanded to produce highly differentiated monolayers that are similar to cultured fetal RPE or adult human cultured RPE. See FIG. 11. Cells can be produced in quantities required for clinical use at 99% purity, as determined by microscopic analysis of pigmented cells as well as quantitative PCR for nanog and Oct-4, markers of possible contaminating undifferentiated hESC. Monolayer cultures are phenotypically stable after prolonged culture (11 months) without passage. Furthermore phenotype and normal karyotype can be maintained for up to at least 4 passages. Based on cell numbers in culture, some embodiments employ about 1.5×10$^5$ cells on a 5 mm diameter substrate are used for each treated eye.

Multiple RPE lines derived from different hESC lines have been characterized with respect to global RNA expression pattern, and quantitative analysis of key RPE marker mRNAs and proteins. Human ESC-RPE are remarkably similar to native human fetal RPE in their expression patterns (correlation coefficient of 0.97 between hESC-RPE and cultured fetal human RPE). Quantitative RT-PCR showed similar levels of RPE-specific transcripts important in gene regulation (Mit-F, OTX-2, Rax, Six-3), pigment synthesis (Tyr, Tryp-1, Tryp-2, Silver), retinol production (CRALBP, RPE65), tight junction formation (ZO-1, Claudin-3), and other key RPE markers (Bestrophin, Emmprin, Transthyretin, Pigment Epithelium Derived Factor (PEDF). hESC-RPE express proteins associated with these transcripts, as well as other crucial RPE markers (integrins, laminins, fibronectin, apoE, fibulin-5, pMe117. The expression of RPE65 by these cells is of particular significance, as deficiencies in this protein leads to blindness.

Figure 12B:
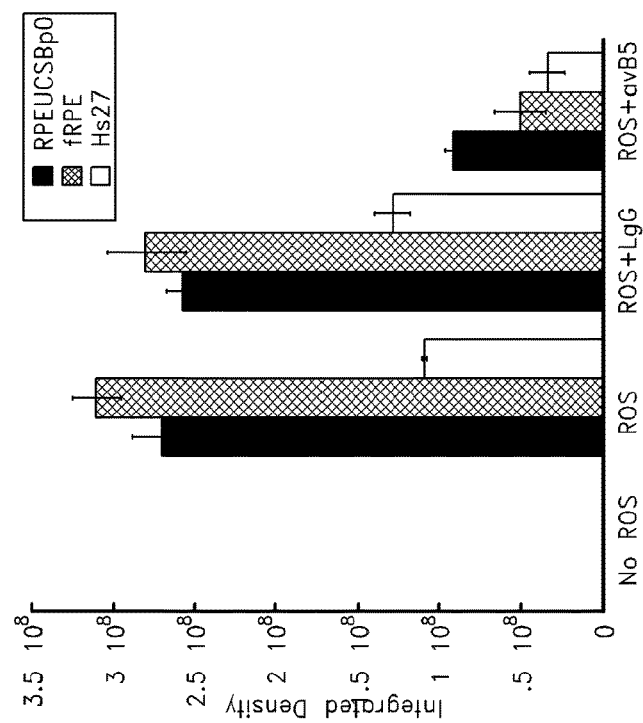
FIGS. 12A-12B depict characteristics of cultured hESC-RPE.
Figure 12A:
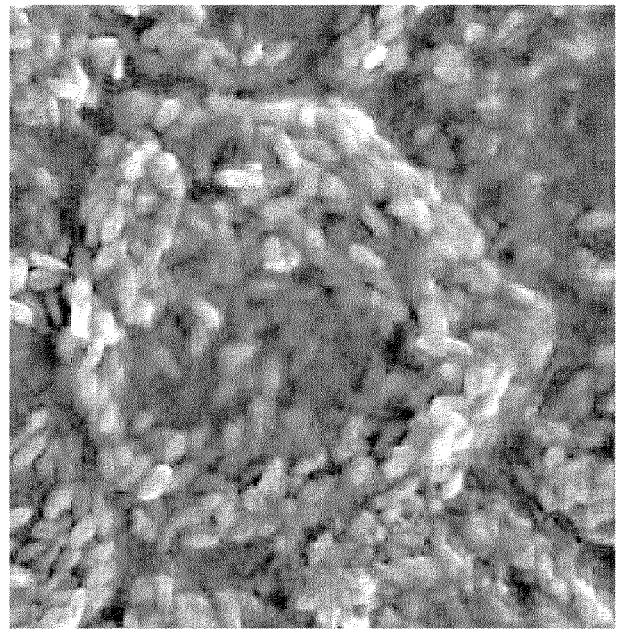

Like native RPE, hESC-RPE monolayers are polarized with apical microvilli, basal nuclei and endfeet, and lateral tight junctions, as detected by electron microscopic analysis and measurement of trans-epithelial resistance (TER). They carry out targeted membrane trafficking with apical localization of Na/K ATPase, integrin alphavbeta5 expression, apical secretion of PEDF, and basal secretion of collagen IV and VEGF. In addition, the apical surface of HESCRPE includes 1-2 cilia per cell that express a-acetylated tubulin, with a 9+0 structure typical of human fetal and early postnatal rodent RPE. Polarized sheets of hESC-RPE express tight junction proteins (occludin, claudin and Z01) localized to cell-cell contact regions typical of mature RPE cells, and generate TER typical of native RPE in situ. See FIG. 12A.

To show that hESC-RPE cells are capable of efficient phagocytosis of photoreceptor outer segments (a process which occurs on a diurnal cycle in vivo and is required for vision), fluorescently tagged photoreceptor rod outer segments (ROS) were added to sheets of hESC-RPE, fetal RPE, or H2S7 fibroblasts (negative control) in vitro and binding/phagocytosis was quantified. See FIG. 12B. hESC-RPE are quantitatively similar to fetal RPE in their phagocytic ability, and that activity was blocked by antibodies to alphavbeta5 integrin or MerTK receptors. Additionally, primary human retina (obtained from macular translocation surgery) were placed onto sheets of hESC-RPE, and phagocytosis of human photoreceptor outer segments was detected.

Additional function analyses are performed in some experiments. For example, in several embodiments isomerization is of all-trans-retinaldehyde to 11-cis-retinaldehyde is evaluated. The is a function performed by the RPE in situ which is important to the visual cycle and maintenance of vision. The ability of hESC-RPE to perform this enzymatic isomerization will be monitored by HPLC analysis of the conversion of all-trans-retinyl palmitate to the 11-cis form in aqueous cell homogenates. Another important function of RPE cells in situ is the phagocytic clearance of shed photoreceptor outer segment membrane. Phagocytosis is monitored using bovine rod photoreceptor outer segments labeled with SNAFl-2 (Molecular Probes) so as to allow differentiation between surface-bound and internalized outer segments. Pigment epithelial derived factor (PEDF) is a major secretory product of RPE cells in situ. It acts as an inhibitor of angiogenesis and has potent neuroprotective properties. Its secretion by cultured human fetal RPE and hESC-RPE is characteristic of establishment of a polarized epithelial monolayer with high trans epithelial resistance in several embodiments, therefore, the presence of PEDF in conditioned medium from hESC-RPE cells is monitored using an ELISA assay.

Example 4

Figure 13B:
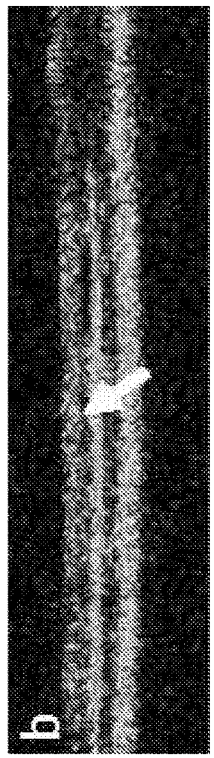
FIGS. 13A-13C depict visualization of post-implantation RPE cells.
Figure 13C:
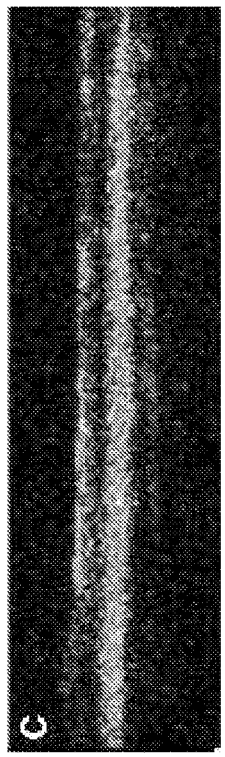
Figure 13A:
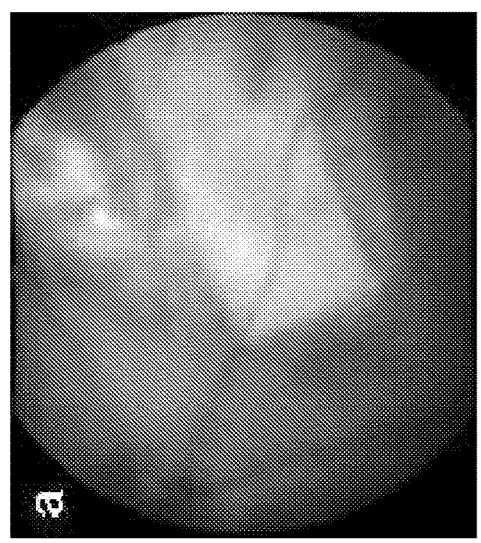

Disease Modifying Activity of hESC-RPE in Animal Models of Retinal Dystrophy hESC-RPE can rescue photoreceptors and visual function. hESC-RPE cells transplanted into dystrophic RCS rat retina survived in the subretinal space, continued their maturation in vivo, and phagocytosed ROS. Some approaches favored subretinal injection of hESC-RPE, our approach is to grow hESC-derived RPE on biocompatible substrates and implant these "patches" into the subretinal space in order to reestablish a functional RPE-photoreceptor interface. Although injected cell suspensions may be easier to perform, delivery of cells on a substrate that mimics Bruch's membrane is used in several embodiments. There are two main reasons for this change of approach. Firstly, the aged macula contains both aged Bruch's membrane as well as aged RPE cells, and this aged membrane does not support attachment and growth of RPE cells. Secondly, a large proportion of injected cells will ultimately be lost in the process due to mechanical, or apoptotic processes; a phenomenon that has been demonstrated in cell-suspension injection studies. In contrast, hESC-RPE grown on polylactic glycolic acid (PLGA; a biodegradable polymer); transplanted into the subretinal space of immuno-suppressed RCS rats, can be precisely imaged by fundus photography and OCT. See FIG. 13. In addition, high resolution imaging is performed and used to evaluate the placement and integrity of subretinal grafts. High speed spectral domain OCT technology (SDOCT), imaging allows for detailed three-dimensional imaging of rodent retina and visualization of various layers. See, for example, FIG. 16.

Figures 14A, 14B:
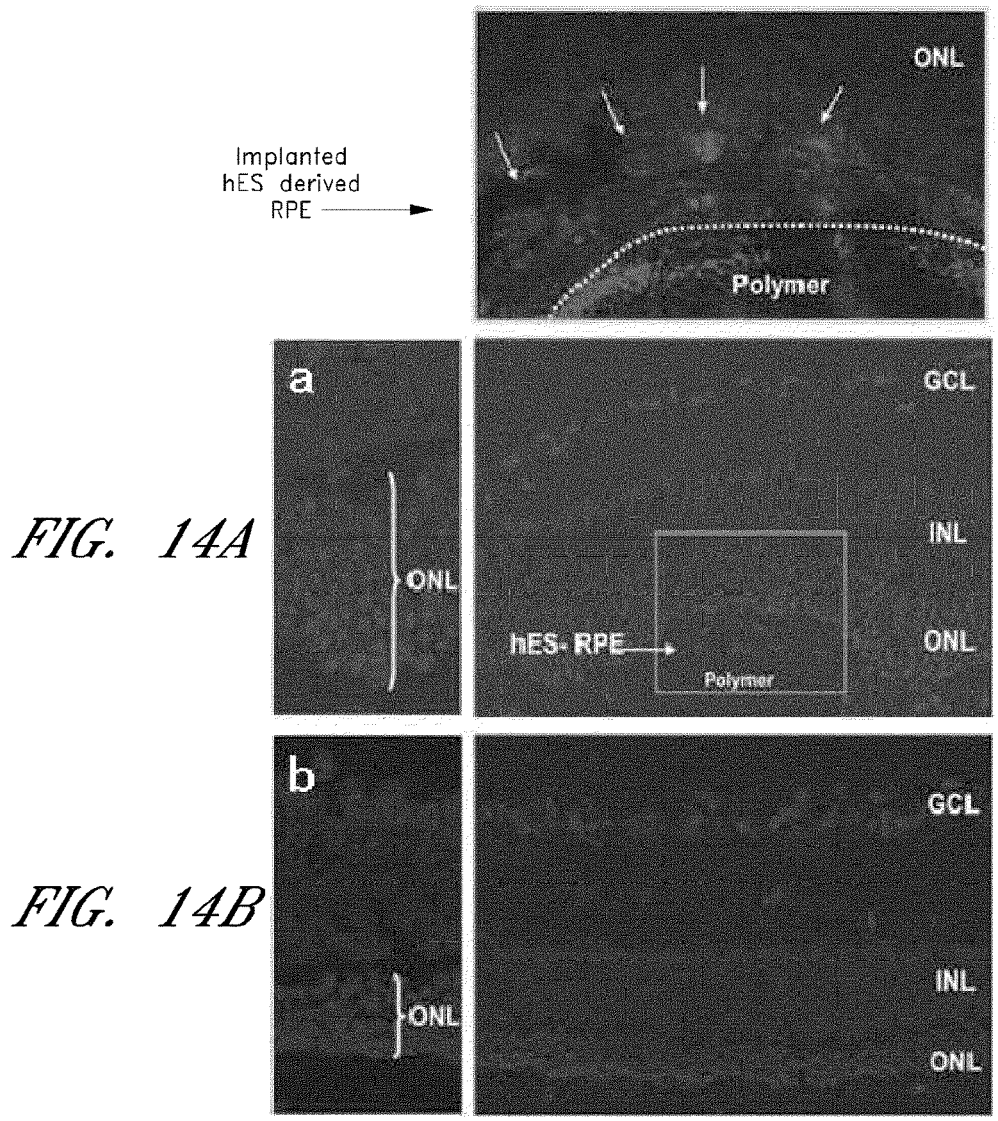
FIGS. 14A-B depict hESC-RPE transplanted into the subretinal space of RCS rats.

The substrate is configured to degrade entirely within 90 days of implantation. Three weeks after transplantation, eyes were processed for pathologic examination. Immunostaining using the human specific marker TRA-1-85 revealed survival of the transplanted hESC-RPE cells in the subretinal space of dystrophic RCS rats and preservation of the overlying photoreceptors in the outer nuclear layer (ONL) compared to adjacent retina, control eyes or polymer-alone injections. See FIG. 14.

Example 5

Treatment of Age Related Macular Degeneration

Age related macular degeneration is a condition found in elderly adults in which the macula area of the retina suffers thinning, atrophy and bleeding. This results in the loss of vision in the central area of vision, particularly an inability to see fine details. AMD is classified as either dry (non-neovascular) or wet (neovascular), with wet-AMD typically leads to more serious vision loss. Dry macular degeneration is diagnosed when yellowish spots known as drusen begin to accumulate from deposits or debris from deteriorating tissue primarily in the area of the macula. Gradual central vision loss may occur with dry macular degeneration. Dry AMD can progress to wet AMD, in which new blood vessels grow beneath the retina and leak blood and fluid. The leakage and pressure build-up damage light-sensitive retinal cells (photoreceptors), which either lose function or die, thereby leading to blind spots in central vision.

RPE transplantation strategies for AMD have been developed over the past 20 years, with the goal of re-establishing the critical interaction between the RPE and the photoreceptor. Advances have come from a large body of animal work and more recently a number of human trials using the patient's own cells. However, current approaches are hampered by complexities in surgical procedure and limitations in cell supply and quality. The most compelling evidence from over 260 homologous and autologous RPE transplants, mostly for neovascular AMD, comes from macular translocation studies. This complex and risky surgical procedure involves detaching and moving the retina so that the damaged macular area of the retina is put into contact with healthy RPE. Although not strictly RPE transplantation, it is functionally an autologous RPE transplantation.

Other strategies for autologous RPE transplantation have evolved from submacular RPE-choroid pedicle flap rotation to sub macular RPE-choroids-free graft transposition, submacular injection of suspension of RPE cells from the peripheral fundus, and currently, submacular insertion of RPE-choroid patch graft from the peripheral fundus. The latter technique involves harvesting an RPE-choroid patch graft from the periphery followed by insertion under the macula and is being used currently by several European groups.

Although these results are encouraging in that vision is restored in many cases, they point out the complexity of procedures that require two large incisions in the retina; the first to harvest and the second to implant. Such large retinal incisions (retinotomies) are associated with high risk of retinal detachment. The approach of using cell suspensions has the added drawback that unattached cells can easily escape into the vitreous cavity, leading to proliferation and scarring on the surface of the inner retina, resulting in complex and often irreparable retinal detachments (proliferative vitreoretinopathy (PVR).

RPE cells have also been transplanted into the brain in clinical trials for Parkinson's disease, since they have been shown to produce dopamine. Relevant to several embodiments disclosed herein, these studies did not detect any tumor formation by RPE. In adult humans, RPE do not replicate extensively, and reports of spontaneously occurring RPE-derived tumors are extremely rare.

Substrates as disclosed herein are used to deliver RPE cells to the sub-retinal space of subjects having AMD to treat the vision loss by facilitating interaction of the RPE cells with the photoreceptors, thereby supporting the photoreceptors and preventing additional loss of function or death of the photoreceptors.

In vivo studies in rat models of AMD are performed. Substrates seeded with RPE cells are delivered to treated animals and compared to diseased rats receiving sham (e.g. empty) substrates or sham operated normal rats.

Clinical follow-up and characterization is performed on both treated rats and controls. Clinical assessment is done using fundus angiography (FA) (to assess vasculature health), fundus photography, fundus autofluorescence (FAF), optokinetic nystagmus (OKN), electroretinography (ERG), and multifocal ERG (mfERG). Histopathologic assessment of animals is performed for evidence of local tumor/teratoma formation, maintenance of a differentiated RPE phenotype of the transplanted cells with lack of cell proliferation (immunohistochemistry using cell cycle specific antibodies), migration of cells away from the monolayer, cell loss or damage to adjacent photoreceptors or Bruch's membrane/choroid complex, and inflammation (macrophages, T-cells), or reaction to the substrate. Transplanted hESC-RPE will be identified by monitoring expression of a human marker protein (TRA-1-85). The need for immunosuppression is evaluated by measuring expression of MHC Class I and II in vitro (with and without activation by interferon-gamma) and in vivo by immunohistochemistry. Treated rats exhibit improved clinical assessment with respect to one or more of the parameters measured.

Example 6

Generation of Substrates Containing Stem Cells

As discussed above, in several embodiments, hESC-RPE can be differentiated into polarized monolayers on biodegradable and non-biodegradable substrates. In several embodiments, cells are pre-grown on a substrate that is eventually incorporated into a three dimensional substrate cage for implantation. A sheet of suitable substrate, such as a polycaprolactone and polyethylene glycol (PCL-PEG) co-polymer is polymerized at the desired thickness. While polymerizing, the co-polymer is optionally spin-coated on a coverslip to tailor the thickness. A cyclic amino acid containing PCL-PEG co-polymer is annealed to the polymerized substrate. Aqueous media is then added to dissolve the water soluble PEG and generate pores. The porous substrate is then sterilized. Stem cells are then cultured on the sterilized sheet to a desired cell density. One or more pieces of cell-supporting substrate are then cut from the sheet, aligned and annealed with one or more additional pieces of co-polymer to generate a cell-containing three-dimensional substrate cage suitable for direct implantation.

Figure 15B:
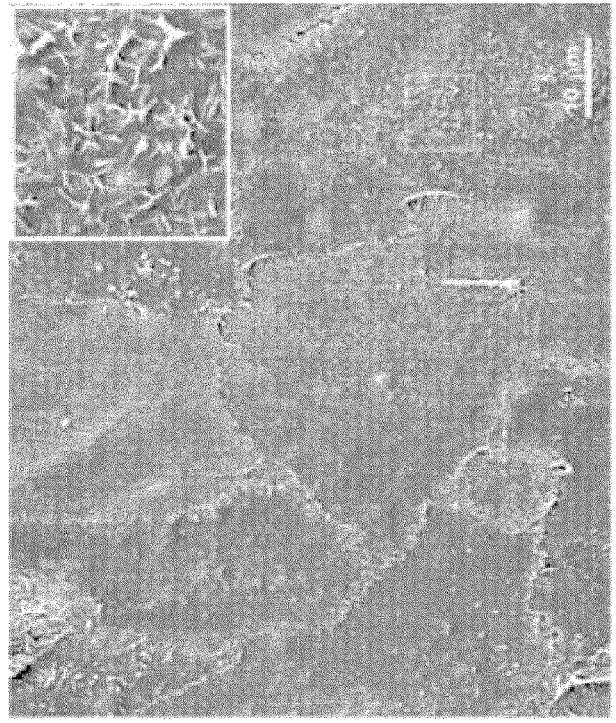
FIGS. 15A-15B depict growth of cells on various substrates in accordance with several embodiments herein.
Figure 15A:
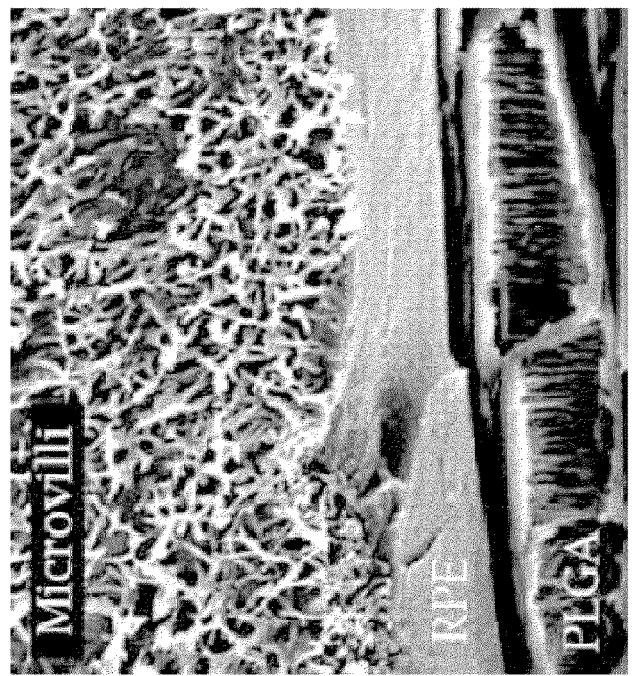

In several embodiments PLGA is used to form a biodegradable substrate. As shown in FIG. 15A, hESC-RPE grown on PLGA show well developed apical microvilli after 3 weeks of culture. Other embodiments employ non-biodegradable material. hESC-RPE grown on surface-modified non-biodegradable parylene also show excellent attachment and development of apical microvilli (see inset of FIG. 15B) within 48 hrs of culture. While in some embodiments cells are grown on a substrate prior to fabrication of the final substrate, in other embodiments, cells are deployed into a fully fabricated substrate prior to implantation.

Example 7

Generation of Substrates Configured to Receive Stem Cells

As discussed above, in several embodiments, substrate cages are fabricated that can later have one or more varieties of stem cells deployed within the substrate cages prior to implantation in a target tissue. Two molds are created that correspond to a top (apical) and bottom (basal) portion of the desired three-dimensional substrate cages. The molds are configured to yield an inner lumen upon the assembly of the two portions of the substrate cages and an access means to delivery stem cells to the lumen post-assembly. A polymer is polymerized within each portion of the mold. Upon polymerization, the polymer is removed from its mold and exposed to an aqueous media to generate pores within the substrate. The pores are configured to retain cells within the final substrate cage and still allow interaction (physical, chemical, or otherwise) between the cells a target tissue. The two polymeric portions are then aligned and annealed to generate a three-dimensional porous substrate cage that is suitable to receive stem cells and then be implanted into a recipient in order to generate a therapeutic effect in said recipient through the interaction of the cells and the target tissue.

Example 8

Interdigitation of hESC-RPE and PR Outer Segments in Rat Eye

Using the surgical tools disclosed herein and a parylene substrate comprising at least one planar cell-growth surface, interdigitation of H9 hESC-RPE with photoreceptor (PR) outer segments was demonstrated. The Royal College of Surgeons (RCS) rat is an established animal model for inherited retinal degeneration. The genetic defect in RCS rats causes the inability of the retinal pigment epithelium (RPE) to phagocytose shed photoreceptor outer segments. hESC-RPE cells were seeded onto parylene substrates and grown in accordance with the techniques described above. Once the RPE cells has grown to confluency, an substrate was implanted into the RCS rat eye, with the cell growth surface juxtaposed with the outer nuclear layer of the photoreceptors. Control substrates (no cells) were implanted into RCS rats for comparison.

Figures 30A, 30B:
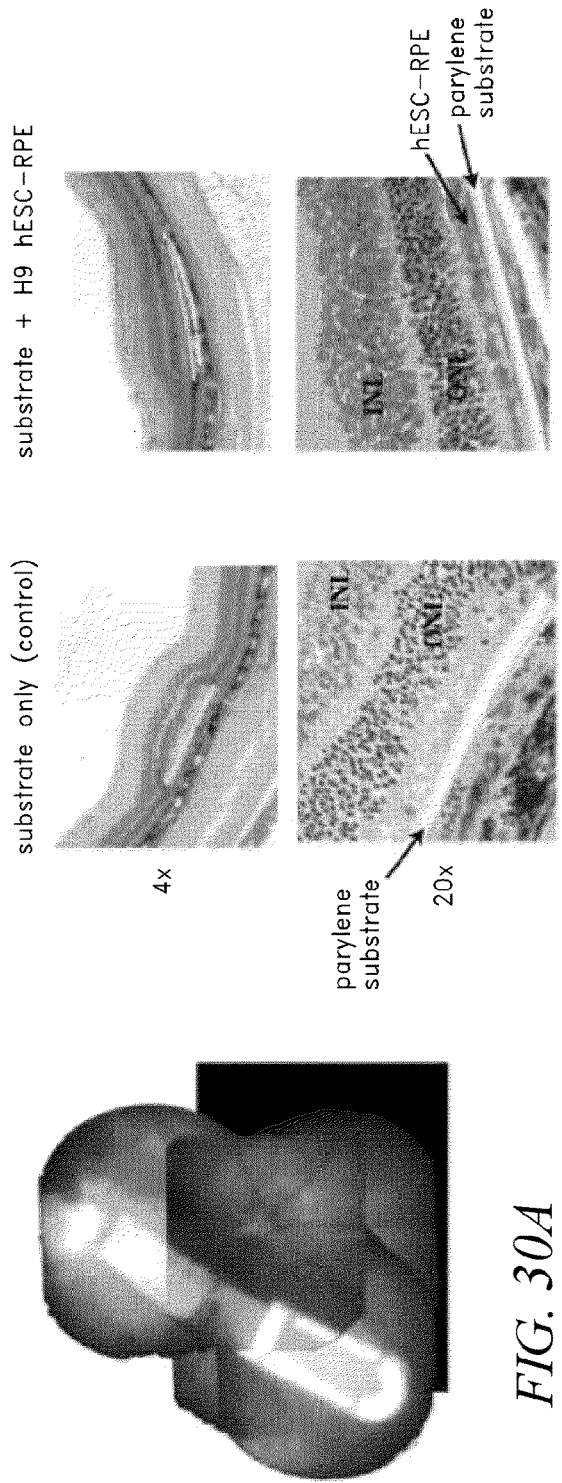
FIGS. 30A-30D depict histological results from implantation of a stem cell-seeded substrate implanted in a rat eye.
Figure 30D:
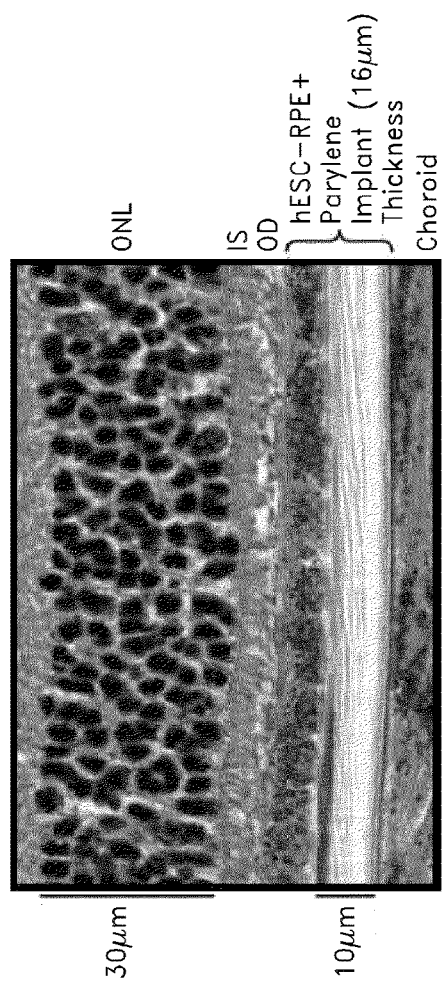
Figure 30C:
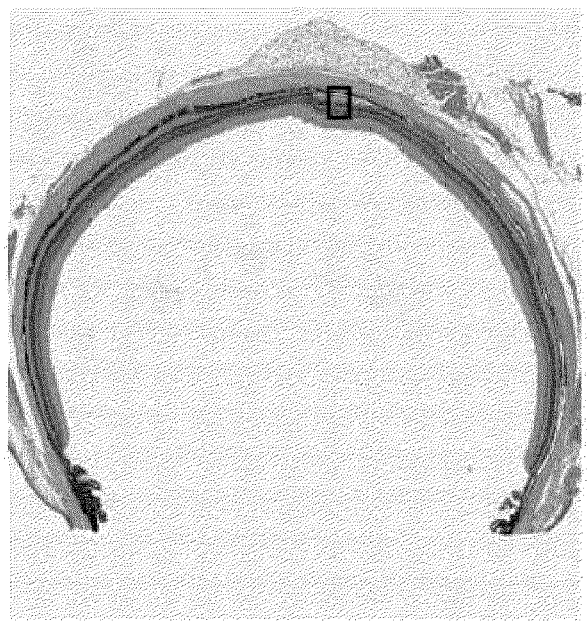

FIG. 30A shows a stitched fundus photo of implanted parylene substrate in the RCS rat eye. FIG. 30B depicts hematoxylin and eosin (H & E) staining one week post-implant in RCS rat. The lower right panel of FIG. 30B shows that hESC-RPE interdigitate with PR outer segments. The majority of the hESC-RPE are retained on the apical surface of the substrate. Unseeded control substrates show no such connectivity (30B lower left panel). FIG. 30C shows a cross-section of isolated orbit of implanted rat (1 week post-implant). FIG. 30D is a high resolution close-up of the parylene substrate seeded with hESC-RPE. Interdigitation and localization of RPE somas on substrate surface can be seen.

Example 9

Human Embryonic Stem Cell Derived Retinal Pigment Epithelial Cells Cultured on Polymer Substrates Maintain a Confluent Monolayer Structure in the Subretinal Space of Implanted Rats Age-related macular degeneration (AMD) is the leading cause of blindness in the United States. The retinal pigment epithelium (RPE) is a monolayer of cells which is critical for maintenance of photoreceptor function. Degeneration of the RPE is one of the main contributing factors to pathogenesis of AMD which leads to degeneration of the retina. Transplantation of in vitro expanded RPE grafts has great potential in treatment of AMD.

The Royal College of Surgeons (RCS) rat has a naturally occurring mutation of the receptor tyrosine kinase gene Mertk. This mutation causes a defect in RPE phagocytosis and results in secondary retinal degeneration. The RCS rat is a well-accepted animal model for studying AMD and associated therapies. The present study was performed to determine if human embryonic stem cell derived retinal pigment epithelial cells (hESC-RPE) cultured on the biocompatible polymer parylene as a monolayer are suitable for transplantation into the subretinal space (to further support the findings shown in the Examples above) and to evaluate the preservation of hESC-RPE seeded parylene substrates in implanted dystrophic and normal rats, and the ability of monolayer integrity to be preserved.

Methods

Cell Preparation

RPE cells derived from H9 human embryonic stem cells were cultured on 10 µm thick matrigel-coated parylene substrates (0.4 mm×0.9 mm) for 4 weeks until a polarized monolayer was generated. Other substrates or other sizes of substrate may be used in other embodiments.

Animals

Pigmented dystrophic RCS rats (n=4) and normal Copenhagen rats (n=3) between postnatal day 30 to 35 were used for transplantation.

Transplantation

Rats were anaesthetized with a mixture of 37.5 mg/kg ketamine and 5 mg/kg xylazine. The eye was then rotated inferiorly with traction suture. A 0.5 mm scleral incision was made with a needle. Aqueous fluid was released through a puncture at the limbus to decrease pressure in the eye. Balanced salt solution was injected into the subretinal space to create a bleb for insertion of the implant. The implant was then gently inserted into the subretinal space, and position was confirmed by fundus examination using a contact lens under the surgical microscope. Prednisolone was administered to the rats through drinking water (2 mg/ml) for the entire period of study.

Pre- and Post-operative Examinations

Fluorescein angiography, autofluorescence imaging, and spectral-domain optical coherence tomography (SD-OCT) (Spectralis HRA+OCT, Heidelberg Engineering, Germany) were performed. Animals were euthanized and eyes enucleated one month after surgery. Tissue sections were subjected to histological evaluation using hemotoxylin and eosin staining.

Figure 31:
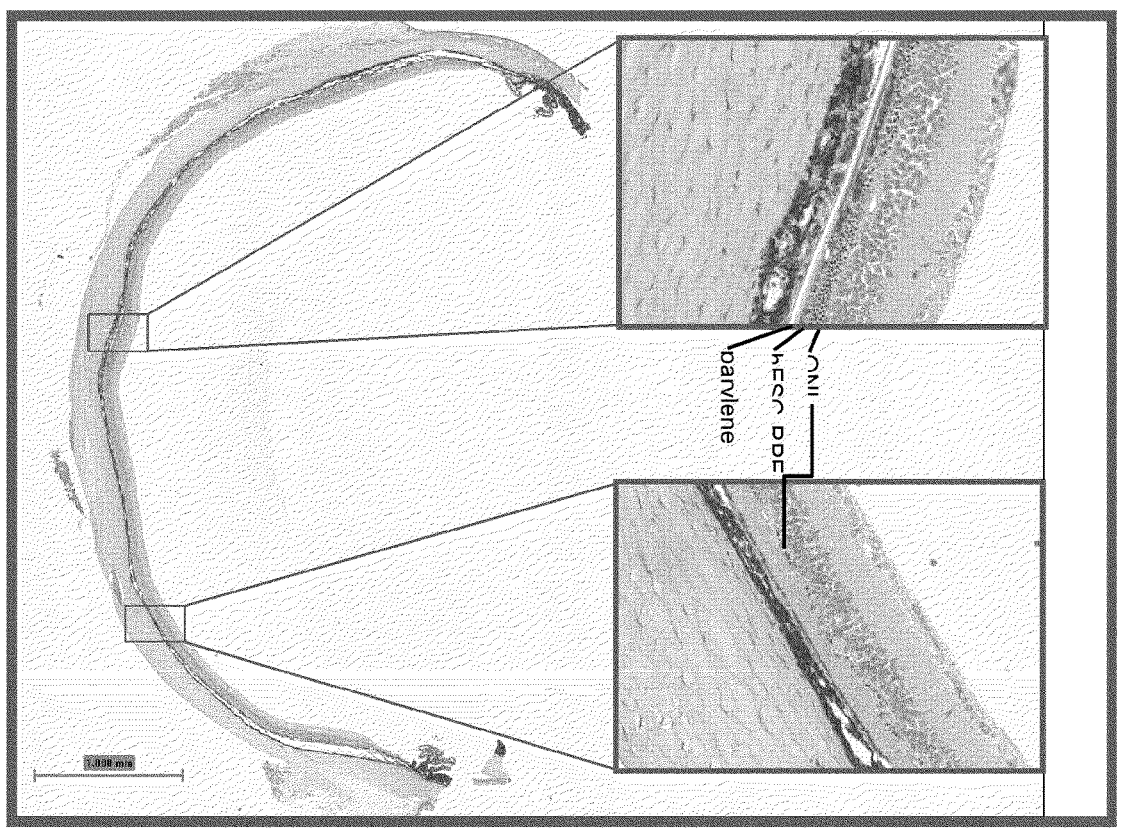
FIG. 31 depicts histology of the retina of a Royal College of Surgeons rat two months after cell-seeded substrate implantation.

Results hESC-RPE cells were observed in the subretinal space in all implanted rats. A confluent monolayer of RPE attached to the parylene was observed in all the RCS rats (4/4) and 66% of Copenhagen rats (⅔). No difference was observed between the RCS rats and the Copenhagen rats in terms of survival of transplanted cells. There were no signs of ocular tumor formation or cell migration in sectioned samples up to one month after surgery. As shown in FIG. 31, the RCS retina showed retained monolayer of hESC-RPE cells on the parylene substrate two months after surgery and retained 3-5 layers of outer nuclear layer (ONL) (upper inset). In contrast, regions distal to substrate location have ONL decreased to 1 or fewer layers (0-1), (lower inset) indicating photoreceptor rescue over the RPE implanted area.

Figures 32A, 32B, 32C, 32D:
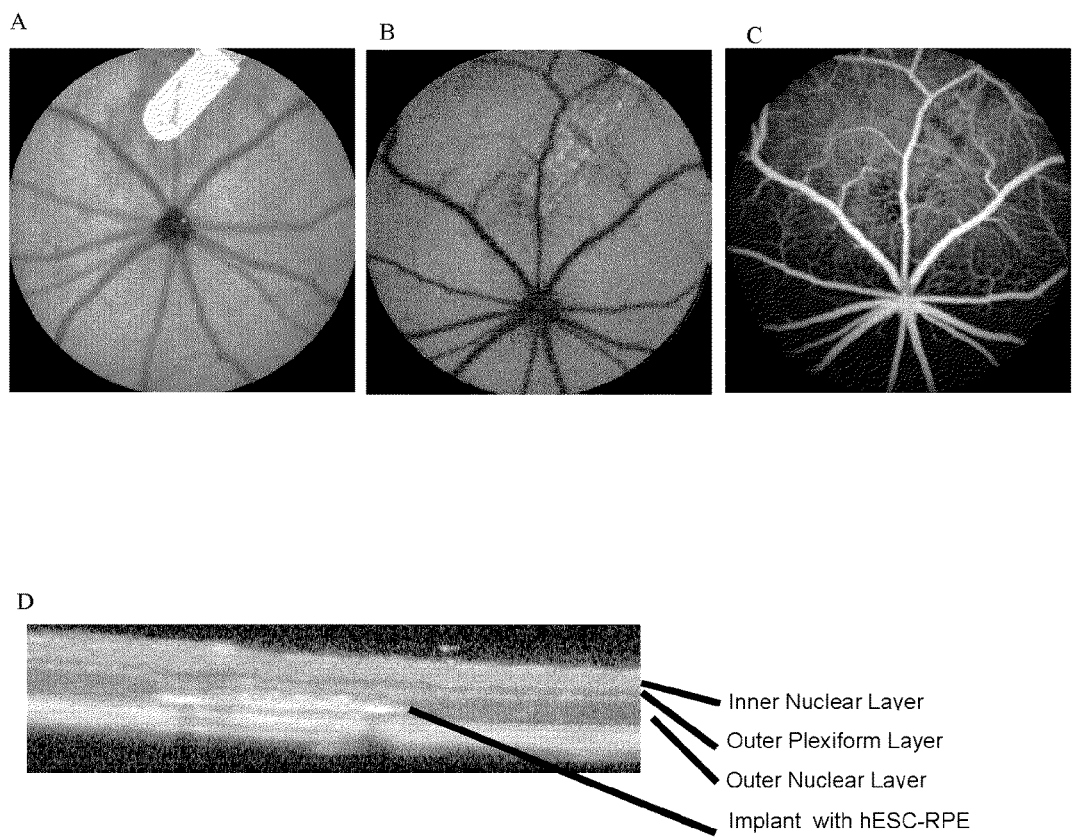
FIGS. 32A-32D depict various images of normal Copenhagen rat ocular tissues after cell-seeded substrate implantation.
Figure 33A:
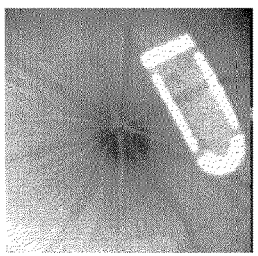
FIGS. 33A-33C depict various images of RCS dystrophic rats after cell-seeded substrate implantation.
Figure 33B:
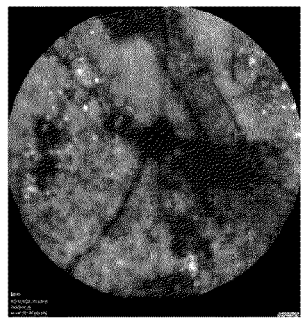
Figure 33C:
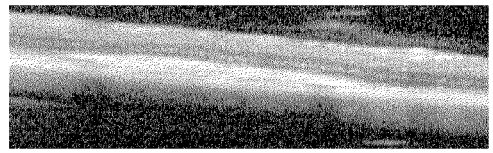

As shown in FIG. 32A, one month after transplantation, the location of the substrate is readily observable by infrared imaging of the fundus. In FIG. 32B, an autofluorescence image shows punctate hyperautofluorescence over the substrate. These areas of punctate hyperautofluorescence are represenetative of RPE cells that are not only surviving after transplant, but are functional. The hyperautofluorescence is due to the lipofuscin fluorescing in active RPE cells (lipofuscin is a metabolic byproduct of lysosomal digestion of lipids, which indicates that the RPE cells are actively phagocytosing the outer disks of the photoreceptors). Thus, these data not only indicate the long-term stability of the RPE cells on the substrate, but also the functional nature of the transplanted cells. FIG. 32C depicts late phase fluorescein angiography indicating that the substrate does not disturb the retinal and choroidal vasculature. The outline of the substrate can be delineated due to blocked fluorescence by the titanium foil around the implant. FIG. 32D depicts an OCT image showing the substrate located in the subretinal space. FIGS. 33A-33C depict similar analysis in dystrophic RCS rats.

From this study it can be concluded that HESC-RPE cells cultured on parylene substrates can be successfully implanted into the subretinal space of rats and that the cells survive as a monolayer for up to two months without immune rejection when immunosuppressant is used. In several embodiments, survival time is greater than 2 months, e.g., 6 months, 12 months, or several years. In several embodiments, immune suppression is not required for the long-term survival of the implanted RPEs. Moreover, these data demonstrate preservation of the outer nuclear layer in implanted eyes.

Example 10

Quantitative Analysis of Possible Surgical Shear Force Stress on Polymer Substrates Seeded with Human Embryonic Stem Cell (hESC) Derived Retinal Pigment Epithelium (RPE) Monolayers Implanted into the Rat Subretinal Space As discussed above, RPE dysfunction can lead to photoreceptor loss and deteriorated vision. hESCs have been considered a promising source of replacement of RPE cells. According to several embodiments, hESC-RPE are cultured as a monolayer on parylene substrates for implantation into the subretinal space of a diseased eye. The present study demonstrates that implantation of hESC-RPE cells in rats rescues photoreceptors and controls deterioration of visual function. In particular the present study set out to evaluate the feasibility of a surgical approach for implantation of RPE monolayer in the subretinal space of an animal model of RPE dysfunction, to quantify the number of cells present on the substrate before and after implantation, and to determine whether surgical shear force during implantation can affect the preservation of the RPE monolayer.

Methods

Animals and Implants

Dystrophic Royal College of Surgeons (RCS) rat pups (n=10) received RPE-seeded (hESC (H 9) derived RPE) substrates at post-natal day 28. hESC (H 9) derived RPE cells were cultured as a monolayer on 10 μm thick parylene substrates divided into rectangular pieces (0.4 mm×0.9 mm). Other types of substrate of other dimensions are used in other embodiments.

Surgical Procedure

With the help of a fine forceps, the parylene substrates were placed into the subretinal area. The placement was confirmed by fundus examination and OCT b-scan (Heidelberg Spectralis HRA+OCT; Heidelberg, Germany).

Histological Procedure

One day after implantation, animals were sacrificed and the eyes were subjected to histological examination using hematoxylin & eosin staining.

Quantitative Estimation of the hESC Derived RPE

The total number of cells seeded on the substrate prior to implantation was calculated from photomicrographs. High resolution images of retinal sections passing through the substrate were captured using an Aperio ScanScope, which allows for quantification of different cell classes. Cell count was compared before and after implantation.

Results

Figure 34A:
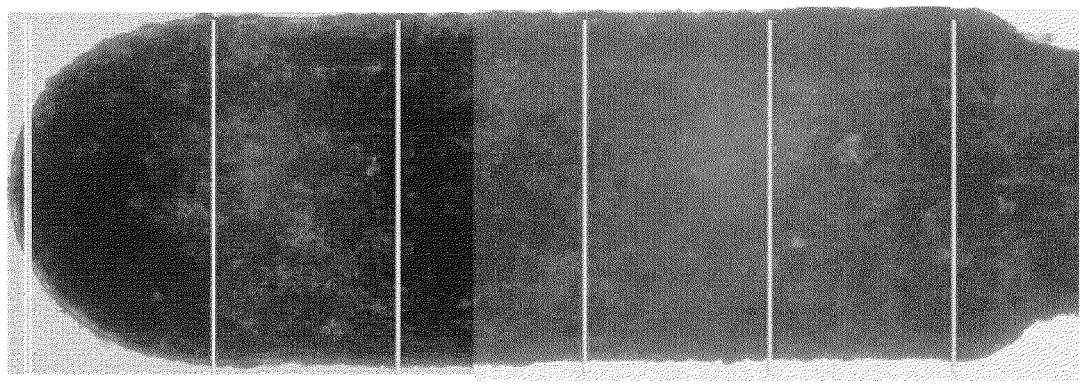
FIGS. 34A-34B depict an RPE-seeded parylene substrate (A) and the calculated number of RPE cells/row (B) after seeding the substrate and culturing to monolayer formation.
Figure 34B:
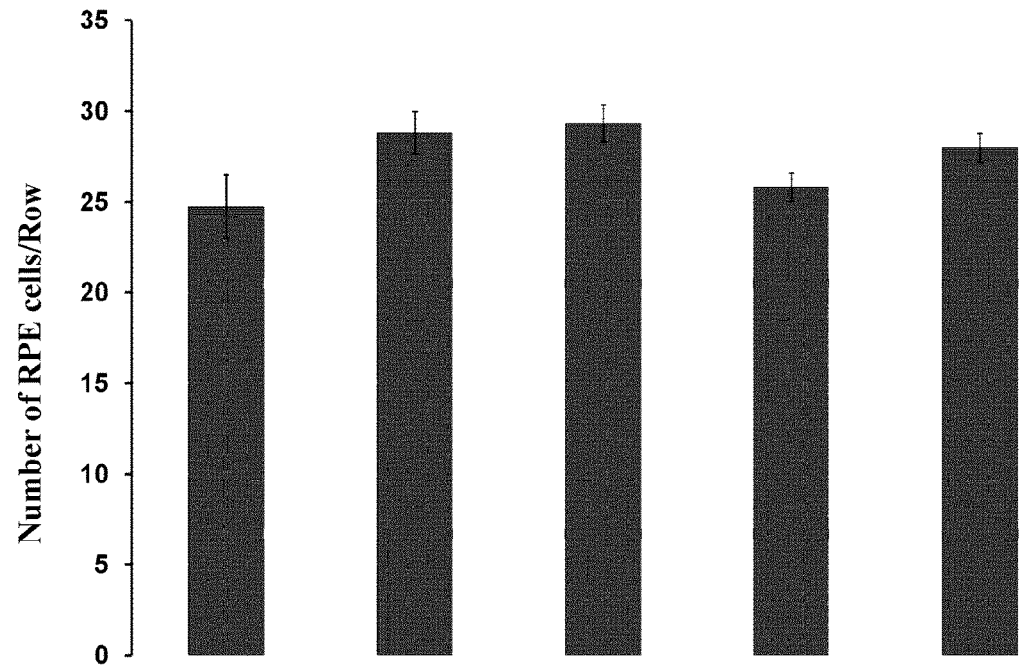
Figures 35A, 35B, 35C, 35D, 35E, 35F, 35G, 35H:
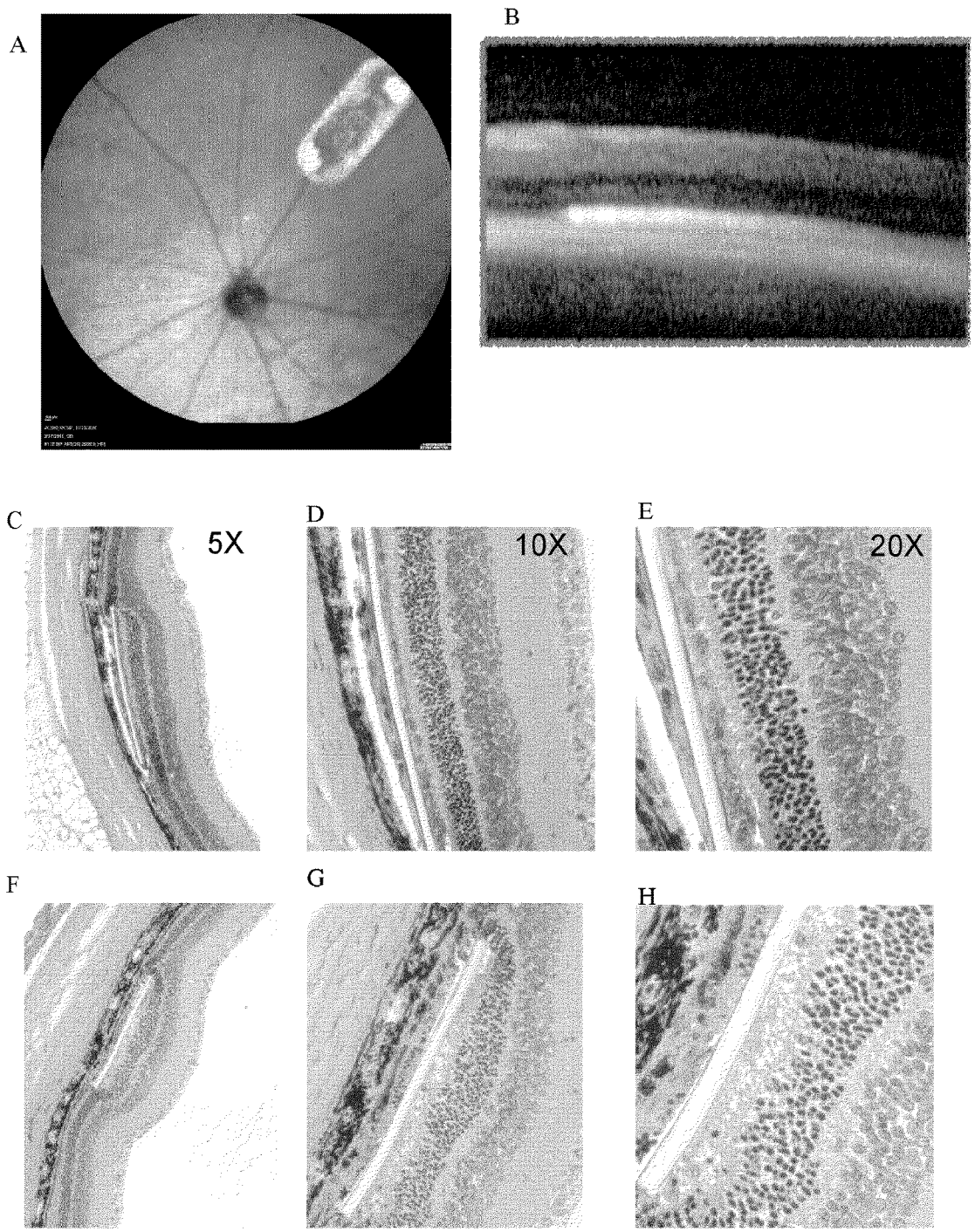
Figure 36A:
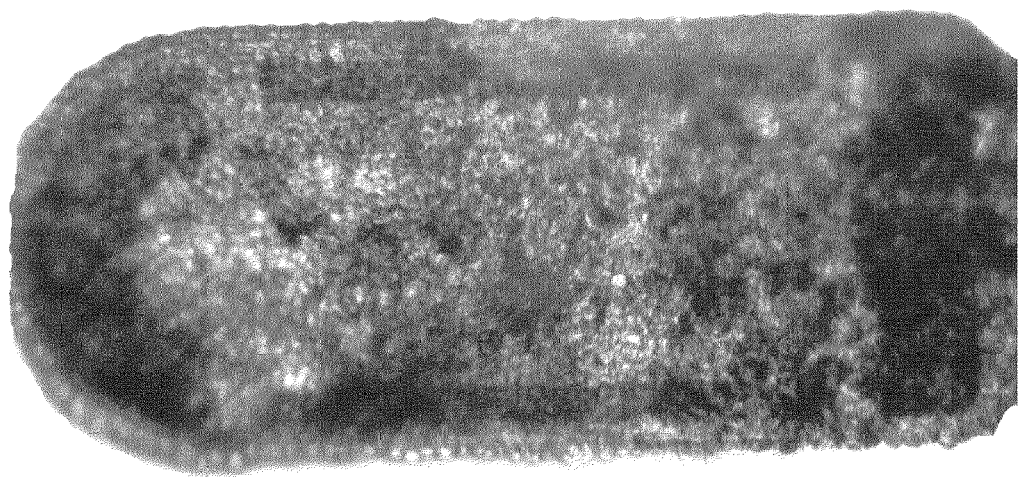
FIGS. 36A-36B depict an RPE-seeded parylene substrate (A) and the calculated number of RPE cells/row (B) one day after implantation in the rat subretinal space.
Figure 36B:
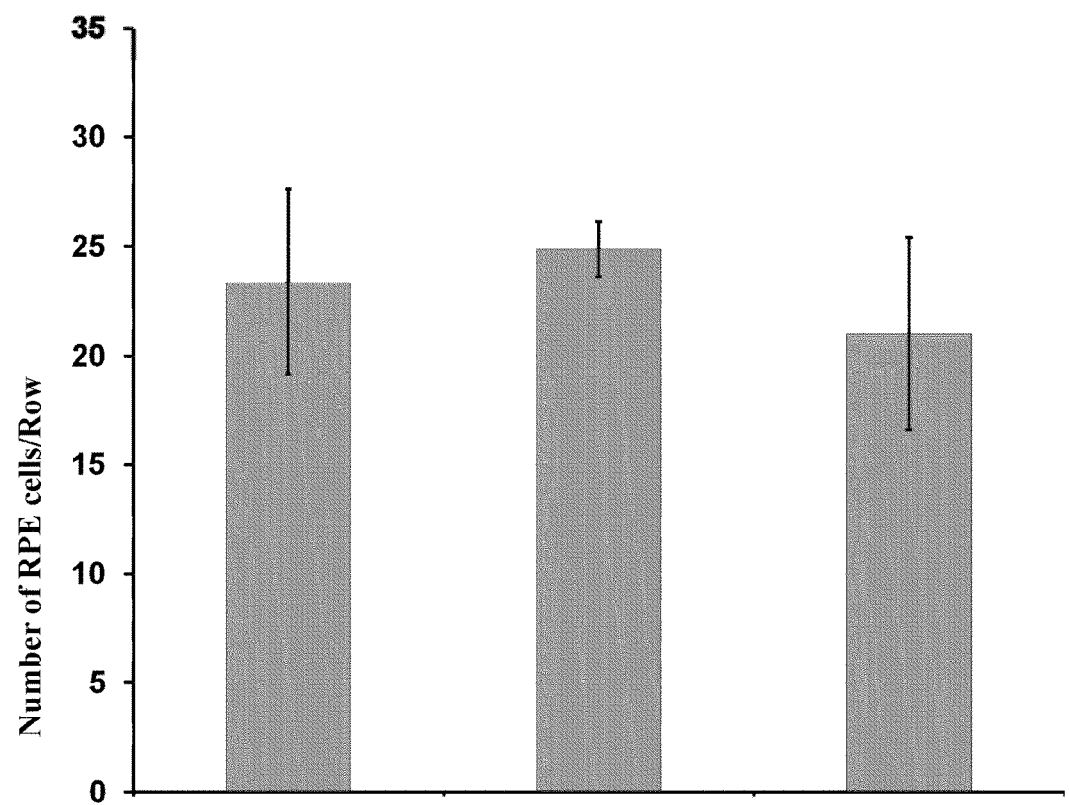

As shown in FIGS. 34A and 34B, which depict an hESC-seeded substrate (A) and corresponding cell counts from various portions of the substrate (B), a baseline average of about 27 RPE cells per row of the substrate. The substrates were implanted into the eye of RCS rats, and one day later removed to determine the amount of cell loss (if any) due to shear forces during implantation. FIGS. 35A and 35B depict the substrate after implantation. FIGS. 35C-35H depict hematoxylin and eosin stained sections depicting the substrate positioned adjacent to the photoreceptors (at the indicated magnifications). As shown in FIGS. 36A and 36B (same techniques as in FIG. 34), the number of RPE cells per row was slightly, but not significantly less after implantation.

This study demonstrates that RPE monolayers cultured on parylene substrates can be successfully implanted into the subretinal space of RCS rats. In several embodiments, similar substrates are implanted into other mammals (e.g., humans). The monolayer structure of the RPE cells is maintained after transplantation. Moreover, no significant cell losses occur due to the effect of surgical shear force.

Example 11

Restoration of Visual Function after RPE-Substrate Implantation

The ultimate test of any cellular therapy is an in vivo restoration of function. In the case of macular degeneration, a key symptom is blindness of the subject. Restoration of sight, even if only partial, can drastically improve the quality of life of subjects suffering from macular degeneration.

Figure 37:
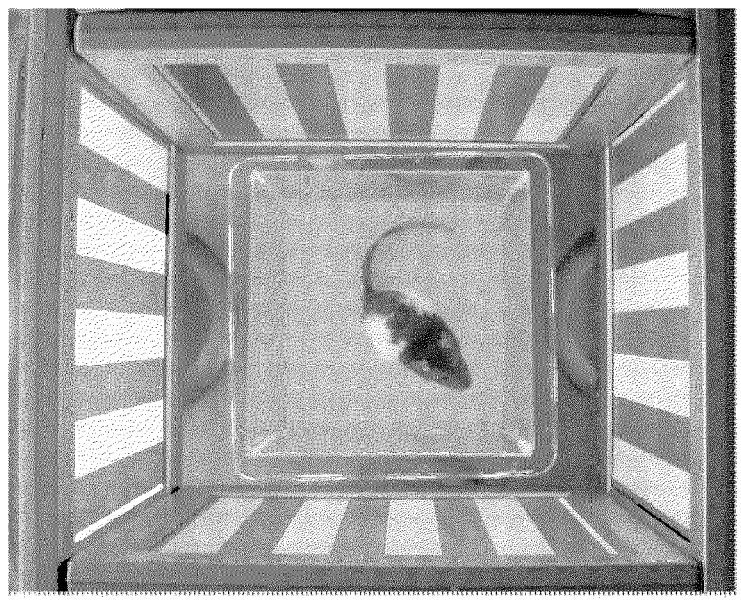
FIG. 37 depicts an optokinetic nystagmus (OKN) chamber.

The present example furthers the studies above. Using the methods, devices, and substrates disclosed herein, RPE-seeded substrates were implanted into the subretinal space of RCS (and control Long Evans rats). Behavioral profile of chance (POC) was used to evaluate the efficacy of the implantation of the RPE-seeded substrates. Optokinetic head-tracking was used to evaluate behaviour in a double blinded study using two readers. The testing apparatus consisted of four computer monitors arranged in a square to form an OKN chamber, which is an established technique in the art (see FIG. 37). Rats were released into a clear plexiglass container placed over an elevated platform located at the center of the OKN chamber. Computer software was used to generate alternate black and white stripes that were moved across all four computer monitors. The response of the animals during each test (duration of testing=2 minutes) were recorded using a digital camcorder. Tests were performed every two weeks after surgery until termination. At each time point, rats were tested three times and a minimum three minute interval was maintained between two consecutive tests. The recorded videos were evaluated to measure the OKN response which is assessed based on the duration of head-tracking (computed with the help of a digital stop-watch). To evaluate the reproducibility of the testing method and the reliability of the scoring system, tests are randomly repeated by a second observer. Both evaluators were masked to the experimental status of the animal.

Figure 38:
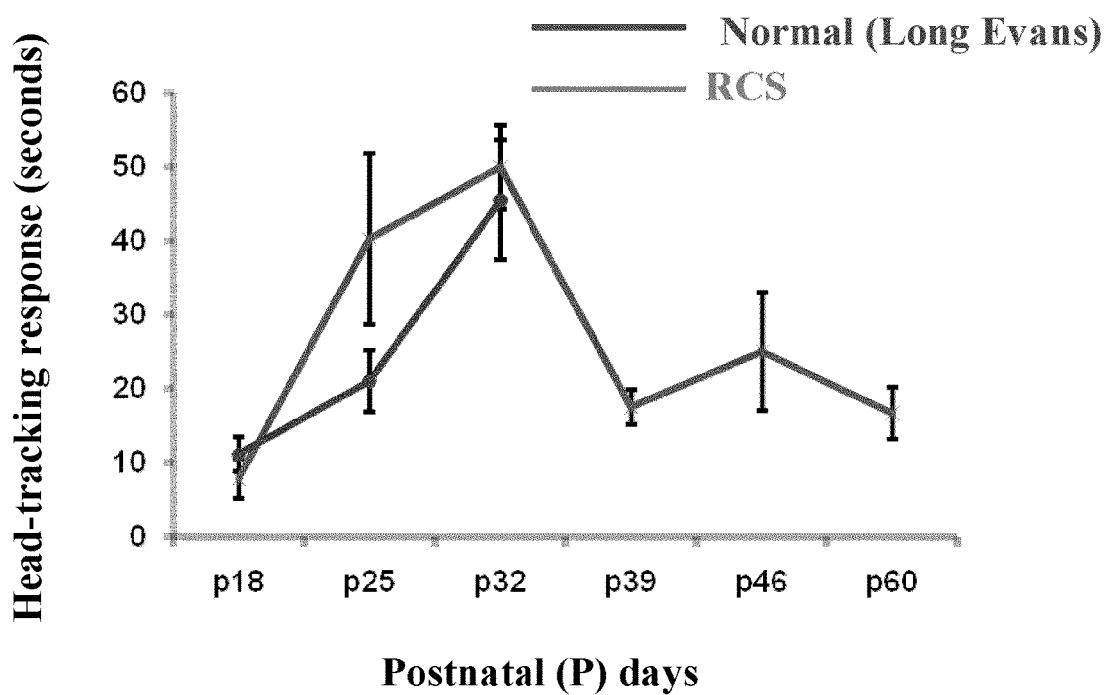
FIG. 38 depicts functional recover of vision behavior in a dystrophic rat.

As shown in FIG. 38, implantation of RPE-seeded substrates into the rat sub-retinal space allowed dystrophic rats to, based on a behavioral analysis, see at a level that was not substantially different from that of normal rats. In several embodiments, in conjunction with the functional data (lipfuscin) and the anatomical data (maintained monolayer) above, these studies strongly indicate that RPE cells implanted with the devices, methods, and substrates disclosed herein can restore, at least partially, vision to a subject having macular degeneration. In several embodiments, other non-ocular disease can be treated with substrates and cells tailored to particular diseases.

Example 12

Long-term Interdigitation of hESC-RPE and PR Outer Segments in Rat Eye

As discussed above, interdigitation of hESC-RPE cells with the outer segments of the photoreceptors allows the functional and metabolic interaction between the RPE cells and photoreceptors to take place. This interaction supports the viability of the photoreceptors and as discussed in the prior examples, leads to functional vision recovery. In this example, the long term engraftment and interdigitation of RPE cells in dystrophic rats was assessed by transmission electron microscopy.

As with the Examples above, substrates comprising RPE cells were implanted into the subretinal space of dystrophic RCS rats at postnatal day 29. The substrate use in this example was approximately 6.5 microns this, though as discussed above, other dimensions may be used in various embodiments. Animals were sacrificed on post-natal day 38 (9 days post-surgery) and 87 (58 days after surgery). No immunosuppressive therapy was administered to the rats.

Figure 39:
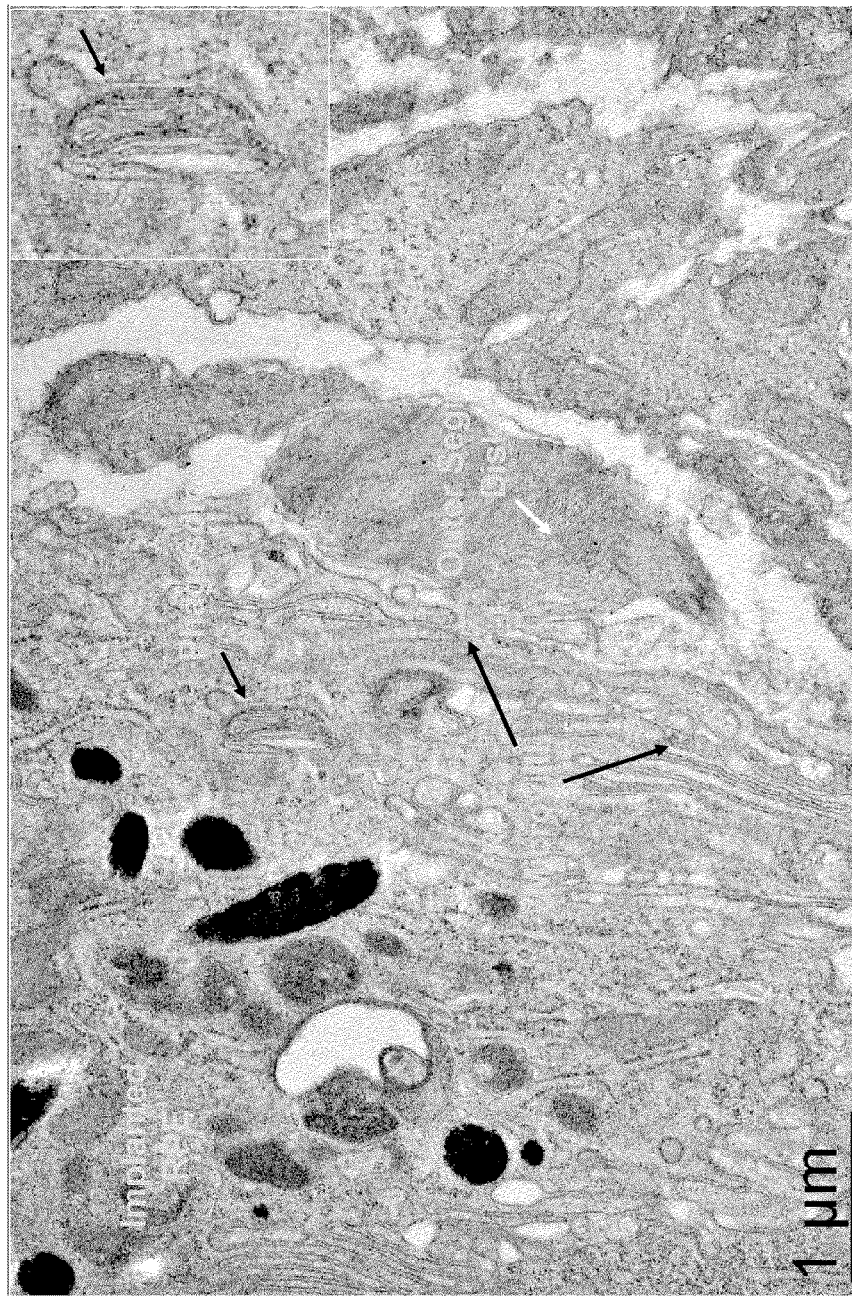
FIG. 39 depicts transmission electron microscopy of RPE cells implanted in the eye of a dystrophic rat at 9 days post-implantation.
Figure 40:
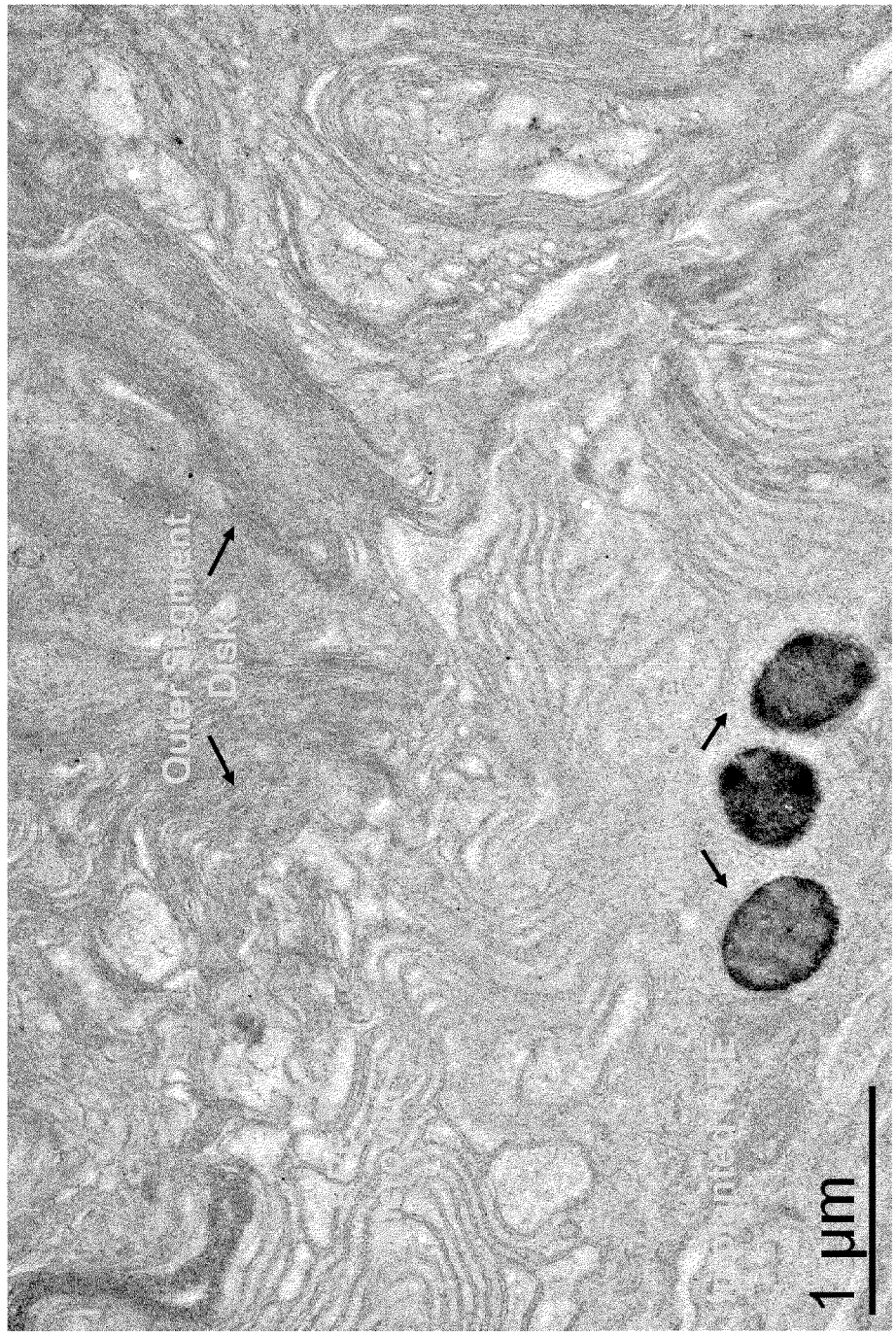
FIG. 40 depicts transmission electron microscopy of RPE cells implanted in the eye of a dystrophic rat at 58 days post-implantation. Interdigitation is visible between the RPE microvilli and the photoreceptor outer segment disks.
Figure 41:
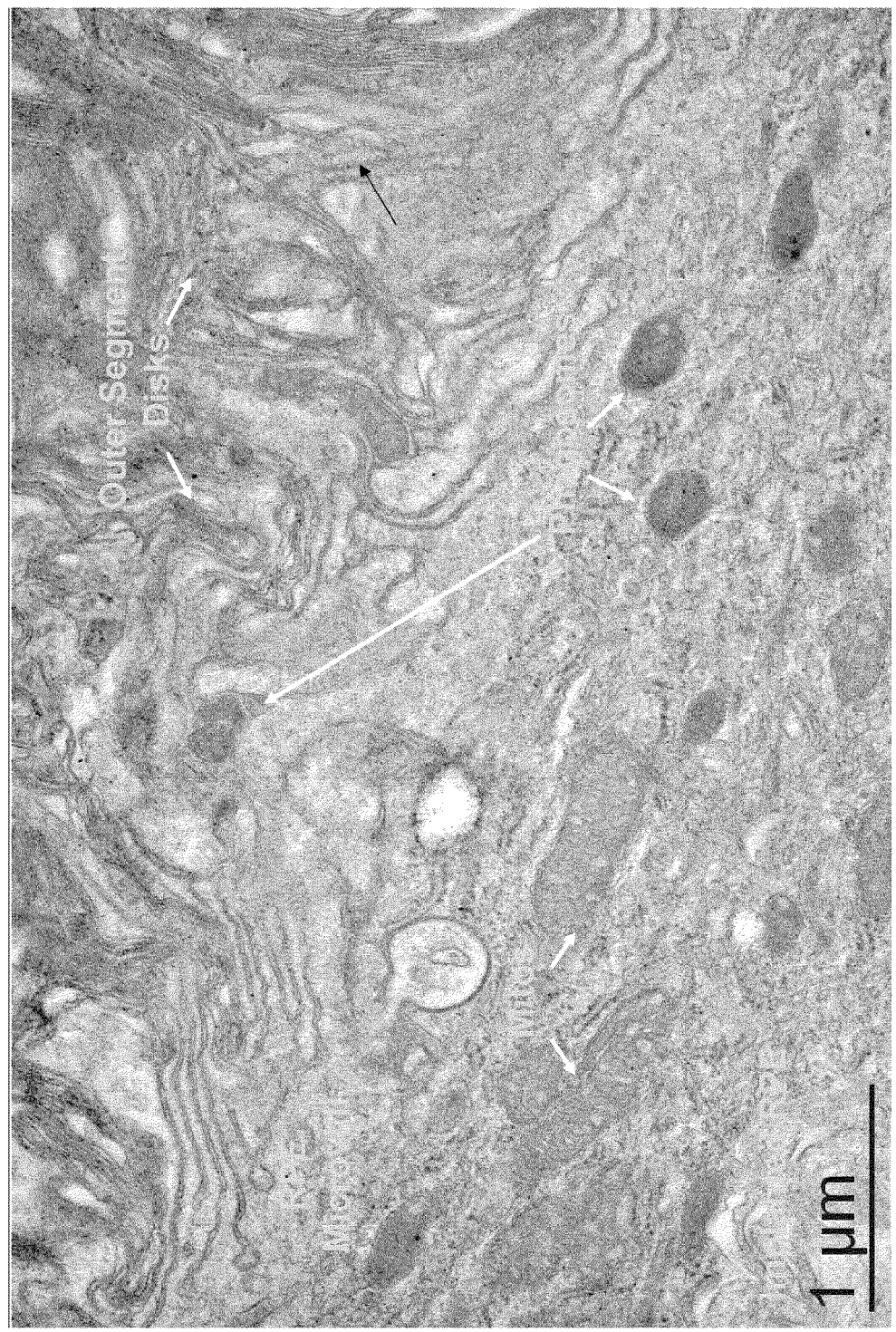
FIG. 41 depicts transmission electron microscopy of RPE cells implanted in the eye of a dystrophic rat at 58 days post-implantation. Interdigitation is visible between the RPE microvilli and the photoreceptor outer segment disks.

As shown in FIG. 39, at post-implant day 9 the RPE microvilli are localized near the outer segment disks. At post-implant day 58, shown in FIGS. 40 and 41, interdigitation between the RPE microvilli and the outer segment disks can be seen. Thus, even at extended time-points, the RPE cells are viable and are functionally interdigitated with the photoreceptor outer segment. This data demonstrates that RPEs implanted according the methods disclosed herein, and using the substrates disclosed herein, provide long-term functional engraftment of RPEs in the eye.

Various modifications and applications of embodiments of the invention may be performed, without departing from the true spirit or scope of the invention. Further, the disclosure herein of any particular feature, aspect, method, property, characteristic, quality, attribute, element, or the like in connection with an embodiment can be used in all other embodiments set forth herein. Method steps disclosed herein need not be performed in the order set forth. It should be understood that the invention is not limited to the embodiments set forth herein for purposes of exemplification, but is to be defined only by a reading of the appended claims, including the full range of equivalency to which each element thereof is entitled.

Example 13

Methods of Substrate Implantation

As discussed above, many degenerative retinal diseases are viewed as being progressive and largely irreversible, especially given the relative paucity of treatment strategies (especially long term strategies). For example, macular degeneration results from the progressive loss of function of RPE cells, eventually leading to blindness. As discussed above, stem cells, with their capacity to differentiate and replace diseased cells, are attractive cells from source for RPE transplantation/replacement. In several investigations, stem cell derived RPE transplantation was performed by injecting dissociated cells as a suspension. However, in a normal retina, RPE cells exist as a polarized monolayer. As such, injections of cell suspensions rely on the random orientation and integration of injected RPE cells into the existing monolayer.

As disclosed herein, in several embodiments that contrast with injections of cell suspensions, RPE cells derived from human embryonic stem cells (for example, the H9 line) are cultured on substrate (e.g., on parylene substrates) a polarized monolayer. In several embodiments, the cultured monolayer of cells advantageously provides a population of cells that are pre-polarized and can be placed in an optimal target location (e.g., where the native RPE cells are most damaged). Such substrates with RPE monolayers are therefore, in several embodiments, suitable for replacement therapies in the eye. However, as can be appreciated by the disclosure herein, the dimensions of the substrates that allow for the diffusion of nutrients through the substrate to the RPE cells also lead to a degree of flexibility in the implants that, if not sufficiently supported during implantation, can lead to fragility in the substrate. Thus, a variety of substrate delivery instruments was developed (which are disclosed herein). The present experiment discloses the use of a platform embodiment of a delivery instrument to implant a human embryonic stem cell derived RPE (hESC-RPE) cell-seeded substrate in the subretinal space of RCS rats. The RCS rat is considered as an acceptable model for human RPE dysfunction diseases.

Methods

Animals

Normal Copenhagen rats (Charles River Laboratories International, Inc., Wilmington, Mass.) (28-30 days old, n=6) and dystrophic RCS rats (Dr. Matthew LaVail rodent colonies—Beckman Vision Center, University of California, San Francisco) (28-30 days old, n=5) were used for subretinal implantation surgeries. Copenhagen rats were used for cell counting studies (before and after implantation), while RCS rats were used for detailed morphological evaluation of the retina post-implantation. The animals were immunosuppressed by intraperitoneal injection of dexamethasone (1.6 mg/kg/day) and oral cyclosporine (CyA administered through drinking water, 210 mg/l) starting 2 days before implantation and continuing until the end of the experiment. Rats were maintained under a 12 h light/dark cycle. All animals were maintained in accordance with the Association for Research in Vision and Opthamology (ARVO) statement for the use of animals in research, and the research was approved by the Animal Care and Use Committee of the University of Southern California.

Substrates and Stem Cells

Human embryonic stem cells (H9) (Wicell, Madison, Wis.) were spontaneously differentiated into RPE cells by established methods. Differentiated hESC-RPE cells were cultured and maintained in serum-free medium. Additional information regarding cell differentiation and culturing methods can be found in U.S. Provisional Application Ser. No. 61/593,849, filed Feb. 1, 2012, which is incorporated by reference herein. Evaluation of RPE-specific markers indicated that cultures were greater than 95% RPE. hESC-RPE cells at passage 2 were dissociated from the culture vessel and seeded on parylene substrate at a cell density of $10^5$/$cm^2$. Additional information regarding cell seeding methods can be found in U.S. Provisional Application Ser. No. 61/535,307, filed Sep. 15, 2011, which is incorporated by reference herein. The cells were then maintained in culture on the ultrathin parylene substrates for 4 weeks with the medium changed twice weekly.

Platform Device

A platform device made of parylene (10 μm thick) and having upwardly protruding barriers (B in FIG. 42 about 30 μm high) arranged along the edges in the shape of a Jr (FIG. 42; though other shapes of barrier or placement of barrier are used in other embodiments) was used to support the cell-seeded substrates during implantation. An embodiment of the platform device with examples of dimensions is shown in FIG. 42. The space inside the barriers acts as the 'substrate loading chamber' where the substrate for implantation is placed.

Surgical Procedure

After the conjunctiva was opened, extraocular muscles were maintained on traction for eyeball fixation. A small incision (approximately 0.8-1.0 mm) was cut transsclerally at the temporal equator of the host eye until the choroid was exposed. A small puncture of the anterior chamber resulted in release of a small quantity of aqueous humor and a concomitant reduction in intraocular pressure. Balanced salt solution (BSS) was injected into the subretinal space to create a focal retinal detachment. The choroid was cut with fine scissors while the retina remained intact. During implantation, the substrate containing hESC-RPE cells was loaded on the platform device with the surface of the substrate coated with cells facing upwards. The platform, along with the substrate, was held with fine forceps and gently pushed into the subretinal space through the choroidal incision. During this process, platform was oriented such that the cells on the surface of the substrate faced the vitreous side of the retina. The substrate was positioned in the target area of the subretinal space by holding it in place using the forceps and gently pulling the platform device out of the eye through the incision. Once the placement of the implant was confirmed (based on microscopic fundus examination), the incisions were and antibiotic drops were applied on the eye. The animals were allowed to recover in a thermal care incubator.

Cell Counting and Statistical Analysis Using Copenhagen Rats

Figures 43A, 43B:
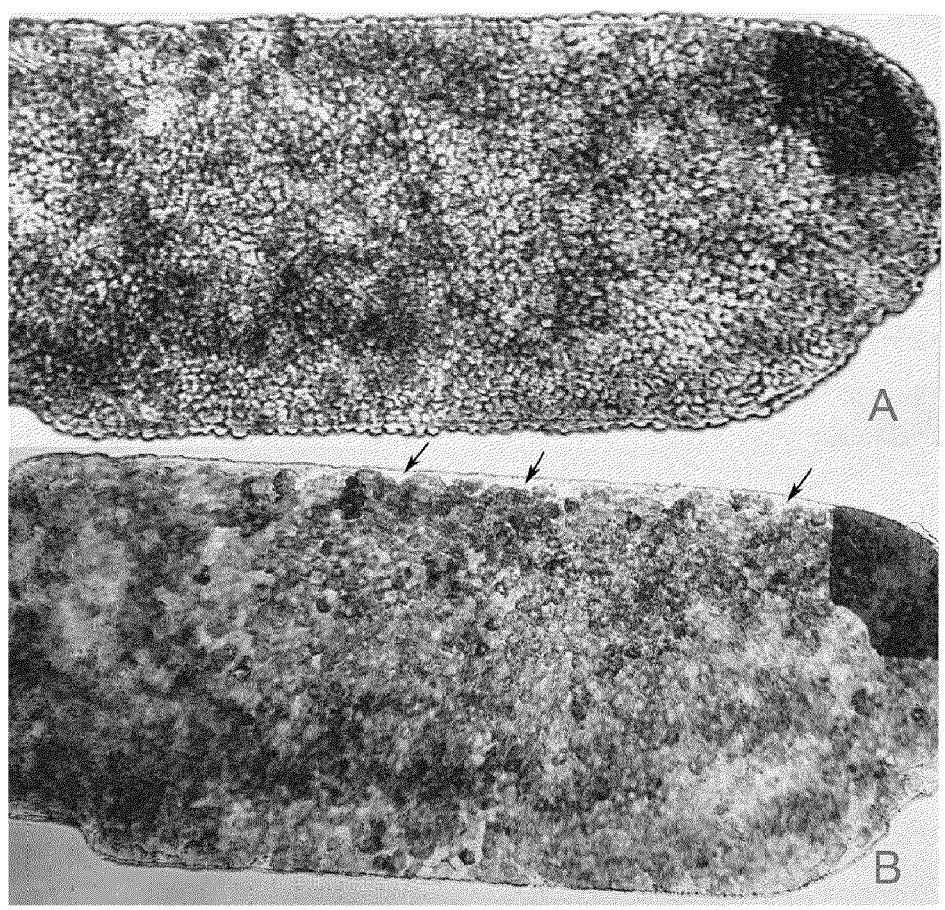
FIGS. 43A-43B depict one embodiment of a substrate as disclosed herein prior to (A) and after (B) subretinal implantation.

Photographic images of the substrate were captured before implantation using a phase contrast microscope (see e.g., FIG. 43A). Copenhagen rats were sacrificed immediately after implantation and the substrates were dissected out after enlarging the scleral and choroidal incisions. Images of the post-implantation (and post-explantation) substrate were captured after fixation with 10% formaldehyde. A grid pattern was superimposed on the images to divide a single substrate into 40 small squares using Microsoft Power-Point, and the images were printed out. Three small square areas on a single substrate were randomly picked for manual cell counting. The average of the cell numbers counted from the three areas was multiplied by 40 to determine the total cell number on the single substrate. Other counting methodologies are used in other embodiments, for example in vitro and in vivo methods disclosed in U.S. Provisional Application Ser. No. 61/481,107, filed Apr. 29, 2011, which is incorporated by reference herein. Cell counting was performed by four independent evaluators and the final cell numbers for the substrate were the average numbers from the four evaluators. Statistical comparison of the cell counting data (before and after implantation) was performed using Student's t test (Graph Pad Prism 5.0, La Jolla, Calif., USA).

SD-OCT Examination and Histological Evaluation Using RCS Rats

Immediately after implantation, the location of the implant was verified using SD-OCT (Spectralis HRA+OCT, Heidelberg Engineering Inc., Heidelberg, Germany). The RCS rats were subjected to another SD-OCT examination before termination (1 week after implantation). The eyes were enucleated, fixed, and embedded in paraffin for histological examination. Sections (5 μm thick) were stained with hematoxylin and eosin (HE) for light microscopic evaluation.

Results

Because cell-seeded substrates can be easily loaded inside the platform device between the vertical barriers, there is limited disruption of the cells on the substrate. Moreover, the barriers prevent the implant from moving away from the loading chamber during the implantation process. In all cases, after surgery, the retina remained intact and no vitreous leakage was observed. No signs of subretinal hemorrhage or lens damage were observed. Thus, in several embodiments the use of the platform device to support a cell-seeded implant as disclosed herein advantageously allows the precise placement of the substrate, with limited (or no) damage or disruption of the therapeutic cells.

SD-OCT scanning and histological examination revealed that the substrates were precisely placed in the rat's subretinal space. The hESC-RPE cell monolayer that covered the surface of the substrate was found to be intact after implantation. Cell counting data showed that less than 2% cells were lost from the substrate due to the implantation procedure (pre-implantation count 2792±74.09 cells vs. post-implantation count 2741±62.08 cells). Detailed microscopic examination indicated that the cell loss occurred primarily along the edges of the implant, where fluid shear forces are higher and the possibility of contacting non-target tissues during implantation is greater. Thus, in several embodiments, use of the platform device implantation of substrates containing RPE monolayer into the rat's subretinal space can be achieved with minimal perturbation of the cells. This technique can be a useful approach for stem cell-based tissue bioengineering techniques in retinal transplantation research.

Cell Counting

The total number of hESC-RPE cells on the substrate before implantation averaged 2792±74.09 cells/substrate. After implantation, the cell numbers were 2741±62.08 cells/substrate, ($P<0.05$, see Table 1).

TABLE 1

Pre- and Post-implantation cell counts

| | Count 1 | Count 2 | Count 3 | Count 4 | Count 5 | Count 6 | mean* ± SD |
|---|---|---|---|---|---|---|---|
| Pre-op | 2677.5 | 2740.5 | 2800 | 2803.5 | 2852.5 | 2880.5 | 2792 ± 74.09 |
| Post-op | 2654.5 | 2683.8 | 2742.8 | 2753.3 | 2803.8 | 2807.5 | 2741 ± 62.08 |

*P = 0.0006 (<0.05); t = 7.694 df = 5

This amounted to approximately 98% retention of the cells. Detailed microscopic examination revealed that the RPE monolayer structure was well preserved in all implanted substrates, with small cell loss (no more than 2%) observed almost exclusively along the edges of the substrate (FIG. 43B). Given the potential therapeutic benefits of the remaining cells on the substrate, loss of <2% of the cells, especially from the edges of the substrate is unlikely, in most embodiments, to negatively impact the overall therapy. More importantly, histological evaluation performed after implantation indicated that an intact RPE monolayer is preserved in the remaining area over the substrate. In some embodiments, the percentage of lost cells is lower, for example less than 1.5%, less than 1%, less than 0.5%, or less than 0.1%. In some embodiments however the percentage loss may be greater. Advantageously, however, the substrates and implantation tools disclosed herein allow, and several embodiments the vast majority of cells seeded on the substrate to be successfully implanted with minimal disruption. As a result, such substrates are suitable for providing therapeutic benefit to the recipient, even in light of the loss of a small portion of therapeutic cells. As disclosed above, alternative instrumentation is used in other embodiments to further reduce the cell loss during the implantation process.

SD-OCT Examination

Figures 44A, 44B:
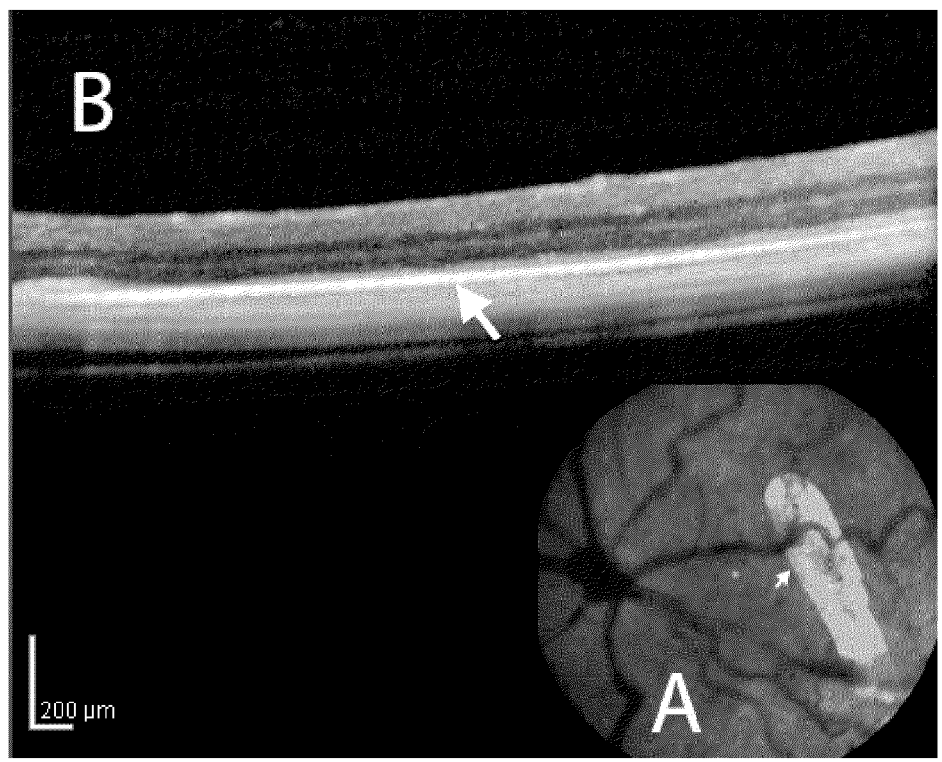
FIGS. 44A-44B depict various images of a substrate according to several embodiments disclosed herein after implantation.

Immediately after implantation, SD-OCT scanning revealed focal retinal detachment at the site of implantation as expected. In all animals, the substrate was placed as a flat sheet adjacent to Bruch's membrane. The SD-OCT examination performed in RCS rats 1 week after implantation showed subretinal placement of the implant and reattachment of the retina (FIGS. 44A-44B). Thus, while mathematically significant numbers of cells may have been lost during implantation, the positioning of the substrate with the large percentage of intact polarized cells provides, in some embodiments a therapeutically significant effect.

Histology

Figure 45:
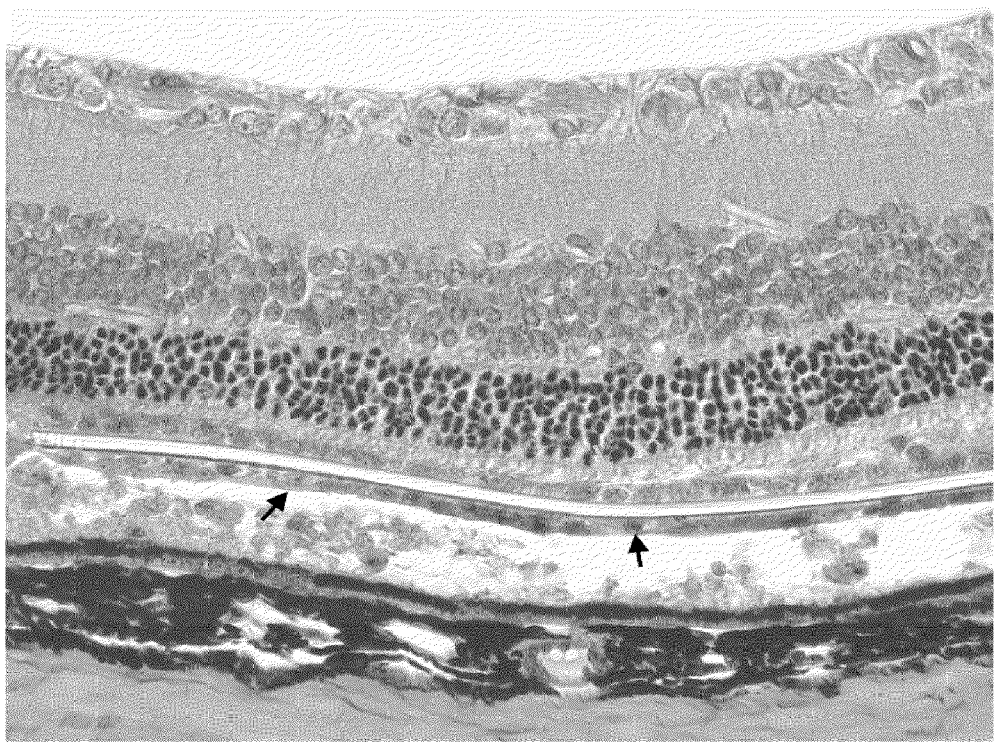
FIG. 45 depicts a hematoxylin and eosin (40×) stained section passing through the target region in which a substrate (above arrows) was implanted.

In corroboration of the SD-OCT data, microscopic examination of the histology sections revealed that substrates were precisely placed in the subretinal space as a flat sheet. The hESC-RPE cell monolayer on the substrates remained intact (FIG. 45) and no retinal trauma or damage to the Bruch's membrane was observed.

The results of these experiments demonstrate that, while cell suspension injection techniques present an arguably less technically challenging approach, transplantation of cells seeded on the substrates can only be achieved, but can be achieved in several embodiments with precise placement of the substrate and minimal disruption to the therapeutic population of cells on the substrate. Cell suspension injections may lead to the formation of isolated cell clumps that fail to develop into a polarized RPE monolayer structure. Moreover, non-polarized cells, when placed in the subretinal space, may remain nonfunctional or they may eventually die or initiate immunonological reactions. The use of cells seeded substrates that are implanted with specialized instrumentation address such issues and present advantageous treatment alternatives.

Other studies have demonstrated the use of specifically designed implantation tools, albeit with different animal models and/or with different surgical approaches. In several embodiments, the platform device employed in the present example is constructed of parylene and/or specifically designed (e.g., dimensioned) for subretinal implantation of ultrathin substrates. The device, in several embodiments, is easily loaded with a cell-seeded substrate (e.g., ultrathin parylene seeded with hESC-RPE monolayer). A transscleral approach was used to achieve subretinal placement of the substrate in these experiments, although alternative routes can also be used. The thin and flexible nature of the platform device enables access to the subretinal space with reduced risk of damage to the retina and/or the choroid during the implantation process. The raised barriers on the surface of the device, in several embodiments, prevent or otherwise minimize movement of the substrate off the surface of the device. The dimensions of platform being greater than that of the substrate protect the cells on the substrate from potential damage caused by surgical shear forces. As evidenced by the over 98% retention of cells (limited primarily to the edges of the substrate) the results indicate that therapeutically relevant cell numbers are delivered to the target tissue via the substrate.

Advantageously, the instruments disclosed herein allow for the implantation of the cell seeded substrate sub-retinally without the adverse effect of large retinal detachments that may result in retinal folding during reattachment. Moreover, since the mechanical yield strength of the implantation device is purposefully designed to be relatively low (e.g., the platform is flexible), possible damage to the retinal tissue or Bruch's membrane during is advantageously reduced, resulting in less surgical recovery time and improved patient outcomes.

What is claimed is:

1. An instrument for an implantation of a substrate into a target tissue of a subject, comprising:
    a handpiece comprising a proximal end and a distal end, said distal end comprising an orifice;
    an outer housing extending in a distal direction from said handpiece, a distal end of the outer housing terminating in a bevel;
    an internal shaft configured to be longitudinally moveable within said outer housing and said handpiece;
    forceps connected with the internal shaft;
    a shaft movement control mechanism; and
    a planar substrate having a tail and a body of a same thickness as the tail,
    wherein activation of said movement control mechanism causes longitudinal movement of said internal shaft and forceps;
    wherein movement of said internal shaft in a proximal direction is configured to cause said forceps to grasp the tail of the substrate, induce a rolling of the substrate against the bevel of said outer housing, and retract the substrate within said outer housing, and
    wherein movement of said internal shaft in a distal direction is configured to cause the substrate to exit said outer housing and unroll and cause said forceps to open.

2. The instrument of claim 1, wherein said movement control mechanism comprises a slide mechanism.

3. The instrument of claim 1, wherein said movement control mechanism comprises a friction wheel mechanism.

4. The instrument of claim 1, wherein said movement control mechanism comprises one or more racks associated with said forceps and a gear mechanism that interacts with said racks.

5. The instrument of claim 1, further comprising an injection pathway.

6. The instrument of claim 5, wherein said injection pathway is configured to deliver a media from the handpiece to a target site at or near a distal-most portion of the internal shaft.

7. The instrument of claim 1, further comprising:
    a substrate support platform with which said forceps are configured to reversibly interact.

8. The instrument of claim 7, wherein after interacting with the substrate support platform, proximal longitudinal movement of the movement control mechanism is configured to retract the internal shaft resulting in contact between outer edges of the substrate support platform and an inner portion of the outer housing, thereby inducing the substrate support platform to roll into a cylindrical shape.

9. The instrument of claim 8, wherein distal longitudinal movement of the movement control mechanism causes the outer edges of the substrate support platform to move distally beyond the outer housing, thereby allowing the rolled support platform to unroll.

10. The instrument of claim 1, wherein the substrate has a curved region between the tail and the body.

11. The instrument of claim 10, wherein a length of the tail is between 1 mm and 20 mm.

12. The instrument of claim 11, wherein a length of the tail is between 1 mm and 2 mm.

13. The instrument of claim 1, wherein a width of the tail is between 0.2 mm and 6 mm.

14. An instrument for an implantation of a substrate into a target tissue of a subject, comprising:
 a handpiece comprising a proximal end and a distal end, said distal end comprising an orifice;
 an outer housing extending in a distal direction from said handpiece, a distal end of the outer housing terminating in a bevel;
 an internal shaft configured to be longitudinally moveable within said outer housing and said handpiece;
 forceps connected with the internal shaft;
 a shaft movement control mechanism; and
 an injection pathway within the outer housing,
 wherein activation of said movement control mechanism causes longitudinal movement of said internal shaft and forceps;
 wherein movement of said internal shaft in a proximal direction is configured to cause said forceps to grasp a tail of the substrate, induce a rolling of the substrate against the bevel of said outer housing, and retract the substrate within said outer housing, and
 wherein movement of said internal shaft in a distal direction is configured to cause the substrate to exit said outer housing and unroll and cause said forceps to open.

15. The instrument of claim 14, further comprising:
 a substrate having a tail, a body, and a curved region between the tail and the body.

16. The instrument of claim 14, wherein said movement control mechanism comprises a slide mechanism.

17. The instrument of claim 14, wherein said movement control mechanism comprises a friction wheel mechanism.

* * * * *